United States Patent [19]

Jacobs et al.

[11] Patent Number: 5,635,509

[45] Date of Patent: Jun. 3, 1997

[54] PIPERIDINE DERIVATIVES USEFUL AS NEUROKININ ANTAGONISTS

[75] Inventors: Robert T. Jacobs, Cheshire, England; Scott C. Miller, Newark, Del.; Ashokkumar B. Shenvi, Wilmington, Del.; Cyrus J. Ohnmacht, Jr., Wilmington, Del.; Chris A. Veale, Newark, Del.

[73] Assignee: Zeneca Limited, London, England

[21] Appl. No.: 432,309

[22] Filed: May 1, 1995

[30] Foreign Application Priority Data

May 3, 1994 [GB] United Kingdom ............... 9408872

[51] Int. Cl.⁶ ............... A61K 31/505; C07D 239/10
[52] U.S. Cl. ............... 514/274; 544/315; 544/316; 544/318
[58] Field of Search ............... 514/274, 315, 514/316, 318

[56] References Cited

U.S. PATENT DOCUMENTS

| | | | |
|---|---|---|---|
| 4,782,061 | 11/1988 | Kruse et al. | 514/254 |
| 5,236,921 | 8/1993 | Emonds-Alt et al. | 514/252 |

FOREIGN PATENT DOCUMENTS

| | | |
|---|---|---|
| 2029275 | 5/1991 | Canada . |
| 2067924 | 11/1992 | Canada . |
| 2090785 | 9/1993 | Canada . |
| 0190472 | 8/1986 | European Pat. Off. . |
| 0428434 | 5/1991 | European Pat. Off. . |
| 0474561 | 3/1992 | European Pat. Off. . |
| 0515240 | 11/1992 | European Pat. Off. . |
| 0512901 | 11/1992 | European Pat. Off. . |
| 0512902 | 11/1992 | European Pat. Off. . |
| 0559538 | 9/1993 | European Pat. Off. . |
| 0625509 | 11/1994 | European Pat. Off. . |
| 0630887 | 12/1994 | European Pat. Off. . |
| 923177 | of 0000 | South Africa . |
| 923178 | 1/1993 | South Africa . |
| 2248449 | 4/1992 | United Kingdom . |
| WO91/09844 | 7/1991 | WIPO . |
| WO94/10146 | 5/1994 | WIPO . |
| WO94/29309 | 12/1994 | WIPO . |
| WO95/05377 | 2/1995 | WIPO . |
| WO95/12577 | 5/1995 | WIPO . |

OTHER PUBLICATIONS

A. Graham et al., "Isolation and Characterisation of the Human Lung NK–2 Receptor Gene Using Rapid Amplification of cDNA Ends", *Biochemical and Biophysical Research Communications*, (1991), vol. 177, No. 1, 8–16.

X. Emonds–Alt et al., "Pharmacological Profile and Chemical Synthesis of SR 48968, a Non–Peptide Antagonist of the Neurokinin A ($NK_2$) Receptor", *Biorganic & Medicinal Chemistry Letters*, (1993), vol. 3, No. 5, 925–930.

D. Aharony et al., "Pharmacologic Characterization of the Novel Ligand [4,5–³H–LEU⁹]Neurokinin–A Binding to NK–2 Receptors on Hamster Urinary Bladder Membranes", *Neuropeptides*, (1992), 23, 121–130.

M. Needham et al., "LCR/MEL: A Versatile System for High–Level Expression of Heterologous Proteins in Erythroid Cells", *Nucleic Acids Research*, (1992), vol. 20, No. 5, 997–1003.

*Primary Examiner*—Yogendra N. Gupta
*Attorney, Agent, or Firm*—Robert J. Harris

[57] ABSTRACT

Compounds of formula I

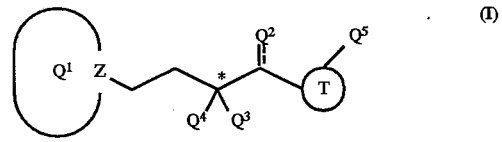

wherein $Q^1$, $Q^2$, $Q^3$, and $Q^4$ have any of the meanings given in the specification, their N-oxides, and their pharmaceutically acceptable salts are nonpeptide antagonists of neurokinin A and useful for the treatment of asthma, etc. Also disclosed are pharmaceutical compositions, processes for preparing the compounds of formula I and intermediates.

11 Claims, No Drawings

PIPERIDINE DERIVATIVES USEFUL AS NEUROKININ ANTAGONISTS

This invention concerns novel heterocyclic compounds which antagonize the pharmacological actions of one of the endogenous neuropeptide tachykinins known as neurokinins, particularly at the neurokinin 2 (NK2) receptor. The novel heterocyclic compounds are useful whenever such antagonism is desired. Thus, such compounds may be of value in the treatment of those diseases in which an NK2 receptor is implicated, for example, in the treatment of asthma and related conditions. The invention also provides pharmaceutical compositions containing the novel heterocyclic compounds for use in such treatment, methods for their use, and processes and intermediates for the manufacture of the novel heterocyclic compounds.

The mammalian neurokinins comprise a class of peptide neurotransmitters which are found in the peripheral and central nervous systems. The three principal neurokinins are Substance P (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, respectively, the receptors are classified as neurokinin 1 (NK1) neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation and activation of mast cells. Thus, the tachykinins are implicated in the pathophysiology and the airway hyperresponsiveness observed in asthmatics; and blockade of the action of released tachykinins may be useful in the treatment of asthma and related conditions. Peptidic NK2 antagonists have been reported. For example, a cyclic hexapeptide known as L-659,877 has been reported as a selective NK2 antagonist. Nonpeptidic NK2 antagonists also have been reported, for example in European Patent Application, Publication Number (EPA) 428434, EPA 474561, EPA 512901, EPA 512902 and EPA 515240, as well as in EPA 559538, EPA 625509 and EPA 630887 and International Patent Application Publication Number WO 94/148,184. We have discovered a series of nonpeptidic NK2 antagonists, and this is the basis for our invention.

According to the invention, there is provided a Compound of the invention which is a compound of formula I (formula set out hereinbelow following the Examples, together with other formulae denoted by Roman numerals) wherein $Q^1$ is a radical (attached at Z) selected from the group of radicals of formulae Ia, Ib, Ic, Id, Ie, If, Ig, Ih, Ij and Ik wherein for a radical of formula Ia, $Z^a$ is nitrogen or a group $CR^{ad}$ in which $R^{ad}$ is hydrogen or $R^{ad}$ together with $R^{ac}$ and the existing carbon to carbon bond forms a double bond; $R^{aa}$ is Ar or Het; $R^{ab}$ is hydrogen and $R^{ac}$ is hydrogen or hydroxy or $R^{ac}$ together with $R^{ad}$ and the existing carbon to carbon bond forms a double bond, or $R^{ac}$ and $R^{ad}$ together form a diradical —$(CH_2)_j$— in which j is an integer from 1 to 5; or $R^{ab}$ and $R^{ac}$ together form a diradical —$(CH_2)_k$— in which k is an integer from 2 to 6, or $R^{ab}$ and $R^{ac}$ together are oxo or dialkylaminoalkyloxyimino of formula =N—O—$(CH_2)_q$—$NR^{ae}R^{af}$ in which q is the integer 2 or 3 and $R^{ae}$ and $R^{af}$ are independently hydrogen or (1–4C)alkyl, or the radical $NR^{ae}R^{af}$ is pyrrolidino, piperidino or morpholino;

for a radical of formula Ib, $Z^b$ is a substituted imino group $R^{ba}N$ or $R^{ba}CH_2N$ in which $R^{ba}$ is (3–7C)cycloakyl, Ar or Het; or $Z^b$ is a disubstituted methylene group $R^{bb}(CH_2)_p$—C—$R^{bc}$ in which $R^{bb}$ is Ar or Het; p is the integer 0 or 1; and $R^{bc}$ is hydrogen, hydroxy, (1–4C)alkoxy, (1–4C)alkanoyloxy, $COOR^{bd}$ (wherein $R^{bd}$ is hydrogen or (1–3C)alkyl), cyano, $NR^{be}R^{bf}$ or $SR^{bg}$ in which $R^{be}$ and $R^{bf}$ are independently hydrogen, (1–4C)alkyl, (1–4C)hydroxyalkyl or (1–4C)alkanoyl, or the radical $NR^{be}R^{bf}$ is pyrrolidino, piperidino or morpholino; and $R^{bg}$ is hydrogen or (1–4C)alkyl; or $R^{bc}$ forms a double bond with the carbon atom to which it is bonded and with the adjacent carbon atom in the piperidine ring;

or $Z^b$ is a disubstituted methylene group $R^{bh}CR^{bi}$ which forms a spirocyclic ring wherein $R^{bh}$ is phenyl which is joined by an ortho-substituent diradical $X^b$ to $R^{bi}$ in which the phenyl $R^{bh}$ may bear a further substituent selected from halo, (1–3C)alkyl, (1–3C)alkoxy, hydroxy, (1–3C)alkylthio, (1–3C)alkylsulfinyl and (1–3C)alkylsulfonyl; the diradical $X^b$ is methylene, carbonyl or sulfonyl; and $R^{bi}$ is oxy or imino of formula —$NR^{bj}$— in which $R^{bj}$ is hydrogen or (1–3C)alkyl;

for a radical of formula Ic, $R^{ca}$ is Ar or Het; and $Z^c$ is oxo, thio, sulfinyl, sulfonyl or imino of formula —$NR^{cb}$— in which $R^{cb}$ is (1–3C)alkyl or $R^{cc}R^{cd}N$—$(CH_2)_q$— in which q is the integer 2 or 3 and in which $R^{cc}$ and $R^{cd}$ are independently hydrogen or (1–3C)alkyl or the radical $R^{cc}R^{cd}N$ is pyrrolidino, piperidino or morpholino;

for a radical of formula Id, $R^{da}$ is hydrogen, (1–6C)alkyl, Ar, Het, α-hydroxybenzyl, styryl, or $R^{db}$-(1–3C)alkyl in which $R^{db}$ is aryl, pyridyl, pyridylthio or 1-methyl-2-imidazolylthio in which an aromatic group or portion of $R^{da}$ may bear one or more halo, hydroxy, (1–4C)alkyl or (1–4C)alkoxy substituents; $X_d$ is oxy or —$CHR^{dc}$—; $R^{dc}$ is hydrogen, hydroxy, (1–3C)alkoxy, (1–4C)alkanoyloxy, $NR^{dd}R^{de}$ or (1–4C)alkanoylamino; $R^{dd}$ and $R^{de}$ are independently hydrogen or (1–4C)alkyl or the radical $NR^{dd}R^{de}$ is pyrrolidino, piperidino or morpholino; p is the integer 0 or 1; and $Z^d$ is a single bond (except when $R^{da}$ is hydrogen or p is 1), methylene or carbonyl;

for a radical of formula Ie, $J^e$ is oxygen, sulfur or $NR^{ea}$ in which $R^{ea}$ is hydrogen or (1–3C)alkyl; $R^{eb}$ is hydrogen, (1–6C)alkyl which may bear a hydroxy substituent and/or one to three fluoro substituents, (3–6C)alkenyl (in which a vinyl carbon is not bound to nitrogen), 2-hydroxyethyl, (3–7C)cyloalkyl, Ar or Het; $R^{ec}$ is hydrogen, (1–6C)alkyl which may bear a hydroxy substituent and/or one to three fluoro substituents, (3–6C)cycloalkyl, (1–5C)alkoxy (only when $J^e$ is oxygen), (3–6C)cycloalkoxy (only when $J^e$ is oxygen), or an amino group of formula $NR^{ed}R^{ee}$ containing zero to seven carbon atoms in which each of $R^{ed}$ and $R^{ee}$ is independently hydrogen, (1–5C)alkyl or (3–6C)cycloalkyl, or the radical $NR^{ed}R^{ee}$ is pyrrolidino, piperidino, morpholino, thiomorpholino (or its S-oxide) or piperazinyl (which piperazinyl group may bear a (1–3C)alkyl substituent at the 4-position);

for a radical of formula If, $J^f$ is oxygen, sulfur or $NR^{fa}$ in which $R^{fa}$ is hydrogen or (1–3C)alkyl; $L^f$ is a divalent hydrocarbon group in which the 1-position is bound to the carbon bearing the group $J^f$, the divalent group $L^f$ being selected from trimethylene, cis-propenylene, tetramethylene, cis-butenylene, cis-but-3-enylene, cis,cis-butadienylene, pentamethylene and cis-pentenylene which divalent group $L^f$ itself may bear one or two methyl substituents;

for a radical of formula Ig, $Z^g$ is (1–8C)alkyl or (3–8C)cycloalkyl which may bear one or more substituents selected from the group consisting of halo, (3–6C)cycloalkyl, cyano, nitro, hydroxy, (1–4C)alkoxy, (1–5C)alkanoyloxy, aroyl, heteroaroyl, oxo, imino (which may bear a (1–6C)alkyl, (3–6C)cycloalkyl, (1–5C)alkanoyl or aroyl substituent), hydroxyimino (which hydroxyimino may bear a (1–4C)alkyl or a phenyl substituent on the oxygen), an amino group of formula $NR^{ga}R^{gb}$, an amino group of formula $NR^{gc}R^{gd}$, an amidino group of formula $C(=NR^{gg})NR^{ge}R^{gf}$, and a carbamoyl group of formula $CON(OR^{gh})R^{gi}$, but excluding any radical wherein a hydroxy and an oxo substituent together form a carboxy group, wherein an amino group of formula $NR^{ga}R^{gb}$ contains zero to seven carbon atoms and each of $R^{ga}$ and $R^{gb}$ is independently hydrogen, (1–5C)alkyl or (3–6C)cycloalkyl, or the radical $NR^{ga}R^{gb}$ is pyrrolidino, piperidino, morpholino, thiomorpholino (or its S-oxide) or piperazinyl (which piperazinyl may bear a (1–3C)alkyl substituent group at the 4-position); and wherein $R^{gc}$ is hydrogen or (1–3C)alkyl and $R^{gd}$ is (1–5C)alkanoyl, aroyl or heteroaroyl; or $R^{gd}$ is a group of formula $C(=Jg)NR^{ge}R^{gf}$ in which $J^g$ is oxygen, sulfur, $NR^{gg}$ or $CHR^{gj}$; and wherein the amino group $NR^{ge}R^{gf}$ contains zero to seven carbon atoms and each of $R^{ge}$ and $R^{gf}$ is independently hydrogen, (1–5C)alkyl or (3–6C)cycloalkyl, or the radical $NR^{ge}R^{gf}$ is pyrrolidino, piperidino, morpholino, thiomorpholino (or its S-oxide) or piperazinyl (which piperazinyl may bear a (1–3C)alkyl substituent at the 4-position) or $R^{ge}$ is hydrogen or (1–4C)alkyl and $R^{gf}$ together with $R^{gg}$ forms an ethylene or trimethylene group; $R^{gg}$ is hydrogen, (1–4C)alkyl or together with $R^{gf}$ forms an ethylene or trimethylene group; $R^{gj}$ is cyano, nitro or $SO_2R^{gk}$ and $R^{gk}$ is (1–4C)alkyl or phenyl; $R^{gh}$ and $R^{gi}$ are independently (1–3C)alkyl; and in which a cyclic group which is a substituent on $Z^g$ or formed by substitution on $Z^g$ may bear one or more (1–3C)alkyl groups on carbon as further substituents; and in which any aryl or heteroaryl group which is a part of the group $Z^g$ may bear one or more halo, (1–4C)alkyl, (1–4C)alkoxy, cyano, trifluoromethyl or nitro substituents;

for a radical of formula Ih, $G^h$ denotes a single bond, a double bond or a divalent hydrocarbon radical; $J^h$ denotes a radical joined to the ring by a single bond if $G^h$ denotes a double bond or, otherwise, a radical joined by a double bond; $M^h$ denotes a heteroatom a substituted heteroatom, or a single bond; and $L^h$ denotes a hydrocarbon radical in which the 1-position is attached to $M^h$; wherein the values of $G^h$, $J^h$, $M^h$ and $L^h$ are selected from (a) $G^h$ is a single bond; $J^h$ is oxo or thioxo; $M^h$ is oxy, thio or $NR^{ha}$; and $L^h$ is $L^{ha}$;

(b) $G^h$ is a single bond; $J^h$ is $NR^{hb}$; $M^h$ is $NR^{ha}$; and $L^h$ is $L^{ha}$;

(c) $G^h$ is a double bond; $J^h$ is $OR^{ha}$, $SR^{ha}$ or $NR^{hc}R^{hd}$; $M^h$ is nitrogen; and $L^h$ is $L^{ha}$;

(d) $G^h$ is methylene which may bear one or two methyl substituents; $J^h$ is oxo, thio or $NR^{he}$; $M^h$ is oxy, thio, sulfinyl, sulfonyl or $NR^{ha}$; and $L^h$ is $L^{hb}$;

(e) $G^h$ is a single bond; $J^h$ is oxo, thioxo or $NR^{he}$; $M^h$ is nitrogen; and $L^h$ is $L^{hc}$;

(f) $G^h$ is methine, which may bear a (1–3C)alkyl substituent; $J^h$ is oxo, thioxo or $NR^{he}$; $M^h$ is nitrogen; and $L^h$ is $L^{hd}$;

(g) $G^h$ is cis-vinylene, which may bear one or two methyl substituents; $J^h$ is oxo, thioxo, or $NR^{he}$; $M^h$ is nitrogen; and $L^h$ is $L^{he}$; and (h) $G^h$ is a single bond; $J^h$ is oxo or thioxo; $M^h$ is a single bond; and $L^h$ is $L^{hf}$; wherein $R^{ha}$ is hydrogen or (1–3C)alkyl; $R^{hb}$ is hydrogen, (1–3C)alkyl, cyano, (1–3C)alkylsulfonyl or nitro; $R^{hc}$ and $R^{hd}$ are independently hydrogen or (1–3C)alkyl or the radical $NR^{hc}R^{hd}$ is pyrrolidino, piperidino, morpholino, thiomorpholino (or its S-oxide) or piperazinyl (which piperazinyl may bear a (1–3C)alkyl substituent at the 4-position); $R^{he}$ is hydrogen or (1–3C)alkyl; $L^{ha}$ is ethylene, cis-vinylene, trimethylene or tetramethylene which radical $L^{ha}$ itself may bear one or two methyl substituents; $L^{hb}$ is ethylene or trimethylene which radical $L^{hb}$ itself may bear one or two methyl substituents; $L^{hc}$ is prop-2-en-1-yliden-3-yl, which radical $L^{hc}$ itself may bear one or two methyl substituents; $L^{hd}$ is cis-vinylene, which radical $L^{hd}$ itself may bear one or two methyl substituents; $L^{he}$ is methine, which radical $L^{he}$ itself may bear a (1–3C)alkyl substituent; and $L^{hf}$ is 4-oxabutan-1,4-diyl;

for a radical of formula Ij, $X^j$ is (1–6C)alkyl, —$CH_2OR^{ja}$, —$CH_2SR^{ja}$, —$CH_2S(O)R^{jg}$, —$CH_2S(O)_2R^{jg}$, —$COR^{ja}$, —$COOR^{ja}$, —$C(=J^{ja})NR^{jb}R^{jc}$, —$C(R^{ja})(OR^{jd})(OR^{je})$, —$CH_2N(R^{ja})C(=J^{ja})R^{jf}$, —$CH_2N(R^{ja})COOR^{jg}$ or —$CH_2N(R^{ja})C(=J^{ja})NR^{jb}R^{jc}$;

$B^j$ is a direct bond and $L^j$ is a hydrocarbon chain in which the 1-position is bound to $B^j$ and $L^j$ is selected from trimethylene, tetramethylene, cis-1-butenylene and cis,cis-butadienylene; or $B^j$ is $N(R^{jh})$ and $L^j$ is a hydrocarbon chain selected from ethylene, trimethylene and cis-vinylene; or $B^j$ is N and $L^j$ is a hydrocarbon chain in which the 1-position is bound to $B^j$ and $L^j$ is cis,cis-prop-2-en-1-ylidin-3-yl; $J^j$ and $J^{ja}$ are independently oxygen or sulfur; $R^{ja}$, $R^{jf}$ and $R^{jh}$ are independently hydrogen or (1–6C)alkyl; $R^{jb}$ and $R^{jc}$ are independently hydrogen or (1–6C)alkyl; or the radical $NR^{jb}R^{jc}$ is pyrrolidino, piperidino, morpholino, thiomorpholino (or its S-oxide) or piperazinyl (which piperazinyl may bear a (1–3C)alkyl substituent at the 4-position); $R^{jd}$ and $R^{je}$ are independently (1–3C)alkyl or together form a divalent hydrocarbon chain selected from ethylene and trimethylene; $R^{jg}$ is (1–6C)alkyl; and for a radical of formula Ik, $Z^k$ is a nitrogen linked radical of formula II wherein $E^1$, $E^2$, $E^3$ and $E^4$ form a divalent four membered chain (—$E^1$=$E^2$—$E^3$=$E^4$—) in which each of $E^1$, $E^2$, $E^3$ and $E^4$ is methine; or in which one or two of $E^1$, $E^2$, $E^3$ and $E^4$ is nitrogen and the remaining $E^1$, $E^2$, $E^3$ and $E^4$ are methine; and further wherein one or more of $E^1$, $E^2$, $E^3$ and $E^4$ which is methine may bear a halo, (1–3C)alkyl, hydroxy, (1–3C)alkoxy, (1–3C)alkylthio, (1–3C)alkylsulfinyl or (1–3C)alkylsulfonyl substituent; and wherein the radicals $F^k$, $G^k$, and $I^k(X^k)$ are selected from (a) $G^k$ is a direct bond, $I^k(X^k)$ is a radical having the formula =$C(Z^k)$— and $F^k$ is a radical selected from —CH= and —N=;

(b) $G^k$ is a direct bond, $I^k(X^k)$ is a radical having the formula —$C(=J^k)$— and $F^k$ is a radical selected from —$N(R^{kf})$—, —$CH_2$—$CH_2$—, —CH=CH—, —$CH_2$—N($R^{kf}$)— and —CH=N—;

(c) $G^k$ is a radical having the formula —$CH_2$—, $I^k(X^k)$ is a radical having formula —$C(=J^k)$— and $F^k$ is selected from —$CH_2$— and —$N(R^{kf})$—; and (d) $G^k$ is selected from —$CH_2$—, —$CH_2$—$CH_2$—, —CH=CH— and —N=CH—, $I^k(X^k)$ is a radical having the formula —$C(=J^k)$— and $F^k$ is a direct bond; wherein $J^k$ is oxygen or sulfur; $Z^k$ is —$OR^{ka}$, —$SR^{ka}$, —$COR^{ka}$, —$COOR^{ka}$, —$C(=J^{ka})NR^{kb}R^{kc}$ or —$C(R^{ka})(OR^{kd})(OR^{ke})$; $J^{ka}$ is oxygen or sulfur; $R^{ka}$ and $R^{kf}$ are independently hydrogen or (1–6C)alkyl; $R^{kb}$ and $R^{kc}$ are independently hydrogen or (1–6C)alkyl; or the radical $NR^{kb}R^{kc}$ is pyrrolidino, piperidino, morpholino, thiomorpholino (or its S-oxide) or piperazinyl (which piperazinyl may bear a (1–3C)alkyl substituent at the 4-position); $R^{kd}$ and $R^{ke}$ are independently (1–3C)alkyl or $R^{kd}$ and $R^{ke}$ together form ethylene or trimethylene; or $Z^k$ is an imido radical selected from phthalimido, succinimido, maleimido, glutarimidos and 3-oxa-, 3-thia- and 3-azaglutarimido, in which the imido radical may bear one or more (1–3C)alkyl substituents and, in addition, the aromatic portion of the phthalimido may bear one or more halo, hydroxy or (1–3C)alkoxy substituents; and wherein for a radical $Q^1$, Ar is a phenyl radical or an ortho-fused bicyclic carbocyclic radical of nine of ten ring atoms in which at least one ring is aromatic, which radical Ar may be unsubstituted or may bear one or more substituents selected from halo, cyano, trifluoromethyl, (1–4C)alkyl, (1–4C) alkoxy, methylenedioxy, hydroxy, mercapto, $-S(O)_nR^{xa}$, (1–5C)alkanoyl, (1–5C)alkanoyloxy, nitro, $NR^{xb}R^{xc}$, $NR^{xd}R^{xe}$, $C(=NR^{xf})NR^{xg}R^{xh}$, $CONR^{xb}R^{xc}$ and $COOR^{xj}$ wherein n is the integer 0, 1, or 2; $R^{xa}$ is (1–6C)alkyl, (3–6C)cycloalkyl or phenyl (which phenyl may bear a halo, trifluoromethyl, (1–3C)alkyl or (1–3C)alkoxy substitutent); the radical $NR^{xb}R^{xc}$ contains zero to seven carbons and each of $R^{xb}$ and $R^{xc}$ is independently hydrogen, (1–5C)alkyl or (3–6C)cycloalkyl, or the radical $NR^{xb}R^{xc}$ is pyrrolidino, piperidino, morpholino, thiomorpholine (or its S-oxide) or piperazinyl (which piperazinyl may bear a (1–3C)alkyl substituent at the 4-position); and wherein $R^{xd}$ is hydrogen or (1–4C)alkyl and $R^{xe}$ is (1–5C)alkanoyl, benzoyl; or a group of formula $C(=J^{xf})NR^{xg}R^{xh}$ in which $J^x$ is oxygen, sulfur, $NR^{xf}$ or $CHR^{xi}$; $R^{xf}$ is hydrogen, (1–5C)alkyl or together with $R^{xg}$ forms an ethylene or trimethylene diradical, the radical $NR^{xg}R^{xh}$ contains zero to 7 carbons and each of $R^{xg}$ and $R^{xh}$ is independently hydrogen, (1–5C)alkyl or (3–6C)cycloalkyl, or the radical $NR^{xg}R^{xh}$ is pyrrolidino, piperidino, morpholino, thiomorpholino (or its S-oxide) or piperazinyl (which piperazinyl may bear a (1–3C)alkyl substituent at the 4-position); or $R^{xg}$ together with $R^{xf}$ forms an ethylene or trimethylene diradical and $R^{xh}$ is hydrogen or (1–5C)alkyl; $R^{xi}$ is cyano, nitro, (1–5C)alkylsulfonyl or phenylsulfonyl; and $R^{xj}$ is hydrogen, (1–5C)alkyl or benzyl; and Het is a radical (or stable N-oxide thereof) attached via a ring carbon of a monocyclic aromatic ring containing five or six ring atoms consisting of carbon and one to four heteroatoms selected from oxygen, sulfur and nitrogen, or an ortho-fused bicyclic heterocycle derived therefrom by fusing a propenylene, trimethylene, tetramethylene or benzdiradical, which radical Het may be unsubstituted or may be substituted on carbon by one or more of the substituents defined above for Ar and may be substituted on nitrogen by (1–3C)alkyl;

$Q^2$ is a mono valent radical selected from hydroxy, (1–3C)alkoxy, $-SR^5$, $-OC(=O)R^6$, $-OC(=O)NR^7R^8$; or divalent radical selected from thioxo and oxo;

$R^5$ is hydrogen, (1–3C)alkanoyl, (1–3C)alkyl, phenyl, or phenyl(1–3C)alkyl, wherein any phenyl may optionally be substituted by 1–3 substituents selected from halo, (1–3C) alkyl, and (1–3C)alkoxy;

$R^6$ is (1–4C)alkyl, phenyl, or phenyl(1–3C)alkyl, wherein any phenyl may optionally be substituted by 1–3 substituents selected from halo, (1–3C)alkyl, and (1–3C)alkoxy;

$R^7$ and $R^8$ are independently hydrogen, (1–4C)alkyl, phenyl, or phenyl(1–3C)alkyl, wherein any phenyl may optionally be substituted by 1–3 substituents selected from halo, (1–3C)alkyl, and (1–3C)alkoxy;

$Q^3$ is hydrogen or (1–3C)alkyl;

$Q^4$ is phenyl which may bear one or two substituents independently selected from halo, trifluoromethyl, hydroxy, (1–3C)alkoxy, (1–3C)alkyl and methylenedioxy; or $Q^4$ is thienyl, imidazolyl, benzo[b]thiophenyl or naphthyl any of which may bear a halo substituent; or $Q^4$ is biphenylyl; or $Q^4$ is carbon-linked indolyl which may bear a benzyl substituent at the 1-position;

T is a carbon-linked five-membered aromatic ring containing 2–3 nitrogens, which is substituted at a ring position adjacent to the carbon-link by a group $Q^5$; and $Q^5$ is (1–6C)alkyl (which may contain a double or triple bond), (3–6C)cycloalkyl (which may contain a double bond), (3–6C)oxacycloalkyl (which may contain a double bond), aryl, aryl(1–3C)alkyl, or 5- or 6-membered heteroaryl (or N-oxide thereof) consisting of carbon and one to four heteroatoms selected from oxygen, sulfur and nitrogen, in which an aryl or heteroaryl radical or portion of a radical may bear one or more substituents on carbon selected from (1–3C)alkyl, (1–3C)alkoxy, methylenedioxy, halogeno, hydroxy, (1–4C)acyloxy and $NR^AR^B$ in which $R^A$ and $R^B$ are independently hydrogen or (1–3C)alkyl, or $R^A$ is hydrogen or (1–3C)alkyl and $R^B$ is (1–4C)acyl;

or the N-oxide of a piperidino nitrogen indicated by Δ (or of either basic piperazinyl nitrogen of $Q^1$ when $Z^a$ is nitrogen);

or a pharmaceutically acceptable salt thereof;

or a quaternary ammonium salt thereof in which the piperidino nitrogen indicated by Δ (or either basic piperazinyl nitrogen of $Q^1$ when $Z^a$ is nitrogen) is a quadricovalent ammonium nitrogen wherein the fourth radical on the nitrogen $R^1$ is (1–4C)alkyl or benzyl and the associated counterion A is a pharmaceutically acceptable anion.

A subgroup of the invention is a compound of formula I wherein $Q^2$ is a mono valent or divalent radical selected from hydroxy, acetoxy, (1–3C)alkoxy and oxo, wherein $Q^1$, $Q^2$, T and $Q^5$ have any of the meanings given above for a compound of formula I;

or the N-oxide of a piperidino nitrogen indicated by Δ (or of either basic piperazinyl nitrogen of $Q^1$ when $Z^a$ is nitrogen);

or a pharmaceutically acceptable salt thereof;

or a quaternary ammonium salt thereof in which the piperidino nitrogen indicated by Δ (or either basic piperazinyl nitrogen of $Q^1$ when $Z^a$ is nitrogen) is a quadricovalent ammonium nitrogen wherein the fourth radical on the nitrogen $R^1$ is (1–4C)alkyl or benzyl and the associated counterion A is a pharmaceutically acceptable anion.

Another subgroup of the invention is a compound of formula III, or a pharmaceutically acceptable salt thereof, wherein $Q^{1a}$ is a radical of formula $Q^1$ defined above for a compound of formula I in which Z denotes a nitrogen and $Q^2$, T and $Q^5$ have any of the meanings given above for a compound of formula I.

It will be appreciated that a compound of formula I (or III) contains one or more asymmetrically substituted carbon atoms such that such a compound may be isolated in optically active, racemic and/or diastereomeric forms. A compound may exhibit tautomerization. A compound may exhibit polymorphism. It is to be understood that the present invention encompasses any racemic, optically-active, diastereomeric, tautomeric, polymorphic or stereoisomeric form, or mixture thereof, which form possesses NK2 antagonist properties, it being well known in the art how to prepare optically-active forms (for example, by resolution of the racemic form or by synthesis from optically-active starting materials) and how to determine the NK2 antagonist properties by the standard tests described hereinafter. It may be preferred to use the compound of formula I (or III) in an optically pure form which is characterized as containing, for example, at least 95%, 98% or 99% enantiomeric excess of a particular form. For example, it may be preferred to use the compound of formula I (or III), or a particular diastereomer thereof, in a form which is characterized as containing at least 95%, 98% or 99% enantiomeric excess of the form with the (R)- or the (S)-configuration at the center(s) indicated by * in the formulae.

In this specification $R^{aa}$, $R^{ab}$, $R^1$, $R^2$, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl (except where more specifically defined) denotes a phenyl radical or an ortho-fused bicyclic carbocyclic radical having abut nine to ten ring atoms in which at least one ring is aromatic. Heteroaryl (except where more specifically defined) encompasses a radical attached via a ring carbon of a monocyclic aromatic ring containing five ring atoms consisting of carbon and one to four heteroatoms selected from oxygen, sulfur and nitrogen or containing six ring atoms consisting of carbon and one or two nitrogens, as well as a radical of an ortho-fused bicyclic heterocycle of about eight to ten atoms derived therefrom, particularly a benz-derivative or one derived by fusing a propenylene, trimethylene of tetramethylene diradical thereto, as well as a stable N-oxide thereof. Aroyl is arylcarbonyl; heteroaroyl is heteroarylcarbonyl.

A pharmaceutically acceptable salt is one made with an acid which provides a physiologically acceptable anion.

Particular values are listed below for radicals or portions thereof (for example, particular values for (1–3C)alkyl provide particular values for the alkyl portion of (1–3C)alkoxy or (1–3C)alkylsulfinyl), substituents and ranges for a compound of formula I or formula III as described above for illustration only and they do not exclude other defined values or other values within defined ranges for the radicals and substituents.

A particular value for Ar is phenyl which may be unsubstituted or may bear a chloro, methyl, methoxy, hydroxy or methylsulfinyl substituent. A particular value for Het is furyl, thienyl, 2-imidazolyl, 1,3,4-oxadiazol-2-yl, pyridyl or pyrimidinyl which ring may be unsubstituted or may bear a chloro, methyl, methoxy, hydroxy, methylsulfinyl, methoxycarbonyl or ethoxycarbonyl substituent. A particular value for aryl is phenyl. A particular value for heteroaryl is furyl, pyridyl or pyrimidinyl. A particular value for halo is chloro or bromo. A particular value for (1–3C)alkyl is methyl, ethyl, propyl or isopropyl; for (1–4C)alkyl is methyl, ethyl, propyl, isopropyl, butyl, isobutyl or t-butyl; for (1–5C)alkyl is methyl, ethyl, propyl, isopropyl, butyl, isobutyl, t-butyl, pentyl or isopentyl; for (1–6C)alkyl is methyl, ethyl, propyl, isopropyl, butyl, isobutyl, t-butyl, pentyl, isopentyl, hexyl or isohexyl; and for (1–8C)alkyl is methyl, ethyl, propyl, isopropyl, isopentyl, 1-ethylpropyl, hexyl, isohexyl, 1-propylbutyl, or octyl. A particular value for (3–6C) cylcoalkyl is cyclopropyl, cyclopentyl or cyclohexyl; for (3–7C)cycloalkyl is cyclopropyl, cyclopentyl, cyclohexyl or cycloheptyl; and for (3–8C)cycloalkyl is cyclopropyl, cyclopentyl, cyclohexyl, cycloheptyl or cyclooctyl. A particular value for (3–6C)alkenyl is allyl, 2-butenyl or 3-methyl-2-butenyl. A particular value for (1–4C)alkanoyl is formyl, acetyl, propionyl, butyryl or isobutyryl; and for (1–5C)alkanoyl is formyl, acetyl, propionyl, butyryl, isobutyryl, valeryl, isovaleryl or pivaloyl.

A more particular value for Ar is phenyl which may be unsubstituted or may bear a methoxy, hydroxy or methylsulfinyl substituent. A more particular value for Het is pyridyl or pyrimidinyl which ring may be unsubstituted or may bear a methoxy, hydroxy or methylsulfinyl substituent. A more particular value for heteroaryl is pyridyl. A more particular value for halo is chloro. A more particular value for (1–3C)alkyl is methyl; for (1–4C)alkyl is methyl or ethyl; for (1–5C)alkyl is methyl, ethyl, propyl or isopropyl; for (1–6C)alkyl is methyl, ethyl, propyl, isopropyl, butyl, isobutyl or t-butyl; and for (1–8C)alkyl is methyl, ethyl, propyl, isopropyl, 1-ethylpropyl or 1-propylbutyl. A more particular value for (3–6C)cylcoalkyl is cyclopropyl or cyclopentyl; for (3–7C)cycloalkyl is cyclopropyl or cyclopentyl; and for (3–8C)cycloalkyl is cyclopropyl, cyclopentyl, cyclohexyl or cycloheptyl. A more particular value for (3–6C)alkenyl is allyl. A more particular value for (1–4C)alkanoyl is formyl or acetyl; and for (1–5C)alkanoyl is formyl, acetyl, propionyl, butyryl or isobutyryl.

A particular value for $Q^1$ is 4-benzylpiperidino, 4-(3-methoxyphenyl)piperidino, 4-(2-methylsulfinyl) phenylpiperidino, 4-(2-pyridyl)piperidino, 4-(3-pyridyl) piperidino, 4-(2-methylsulfinylpyrid-3-yl piperidino, 4-hydroxy-4-phenylpiperidino, 4-acetamido-4-phenylpiperidino, 4-(N-phenylacetamido)piperidino, 4-(2-hydroxyethyl)piperidino, 4-(1-hydroxy-1-propylbutyl) piperidino, 4-(2-oxopyrrolidin-1-yl)piperidino, 4-(2-oxopiperidino)piperidino, 4-(2-thioxopiperidino)piperidino, 4-(2-oxoperhydropyrimidin-1-yl)piperidino, 4-ethoxycarbonyl-4-(2-oxopiperidino)piperidino, 4-methoxycarbonyl-4-(2-oxoperhydropyrimidin-1-yl) piperidino, 4-(1-oxoisoindolin-2-yl)piperidino, 4-(2-oxo-2,3-dihydrobenzimidazol-1-yl)piperidino, 4-(2-oxo-1,2,3,4-tetrahydroquinazolin-3-yl)-iperidino or 4-methylaminocarbonyl-4-(2-oxoperhydropyrimidin-1-yl)-piperidino.

A particular value for $Q^2$ is hydroxy.

A particular value for $Q^3$ is hydrogen.

A particular value for $Q^4$ is 3,4-dichlorophenyl or 3,4-methylenedioxyphenyl.

A particular value for T is imidazol-2-yl, pyrazol-4-yl, pyrazol-3-yl, pyrazol-5-yl, triazol-4-yl, or triazol-5-yl.

A particular value for $Q^5$ is phenyl.

A particular value for $R^1$ is methyl or benzyl and for A is, for example, chloride, bromide or methanesulfonate.

A more particular value for $Q^1$ is 4-hydroxy-4-phenylpiperidino, 4-acetamido-4-phenylpiperidino, 4-acetamido-4-(2-oxopiperidino)piperidino, 4-(1-ethyl-1-hydroxypropyl)piperidino, 4-(2-oxopiperidino)piperidino, or 4-(2-oxoperhydropyrimidin-1-yl)piperidino.

A more particular value for T is triazol-5-yl.

A particular group of compounds of formula III is one in which $Q^{1a}$ is a radical of formula If, Ih or Ig and wherein J is oxygen and in which the radicals and substituents may have any of the values, particular values or more particular values defined above; or a pharmaceutically acceptable salt thereof.

A particular group of compounds of formula I is one in which $J^e$, $J^f$, $J^g$, $J^j$, $J^{ja}$, $J^k$ and $J^{ka}$ are oxygen and $J^h$ is oxo; $Q^2$ is hydroxy; $Q^3$ is hydrogen; $Q^4$ is phenyl which may bear one or two substituents selected from halo, trifluoromethyl and methylenedioxy; and $Q^5$ is phenyl.

A more particular group of compounds of formula I is one in which $Q^1$ is a radical of of formula If, Ih or, Ij and wherein J is oxygen and in which the radicals and substituents may have any of the values, particular values or more particular values defined above; or a pharmaceutically acceptable salt thereof..

It is preferred that the center indicated by * in formula I and formula III be of the (S)-configuration and, when $Q^2$ is a mono valent radical, that the absolute configuration at the carbon to which $Q^2$ is attached be (R). In general, for a compound of formula I or formula III, it is preferred that the stereochemistry correspond to that identified above, although the designation of an asymmetric center as (R)- or (S)- may vary with the particular molecule owing to the sequence rules for nomenclature.

Specific compounds of formula I (and of formula III) are described in the accompanying Examples.

Pharmaceutically acceptable salts of a compound of formula I (or of formula III) include those made with a strong inorganic or organic acid which affords a physiologically acceptable anion, such as, for example, hydrochloric, sulfuric, phosphoric, methanesulfonic, or para-toluenesulfonic acid.

A compound of formula I (or of formula III) may be made by processes which include processes known in the chemical art for the production of structurally analogous heterocyclic compounds. Such processes and intermediates for the manufacture of a compound of formula I (or of formula III) as defined above are provided as further features of the invention and are illustrated by the following procedures in which the meanings of generic radicals are as defined above unless otherwise indicated:

(a) For a compound of formula I in which Z denotes a nitrogen (or for a compound of formula III), alkylating a piperidine of formula IIIa (wherein $Q^{1a}$ is a radical of formula $Q^1$ defined above for a compound of formula I in which Z denotes a nitrogen) with an aldehyde of formula IV (or of formula IVa), by reductive alkylation. The alkylation is preferably carried out by a conventional reductive alkylation, for example as described in Example 1, by the in situ, acid-catalyzed formation of an imminum salt, followed by reduction with sodium cyanoborohydride in alcoholic solvent.

(b) Alkylating a piperidine of formula IIIa with an alkylating agent of formula V (or of formula Va) in which Y is a leaving group. Typical values for Y include for example, iodide, bromide, methanesulfonate, p-toluenesulfonate, trifluoromethanesulfonate, and the like. The reaction may be carried out under standard conditions, for example in a suitable solvent at a temperature in the range of –20° to 100° C., preferably in the range of 0° to 50° C.

(c) For an N-oxide of the piperidino nitrogen indicated by Δ of a compound of formula I (or of formula III), oxidizing the piperidino nitrogen indicated by Δ of a compound of formula I using a conventional procedure, such as, for example, using hydrogen peroxide in methanol, peracetic acid, 3-chloroperoxybenzoic acid in an inert solvent (such as dichloromethane) or dioxirane in acetone.

(d) For a quaternary ammonium salt of the piperidino nitrogen indicated by Δ of a compound of formula I (or of formula III), alkylating the piperidino nitrogen indicated by Δ of the compound of formula I (or of formula III) with an alkylating agent of formula $R^1Y$ or alkylating a piperidine of formula IIIb with an alkylating agent of formula V, wherein Y is a leaving group, followed, if required, by exchanging the counterion Y for a different counterion A by a conventional method. Typical values for Y include those listed above. Exchange of counterions may conveniently be carried out using a basic ion exchange resin in the "A" form.

(e) For a compound of formula I in which $Q^1$ is of formula Id, reducing the double bond of a corresponding starting material of formula VI using a conventional method.

(f) For a compound of formula I in which $Q^1$ is of formula Id, substituting the nitrogen of a compound of formula VIa with a radical of formula $R^{da}-(X^d)_p-Z^d-$ using a conventional method.

(g) For a compound of formula I (or of formula III) which bears a sulfinyl group, oxidizing the sulfur of a corresponding compound of formula I (or of formula III) which bears a sulfide group using a conventional method.

(h) For a compound of formula I (or of formula III) which bears a sulfonyl group, oxidizing a sulfide or sulfinyl group of a corresponding compound of formula I (or of formula III) using a conventional method.

(i) For a compound of formula I (or of formula III) which bears an aromatic hydroxy group, cleaving the ether of a corresponding compound of formula I (or of formula III) which bears an aromatic alkoxy group using a conventional method.

(j) For a compound of formula I in which $Q^2$ is oxo, reacting an amide of formula VII, wherein R2 and R3 are independently (1–3C)alkyl, with a suitable carbanion, for example as described in Example 1.

(k) For a compound of formula I wherein $Q^2$ is hydroxy, reducing a corresponding compound of formula I wherein $Q^2$ is oxo with a suitable reducing agent, such as for example sodium borohydride as described in Example 2. This method may be preferred for the preparation of compounds of formula I wherein $Q^2$ is hydroxy and $Q^3$ is hydrogen and wherein $Q^2$ and $Q^4$ are in a syn-configuration, since the syn product may be favored in this reduction.

(l) Reacting an alkyne of formula VIII with a suitable dipolar reagent, for example diazomethane or azide, to form the heteroaromatic group T, using conventional methods. For example, suitable conditions are described in Examples 3 and 4.

(m) For a compound of formula I wherein $Q^2$ is hydroxy, hydrolyzing a corresponding acetoxy compound of formula I using conventional methods. For example, hydrolysis may be carried out under basic aqueous conditions as described in Example 10.

(n) For a compound of formula I wherein $Q^2$ is acetoxy or (1–3C)alkoxy, treating a corresponding compound of formula I wherein $Q^2$ is hydroxy under conventional conditions, to form the acetoxy or (1–3C)alkoxy group.

It may be desired to optionally use a protecting group during all or portions of the above described processes; the protecting group then may be removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. Such reactions and modifications include, for example, introduction of nitro or halogeno and reduction of nitro. The reagents and reaction conditions for such procedures are well known in the chemical art.

If not commercially available, the necessary starting materials for the above procedures may be made by procedures which are selected from standard techniques of heterocyclic chemistry, techniques which are analogous to the synthesis of known, structurally similar compounds (particularly those described in the above noted EPA publications and their counterparts), and techniques which are analogous to the above described procedures or the procedures described in the Examples. The starting materials and the procedures for their preparation are additional aspects of the invention.

General synthetic routes for the preparation of starting materials are outlined in Schemes I–IV. As outlined in Scheme I, an intermediate of formula IV, wherein $Q^2$ is acetoxy, can be prepared from an ester of formula IX, wherein R4 is for example (1–3C)alkyl, by treatment with a suitable base followed by allyl bromide to give the ester X. Hydrolysis of the ester X to the acid XI followed by amide formation gives an amide of formula XII. Treatment of an amide of formula XII with a lanthanum or cerium salt of an anion of a compound of formula XVIII, yields a ketone XIII. The ketone XIII may be reduced to the alcohol XIV which may be converted to the acetoxy compound XV. The starting material aldehyde IV, wherein $Q^2$ is acetoxy, may be prepared from XV by oxidative cleavage of the olefin using conventional procedures, for example as described in sub-part f. of Example 7. This synthetic route may be preferred for the preparation of compounds of formula IV wherein $Q^2$ is acetoxy, $Q^3$ is hydrogen, and wherein $Q^2$ and $Q^4$ are in a syn-configuration, since the syn product may be favored in the reduction of the ketone XIII to the alcohol XIV.

As outlined in Scheme II, an intermediate of formula IV, wherein $Q^2$ is acetoxy, can be prepared from an ester of formula XIX, wherein R4 is for example (1–3C)alkyl, by reduction to the alcohol XX and conversion to the aldehyde XXI. Treatment of an aldehyde of formula XXI with a lanthanum or cerium salt of an anion of a compound of formula XVIII, yields an alcohol of formula XXII. The starting material aldehyde IV, wherein $Q^2$ is acetoxy, may be prepared from XXII by conversion to the acetoxy compound XV followed by oxidative cleavage of the olefin using conventional proceedures, for example as described in sub-part f. of Example 7. This synthetic route may be preferred for the preparation of compounds of formula IV wherein $Q^2$ is acetoxy, $Q^3$ is hydrogen, and wherein $Q^2$ and $Q^4$ are in an anti-configuration, since the anti product may be favored in the conversion of the aldehyde XXI to the alcohol XXII.

As outlined in Scheme III, an intermediate of formula VII, wherein Z is nitrogen, may be prepared from an amide of formula XII. Conversion of XII to an aldehyde of formula XVI, followed by reductive coupling with a compound of formula IIIa yields a starting material of formula VII, wherein Z is nitrogen.

As outlined in Scheme IV, a starting material of formula VIII, wherein $Q^2$ is oxo, may be prepared by reaction of an amide of formula VII with an anion of formula XVII, wherein M represents a suitable counterion. For example, suitable conditions for the preparation of an intermediate of formula VIII are described in sub-part a. of Example 3.

Starting material piperidines of formula IIIa may be prepared from commercially available materials, for example a 1-protected 4-piperidone or a 1-protected 4-aminopiperidine, using conventional methods. Compounds of formula IIIa may also be prepared using methods similar to those described in the Examples hereinbelow. When a compound of formula IIIa containing a thiocarbonyl group is required, it conveniently may be obtained from a corresponding 1-protected piperidine intermediate containing a carbonyl group oxygen by treatment with phosphorous pentasulfide or with Lawesson's reagent, 2,4-bis(4-methoxyphenyl)-1,3-dithia-2,4-diphosphetane-2,4-disulfide, followed by deprotection of the piperidino nitrogen.

A starting material piperidine of formula IIIb may be obtained from a piperidine of formula IIIa by reductive alkylation to introduce the substutient $R^1$, or the compound may be prepared in a manner analogous to the preparation of a piperidine of formula IIIa.

A starting material of formula VI may be prepared from a corresponding ketone of formula VIb by a conventional method, for example by condensation with a a compound of formula VIc in which $R^{dx}$ and $R^{dy}$ together form a triphenylphosphoranylidene radical or with the anion obtained by deprotonation of a compound of formula VIc wherein $R^{dx}$ is a dimethylphosphono radical and $R^{dy}$ is hydrogen. A compound of formula VIc may be obtained from a compound of formula V using a conventional method. A starting material of formula VIa may be prepared analogously from a 1-protected 4-pyridone, followed by reduction and deprotection.

As will be clear to one skilled in the art, a variety of sequences is available for preparation of the starting materials, and the sequences leading to the starting materials and products of the invention may be altered if appropriate considerations regarding the synthetic methods and radicals present are followed.

The utility of a compound of the invention or a pharmaceutically acceptable salt thereof (hereinafter, collectively referred to as a "Compound") may be demonstrated by standard tests and clinical studies, including those disclosed in the EPA publications noted above, such as EPA 428434 or EPA 474561 (or U.S. Pat. No. 5,236,921), and those described below.

Neurokinin A (NKA) Receptor-binding Assay (Test A)

The ability of a Compound of the invention to antagonize the binding of NKA at the NK2 receptor may be demonstrated using an assay using the human NK2 receptor expressed in Mouse Erythroleukemia (MEL) cells, as described in: Aharony, D., Little, J., Thomas, C., Powell, S., Berry, D. and Graham, A. Isolation and Pharmacological Characterization of a Hampster Neurokinin A Receptor cDNA, *Molecular Pharmacology*, 1994, 45, 9–19. In an initial use of this assay, the $IC_{50}$ measured for the standard compound L-659,877 was found to be 30 nM versus $^3$H-NKA binding to MEL.

The selectivity of a Compound for binding at the NK2 receptor may be shown by determining its binding at other receptors using standard assays, for example, one using a tritiated derivative of SP in a tissue preparation selective for NK1 receptors or one using a tritiated derivative of NKB in a tissue preparation selective for NK3 receptors.

Guinea Pig Assay (Test B)

The ability of a Compound of the invention to antagonize the action of an agonist, either NKA or [β-ala$^8$]-NKA(4–10), in a pulmonary tissue may be demonstrated using a functional assay in guinea pig trachea, which is carried out as follows. The chosen agonist is refered to as AG throughout the description.

Male guinea pigs are killed by a sharp blow to the back of the head. The trachea are removed, trimmed of excess tissue and divided into two segments. Each segment is suspended as a ring between stainless steel stirrups in water-jacketed (37.5° C.) tissue baths containing a physiological salt solution of the following composition (mM): NaCl, 119; KCl 4.6; CaCl$_2$, 1.8; MgCl$_2$, 0.5; NaH$_2$PO$_4$, 1; NaHCO$_3$, 25; glucose, 11; thiorphan, 0.001; and indomethacin, 0.005; gassed continuously with 95% O$_2$-%5 CO$_2$. Initial tension placed on each tissue is 1 g, which is maintained throughout a 0.5 to 1.5 hour equilibration period before addition of other drugs. Contractile responses are measured on a Grass polygraph via Grass FT-03 force transducers.

Tissues are challenged repetitively with a single concentration of AG (10 nM) with intervening 30 min periods with washing to allow the tension to return to baseline levels. The magnitude of the contractions to AG reaches a constant level after two challenges, and each Compound is tested for inhibition of responses to AG by addition to the tissue bath 15 minute before the third or subsequent exposure to the agonist. The contractile response to AG in the presence of Compound is compared to that obtained with the second AG challenge (in the absence of Compound). Percent inhibition is determined when a Compound produces a statistically significant ($p<0.05$) reduction of the contraction and is calculated using the second contractile response as 100%.

Potencies of selected Compounds are evaluated by calculating apparent dissociation constants ($K_B$) for each concentration tested using the standard equation:

$$K_B = [\text{antagonist}]/(\text{dose ratio}-1)$$

where dose ratio=antilog[(AG -log molar $EC_{50}$ without Compound)—(AG -log molar $EC_{50}$ with Compound)]. The $K_B$ values may be converted to the negative logarithms and expressed as -log molar $K_B$ (i.e. $pK_B$). For this evaluation, complete concentration-response curves for AG are obtained in the absence and presence of Compound (30 min incubation period) using paired tracheal rings. The potency of AG is determined at 50% of its own maximum response level in each curve. The $EC_{50}$ values are converted to the negative logarithms and expressed as -log molar $EC_{50}$. Maximum contractile responses to AG are determined by expressing the maximum response to AG as a percentage of the contraction caused by carbachol (30 μM), added after the initial equilibration period. When a statistically significant ($p<0.05$) reduction of the maximum response to AG is produced by a compound, the percent inhibition is calculated relative to the percentage of carbachol contraction in the untreated, paired tissue used as 100%.

Guinea Pig Labored Abdominal Breathing
(Dyspnea) Assay (Test C)

Activity of a Compound of the invention as an antagonist of NKA at the NK2 receptor also may be demonstrated in vivo in laboratory animals, for example by adapting a routine guinea pig aerosol test described for evaluation of leukotriene antagonists by Snyder, et al. (Snyder, D. W., Liberati, N. J. and McCarthy, M. M., Conscious guinea-pig aerosol model for evaluation of peptide leukotriene antagonists. *J. Pharmacol. Meth.* (1988) 19, 219). Using the clear plastic chamber described previously by Snyder et al. to secure guinea pigs for a head-only aerosol exposure to bronchoconstrictor agonists, agonist is administered by aerosol to six conscious guinea pigs simultaneously during each maneuver. The tachykinin NK2-selective agonist, [β-ala$^8$]-NKA(4–10), $3\times10^{-5}$M, is aerosolized from a Devilbiss Model 25 ultrasonic nebulizer into an air stream entering the chamber at a rate of 2 L/minute.

Guinea pigs (275–400 g) are fasted for approximately 16 hours prior to experimentation. Compounds to be evaluated for blockade of effects of [β-ala$^8$]-NKA(4–10) or their vehicle (10% PEG400 in saline) are administered p.o. or i.v. at various times before aerosol agonist challenge. All animals are pretreated with atropine (10 mg/kg, i.p., 45 minutes pretreatment) indomethacin (10 mg/kg, i.p., 30 minutes pretreatment), propranolol (5 mg/kg, i.p., 30 minutes pretreatment), and thiorphan (1 mg/ml aerosol for 5 minutes, 15 minutes pretreatment).

Aerosol challenge with the agonist produces an initial increase in respiratory rate followed by a decrease with early signs of minor involvement of the abdominal muscles. The respiratory rate decreases further and the breathing becomes more labored with greater involvement of the abdominal muscles as exposure continues. The distinctly recognizable end point is the point where the breathing pattern of the guinea pig is consistently slow, deep, and deliberate, showing marked involvement of the abdominal muscles. Time, in seconds, from the onset of aerosol challenge to this end point is determined for each animal by using a stopwatch. The animals generally collapse after reaching the end point and do not recover from the agonist-induced respiratory distress. Antagonists result in an increase in the time to reach the end point. Animals receive the aerosol administration of agonist for a maximum time of 780 seconds.

Differences between drug treated groups and corresponding vehicle treated control groups are compared using Student's t-test for unpaired observations.

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in Test A or Test B is not limited to asthma, but rather, that the test provides evidence of general antagonism of NKA. In general, the Compounds of the invention which were tested demonstrated statistically significant activity in Test A with a $K_i$ of 1 μM or much less. For example, the compound described in Example 2 was typically found to have a $K_i$ of 34 nM. In Test B, a $pK_B$ of 5 or greater was typically measured for a Compound of the invention. For example, a $pK_B$ of 6.6 was measured for the compound described in Example 3. It should be noted that there may not always be a direct correlation between the activities of Compounds measured as $K_i$ values in Test A and the values measured in other assays, such as the $pK_B$ measured in Test B.

As discussed above, a compound of formula I or a pharmaceutically acceptable salt thereof possesses NKA antagonist properties. Accordingly, it antagonizes at least one of the actions of NKA which are known to include bronchoconstriction, increased microvascular permeability, vasodilation and activation of mast cells. Accordingly, one feature of the invention is the use of a compound of formula I or a pharmaceutically acceptable salt thereof in the treatment of a disease in a human or other mammal in need thereof in which NKA is implicated and antagonism of its action is desired, such as for example the treatment of asthma or a related disorder. In addition, another feature of the invention is provided by the use of a compound of formula I or a salt thereof as a pharmacological standard for the development and standardization of new disease models or assays for use in developing new therapeutic agents for treating the diseases in which NKA is implicated or for assays for their diagnosis.

When used in the treatment of such a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (° C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; reversed phase chromatography means chromatography over octadecylsilane (ODS) coated support having a particle diameter of 32–74μ, known as "PREP-40-ODS" (Art 731740-100 from Bodman Chemicals, Aston, Pa., USA); thin layer chromatography (TLC) was carried out on silica gel plates; radial chromatography refers to chromatography on circular thin layer silica gel plates (Analtech) on a Harrison Research Model 8924 Chromatotron.

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; for AB spectra the directly observed shifts are reported; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the electron impact (EI) mode using a direct exposure probe; where indicated ionization was effected by chemical ionization (CI) or fast atom bombardment (FAB); values for m/z are given; generally, only ions which indicate the parent mass are reported.

EXAMPLE 1

2-[2-(3,4-Dichlorophenyl)-4-(4-hydroxy-4-phenylpiperidino)butyroyl]-1-phenylimidazole Hydrochloride A solution of n-butyl lithium (0.91 mL of a 2.44M solution in hexanes) in tetrahydrofuran (5 mL) was cooled to −78° C. and treated dropwise with a solution of 1-phenylimidazole (0.320 g) in tetrahydrofuran (2 mL). Upon complete addition, the resulting yellow solution was stirred at −78° C. for 30 minutes, then was treated dropwise with a solution of N-methoxy-N-methyl-2-[(3,4-dichlorophenyl)-4-(4-hydroxy-4-phenylpiperidino)] butyramide (0.50 g) in tetrahydrofuran (5 mL). The resulting mixture was allowed to warm to room temperature and stirred for 16 hours. The reaction was quenched by addition of saturated aqueous ammonium chloride and extracted with dichloromethane. The organic extract was washed sequentially with saturated aqueous ammonium chloride and brine, dried, filtered and evaporated to leave an orange oil. Purification by chromatography (65:35:10 dichloromethane:acetone:methanol) afforded the pure ketone (0.107 g), which was converted to the hydrochloride salt by treatment with gaseous hydrogen chloride in diethyl ether. The hydrochloride salt was prepared as a white powder; mp 128°–131° C.; NMR (CD$_3$OD): 7.59 (d,1), 7.59–7.27 (m,12), 7.21 (m,2), 5.13 (t,1), 3.44 (m,4), 3.15–2.95 (m,2), 2.60 (m,1), 2.24 (m,3), 1.95 (m,2); MS: m/z=536((M+H), $^{37}$Cl), 534((M+H), $^{35}$Cl). Analysis for C$_{30}$H$_{29}$Cl$_2$N$_3$O$_2$·1.0 HCl·0.5 H$_2$O: Calculated: C, 62.13; H; 5.39; N, 7.25; Found: C, 62.05; H, 5.10; N, 7.22.

The starting material 2-(3,4-Dichlorophenyl)-4-(4-hydroxy-4-phenylpiperidino)-N-methoxy-N-methylbutyramide was prepared as follows.

a. Methyl 2-(3,4-dichlorophenyl)-4-pentenoate. A solution of diisopropylamine (12.75 g) in tetrahydrofuran was cooled to −10° C. and was treated dropwise with a solution of n-butyllithium in hexanes (50 mL of a 2.44M solution). The resulting solution was cooled to −78° C. and was treated dropwise with methyl 3,4-dichlorophenylacetate (25.0 g) to afford a deep yellow solution. To this solution was added 1,3-dimethyl-3,4,5,6-tetrahydro-2(1H)pyrimidinone (16.15 g) followed by allyl bromide (15.24 g). The reaction mixture was allowed to warm to room temperature, was quenched by addition of saturated aqueous ammonium chloride solution and extracted with ethyl acetate. The organic extracts were washed (saturated aqueous ammonium chloride, brine), dried, and evaporated to leave an amber oil. Purification by fractional distillation afforded the pentoate as a clear liquid (23.08 g); (bp 125°–130° C., 1.1 Pa); NMR: 7.41 (d,1), 7.39 (d,1), 7.15 (dd,1), 5.65 (m,1), 5.10–5.00 (m,3), 3.67 (s,3), 3.59 (m,1), 2.77(m,1), 2.48 (m,1).

b. 2-(3,4-Dichlorphenyl)-4-pentenoic acid. A solution of methyl 2-(3,4-dichlorophenyl)-4-pentenoate (5.0 g) in methanol (100 mL) and tetrahydrofuran (100 mL) was treated with a solution of lithium hydroxide monohydrate (4.05 g) in water (100 mL). The reaction was stirred for 18 hours, then was evaporated, and the residue was dissolved in water. The solution was acidified to pH ca. 2 by addition of 1N hydrochloric acid and extracted with dichloromethane. The organic extracts were washed with brine, combined, dried, filtered and evaporated to yield the acid as a colorless syrup (4.61 g); NMR: 7.42 (d,1), 7.40 (d,1), 7.12 (dd,1), 5.66 (m,1), 5.12–5.03 (m,2), 3.61 (t,1), 2.78 (m,1), 2.50 (m,1); MS: m/z=247 ((M+H), $^{37}$Cl), 245 ((M+H), $^{35}$Cl).

c. 2-(3,4-Dichlorophenyl)-N-methoxy-N-methyl-4-pentenamide. A solution of N,O-dimethylhydroxylamine hydrochloride (2.18 g) in dichloromethane (50 mL) was treated with triethylamine (5.65 g), 2-(3,4-dichlorophenyl)-4-pentenoic acid (4.56 g), 1-(3-dimethylaminopropyl)-3-ethylcarbodiimide hydrochloride (7.11 g) and 4-dimethylaminopyridine (0.227 g). The resulting mixture was stirred for 18 hours, was diluted with ethyl acetate and washed (water, 2N hydrochloric acid, saturated aqueous sodium bicarbonate and brine). The organic extract was dried, and evaporated to leave a yellow syrup (5.31 g). Chromatography, eluting with dichloromethane:methanol (95:5), afforded the amide as a colorless syrup (4.18 g); NMR: 7.46–7.16 (m,3), 5.68 (m,1), 5.09–4.98 (m,2), 4.03 (broad t,1), 3.55 (s,3), 3.16 (s,3), 2.78 (m,1), 2.42 (m,1); MS: m/z=290 ((M+H), $^{37}$Cl), 288 ((M+H), $^{35}$Cl).

d. 2-(3,4-Dichlorophenyl)-N-methoxy-N-methyl-4-oxobutyramide. A solution of 2-(3,4-dichlorophenyl)-N-methoxy-N-methyl-4-pentenamide (4.00 g) in diethyl ether (40 mL), water (40 mL) and tetrahydrofuran (13 mL) was treated with osmium tetraoxide (1.05 mL of a 0.2M solution in water) and sodium periodate (6.53 g), in portions over 20 minutes. The mixture was stirred vigorously for 1.5 hours, a white precipitate of sodium iodate formed. The mixture was diluted with water and extracted with ethyl acetate. The organic extract was washed (water, brine), dried, filtered through diatomaceous earth and silica gel and evaporated to leave the aldehyde as a dark amber syrup which was not purified further; NMR: 9.77 (s,1), 7.41–7.13 (m,3), 4.50 (m,1), 3.65 (s,3), 3.49 (dd,1), 2.69 (dd,1); MS: m/z=292( (M+H), $^{37}$Cl), 290 ((M+H), $^{35}$Cl).

e. 2-(3,4-Dichlorophenyl)-4-(4-hydroxy-4-phenylpiperidino)-N-methoxy-N-methylbutyramide. A solution of 2-(3,4-dichlorophenyl)-N-methoxy-N-methyl-4-oxobutyramide (3.51 g), 4-hydroxy-4-phenylpiperidine (2.57 g) and glacial acetic acid (3 mL) in methanol (100 mL) was cooled to 0° C. and treated with sodium cyanoborohydride (1.06 g), added in three equal portions. The reaction was allowed to warm to room temperature and was stirred for 18 hours. The solvent was evaporated and the residue was dissolved in dichloromethane, washed (1N aqueous sodium hydroxide, brine), dried, and evaporated to leave a brown foam (4.41 g). Chromatography, eluting with dichloromethane:methanol:ammonium hydroxide (950:50:1), afforded the alcohol as a pale amber syrup (2.76 g); NMR (CD$_3$OD): 7.54–7.19 (m,8), 4.19 (broad,1), 3.65 (s,3), 2.80 (broad s,3), 2.78 (m,2), 2.54–2.29 (m,5), 2.11 (m,2), 1.91 (m,1), 1.73 (m,2); MS: m/z=453((M+H), $^{37}$Cl), 451 ((M+H), $^{35}$Cl). A portion of the product was treated with ethereal hydrogen chloride to afford the hydrochloride salt of the piperidinobutyramide as a white powder, mp 108°–110° C.; Analysis for C$_{23}$H$_{28}$Cl$_2$N$_2$O$_3$·1.00 HCl·0.50 H$_2$O: Calculated: C, 55.60; H, 6.09; N, 5.64; Found: C, 55.60; H, 6.02; N, 5.59.

EXAMPLE 2

2-[(1RS,2RS)-2-(3,4-Dichlorophenyl)-1-hydroxy-4-(4-hydroxy-4-phenylpiperidino)butyl]-1-phenylimidazole Hydrochloride A solution of 2-[(3,4-dichlorophenyl)-4-(4-hydroxy-4-phenylpiperidino)butyroyl]-1-phenylimidazole (0.191 g), prepared as described in Example 1, in methanol (5 mL) was cooled to 0° C. and treated with sodium borohydride (15 mg). The reaction mixture was allowed to warm to room temperature and was stirred for 4 hours. The solvent was evaporated and the residue was dissolved in ethyl acetate, washed (water, brine) dried, filtered and evaporated to leave a white foam (0.167 g). Chromatography, eluting with dichloromethane:methanol:ammonium hydroxide (930:70:1), gave the title compound as a white foam (0.121 g). This product was treated with gaseous hydrogen chloride in diethyl ether to afford the hydrochloride salt as a white powder (0.115 g); mp 161°–163.5° C.; NMR (CD$_3$OD): 7.60–7.24 (14), 6.93 (d,1), 5.24 (broad s,1), 3.44–3.20 (m,4), 3.19 (m,1), 3.02 (m,1), 2.85 (m,1), 2.40–2.19 (m,4), 1.95 (m,2); MS: m/z=538((M+H), $^{35}$Cl), 536((M+H), $^{35}$Cl). Analysis for C$_{30}$H$_{31}$Cl$_2$N$_3$O$_2$·1.00 HCl·2.00 H$_2$O: Calculated: C, 59.17; H, 5.96; N, 6.90; Found: C, 59.10; H, 5.90; N, 6.86.

EXAMPLE 3

4-[2-(3,4-Dichlorophenyl)-4-(4-hydroxy-4-phenylpiperidino)butyroyl]-3-phenyl-1H-pyrazole A solution of 4-(3,4-dichlorophenyl)-6-(4-hydroxy-4-phenylpiperidino)-1-phenyl-hex-1-yne-3-one (0.30 g) in diethyl ether (25 mL) was cooled to 0° C. and was treated with diazomethane (generated by the reaction of and ethereal solution of N-methyl-N-nitroso-p-toluenesulfonamide with ethanolic potassium hydroxide (*Anal. Chem.*, 45, 2302, 1973)). The resulting mixture was allowed to warm to room temperature and stirred for 3 days. The solvent was evaporated. Radial chromatography, eluting with dichloromethane:methanol (gradient 97.5:2.5, 95:5), afforded the title compound (50 mg) as a white powder; mp 112°–114° C.; NMR: 8.13 (s,1), 7.56–7.26 (m,12), 7.08 (d,1), 4.33 (broad s,1), 2.68 (m,2), 2.37 (m,3), 2.05 (broad s,1), 1.86 (broad s,1), 1.73–1.43 (m,5); MS: m/z=534(M+l). Analysis for C$_{30}$H$_{29}$Cl$_2$N$_3$O$_2$·0.75 H$_2$O: Calculated: C, 65.75; H, 5.61; N, 7.67; Found: C, 65.71; H, 5.60; N, 7.83.

The starting material ketone was prepared as follows:

a. 4-(3,4-Dichlorophenyl)-6-(4-hydroxy-4-phenylpiperidino)-1-phenylhex-1-yne-3-one. A solution of phenylacetylene (0.454 g) in tetrahydrofuran (8 mL) was cooled to −20° C. and treated with a solution of n-butyllithium in hexanes (1.91 mL of a 2.44M solution). The resulting dark mixture was stirred at −20° C. for 15 minutes, then was cooled to −78° C. and treated with a solution of 2-(3,4-dichlorophenyl)-4-(4-hydroxy-4-phenylpiperidino)-N-methoxy-N-methylbutyramide (1.00 g), prepared as described in Example 1.e., in tetrahydrofuran (10 mL). The mixture was stirred at −78° C. for 2 hours, was warmed to −30° C. and quenched with saturated aqueous ammonium chloride solution. The mixture was extracted with ethyl acetate. The organic extracts were washed (brine) dried, and evaporated to leave a pale green syrup. Chromatography, eluting with hexane:ethyl acetate (20:80), afforded the ketone as a pale amber foam (0.703 g). A portion of this product was converted to the corresponding hydrochloride salt for characterization by treatment with ethereal hydrogen chloride to give a white powder; mp 99°−101° C.; Analysis for $C_{29}H_{27}Cl_2NO_2 \cdot 0.5\ H_2O \cdot 1.0\ HCl$: Calculated: C, 64.75; H, 5.43; N, 2.60; Found: C, 64.73; H, 5.32; N, 2.56.

EXAMPLE 4

3-[2-(3,4-Dichlorophenyl)-4-(4-hydroxy-4-phenylpiperidino)butyroyl]-4-phenyl-1H-pyrazole The crude material isolated in Example 3, was purified by radial chromatography to afford the title compound as a white powder; mp 108°−110° C.; NMR: 7.63 (s,1), 7.50−7.25 (m,12), 7.08 (broad d,1), 4.71 (broad s,1), 2.76 (m,2), 2.54−2.44 (m,4), 2.15−1.72 (m,3), 1.53 (m,2), 1.43 (broad s,1); MS: m/z=534 (M+1). Analysis for $C_{30}H_{29}Cl_2N_3O_2 \cdot 0.5\ H_2O$: Calculated: C, 66.30; H, 5.56; N, 7.73; Found: C, 66.31; H, 5.55; N, 7.74.

EXAMPLE 5

4-[(1RS,2RS)-2-(3,4-Dichlorophenyl)-1-hydroxy-4-(4-hydroxy-4-phenylpiperidino)butyl]-3-phenyl-1H-pyrazole A solution of 4-[2-(3,4-dichlorophenyl)-4-(4-hydroxy-4-phenylpiperidino)butyroyl]-3-phenyl-1H-pyrazole (95 mg), prepared as described in Example 3, in methanol (3 mL) was cooled to 0° C. and treated with sodium borohydride (9 mg). The mixture was allowed to warm to room temperature and was stirred for 1 hour. The solvent was evaporated and the residue partitioned between water and ethyl acetate. The organic extracts were washed (water, brine) combined, dried, and evaporated to afford a white foam. Trituration with ether:hexane (1:2) afforded the title compound as a white solid (62 mg); mp 133°−135° C.; NMR: 7.57−7.23 (m,13), 7.03 (m,1), 5.11 (d,1), 3.04 (m,1), 2.86 (m,2), 2.51 (m,2), 2.37 (m,2), 2.23 (m,2), 1.94 (m,1), 1.81−1.60 (m,3); MS: m/z=536(M+1). Analysis for $C_{30}H_{31}Cl_2N_3O_2 \cdot 1.00\ H_2O$: Calculated: C, 64.98; H, 5.82; N, 7.83; Found: C, 64.91; H, 5.74; N, 7.53.

EXAMPLE 6

3-[(1RS,2RS)-2-(3,4-Dichlorophenyl)-1-hydroxy-4-(4-hydroxy-4-phenylpiperidino)butyl]-4-phenyl-1H-pyrazole By a procedure similar to that described in Example 5, except using 5-[2-(3,4-dichlorophenyl)-4-(4-hydroxy-4-phenylpiperidino)butyroyl]-4-phenyl-1H-pyrazole, the title compound was obtained as a white powder; mp 122°−124° C.; NMR: 7.52 (m,2), 7.43−7.18 (m,8), 7.10 (m,2), 6.88 (d,1), 5.40 (m,1), 3.10 (m,1), 2.95 (m,2), 2.70−2.48 (broad m,2), 2.43 (m,2), 2.24 (m,2), 1.98−1.78 (broad m,3), 1.55 (m,1); MS: m/z=536(M+1). Analysis for $C_{30}H_{31}Cl_2N_3O_2 \cdot 0.25\ H_2O$: Calculated: C, 66.60; H, 5.87; N, 7.77; Found: C, 66.39; H, 5.86; N, 7.67.

EXAMPLE 7

5-[(1S,2S)-1-acetoxy-2-(3,4-dichlorophenyl)-4-(4-hydroxy-4-phenylpiperidino)butyl]-1-phenylpyrazole Citrate Salt A solution of 5-[(1S,2S)-1-acetoxy-2-(3,4-dichlorophenyl)-4-oxobutyl]-1-phenylpyrazole (89 mg) and 4-hydroxy-4-phenylpiperdine (41 mg) in methanol was adjusted to pH=5.5 by addition of glacial acetic acid. The resulting mixture was treated with sodium cyanoborohydride (15 mg) and stirred for 2 hours. The solvent was evaporated and the residue was partitioned between 1N aqueous sodium hydroxide and dichloromethane. The organic extracts were washed (brine) dried, filtered and evaporated to leave an off-white foam (110 mg). Purification by chromatography (100:2.5:0.1 chloroform/methanol/ammonium hydroxide) afforded the title compound (77.5 mg) as a white foam. The citrate salt was prepared by treatment of this material with citric acid in diethyl ether/ methanol (10:1). mp 112°−117° C.; NMR: 7.66 (d, 1, J=1.7), 7.50−7.22 (m,12), 7.04 (dd, 1, J=1.7, 8.4), 6.41 (d, 1, J=1.7), 6.03 (d, 1, J=6.6), 5.18 (broad, 1), 3.34 (broad m), 2.60 (q, J=14.0) Hz, citrate), 2.00 (broad m), 1.94 (s,3), 1.71 (m,2); MS: m/z=606 ((M+1+28), 13%), 582 (12), 581 (15), 580 ((M+1), 37Cl, 58), 579 (24), 578 ((M+1), 35Cl, 86), 562 (25), 560 (36), 520 (38), 518 (54). Analysis for $C_{32}H_{33}Cl_2N_3O_3 \cdot 1.00\ C_6H_8O_7 \cdot 0.7\ H_2O$: Calculated C, 58.27; H, 5.46; N, 5.36; Found: C, 58.36; H, 5.60; N, 5.23.

The starting material 5-[(1S,2S)-1-Acetoxy-2-(3,4-dichlorophenyl)-4-oxobutyl]-1-phenylpyrazole was prepared as follows:

a. (S)-2-(3,4-Dichlorophenyl)-4-pentenoic acid. A solution of 2-(3,4-dichlorophenyl)-4-pentenoic acid (24.2 g), in ethyl acetate (100 mL) was treated with a solution of (S)-(α)-methylbenzylamine (12.1 g) in ethyl acetate (100 mL). The resulting crystalline enriched diastereomeric salt was isolated by filtration. The enriched diastereomeric salt was recrystallized five times from ethyl acetate (150 mL, 150 mL, 100 mL, 100 mL, 75 mL) to afford highly enriched salt (6.13 g, 17%, diastereomeric ratio 95:5 as determined by HPLC). This salt was dissolved in water (25 mL) and the resulting solution was acidified to pH 2–3 with 2.5N hydrochloric acid and then extracted with ethyl acetate (2×100 mL). The organic extracts were washed (water) dried, filtered and evaporated to afford the optically enriched acid as a clear oil (3.87 g); $[\alpha]_D$=+54.1 (C=3.43, methanol).

HPLC analysis: Column Ultron Ovomucoid (ES-OVM) 15 cm×6 mm; Eluent: 30% acetonitrile/70% aqueous $KH_2PO_4$ buffer (10 mM) adjusted to pH 5.5 with 1M potassium hydroxide; Flow 1 mL/min; Wavelength: 230 nm; Retention times: (S) enantiomer 4.11 min., (R) enantiomer 5.91 min.

b. (S)-2-(3,4-Dichlorophenyl)-N-methoxy-N-methyl-4-pentenamide. Using a procedure similar to that described in Example 1.c., except using (S)-2-(3,4-dichlorophenyl)-4-pentenoic acid, the amide was prepared as a pale amber oil (75%); NMR: 7.43 (d,1), 7.37 (d, 1), 7.17 (dd, 1), 5.68 (m,1), 5.02 (m,2), 4.03 (broad t,1), 2.77 (m,1), 2.40 (m,1).

c. 5-((S)-2-(3,4-Dichlorophenyl)-4-pentenoyl)-1-phenylpyrazole. Lanthanum (III) chloride heptahydrate (830 mg) was dried in vacuo (140° C.; 0.2 torr) for 2 hours, was cooled to room temperature under nitrogen and suspended in dry tetrahydrofuran (5 mL). The suspension was stirred for 24 hours at room temperature. In a separate flask, a solution of 1-phenylpyrazole in tetrahydrofuran (4 mL) was cooled to −30° C. and treated dropwise with n-butyllithium (0.84 mL of a 2.48M solution in hexanes). The resulting tan suspension was warmed to room temperature and was stirred for 0.5 hours. The lanthanum chloride/tetrahydrofuran suspension was cooled to −78° C. and treated with the 5-lithiol-1-phenylpyrazole solution, transferred via cannula. The resulting suspension was stirred at −78° C. for 0.25 hours, and was treated with a solution of (S)-2-(3,4- dichlorophenyl)-N-methoxy-N-methyl-4-pentenamide (450 mg) in tetrahydrofuran (5 mL). The reaction mixture was stirred at −78° C. for 1 hour, was slowly warmed to 0° C. and quenched by addition of aqueous acetic acid (5 mL, 1%). The mixture was poured into aqueous acetic acid (50 mL, 1%) and extracted with ethyl acetate). The organic extracts were washed (brine) dried, and evaporated to leave an amber oil (640 mg). This oil was purified by radial chromatography (2 mm SiO2, 8:1 hexane/ethyl acetate, 4:1 hexane/ethyl acetate, 1:1 hexane/ethyl acetate) to afford the title compound as a colorless oil (310 mg); NMR: 7.66 (d,1), 7.47–7.21 (m,7), 7.11 (dd,1), 6.96 (d,1), 5.65 (m,1), 5.02 (m,2), 4.30 (t,1), 2.83 (m,1), 2.46 (m,1).

5-[(1S,2S)-2-(3,4-Dichlorophenyl)-1-hydroxy-4-pentenyl]-1-phenylpyrazole. A solution of 5-((S)-2-(3,4-dichlorophenyl)-4-pentenoyl)-1-phenylpyrazole (130 mg) in methanol (5 mL) was cooled to 0° C. and treated with sodium borohydride (20 mg). The resulting mixture was stirred for 0.25 hours, was evaporated. The residue was partitioned between water and ethyl acetate (2×). The organic extracts were washed (brine) combined, filtered and evaporated to leave the alcohol as a white foam (118 mg). NMR showed this material to be about 95% the (1S,2S) diastereomer; NMR: 7.61 (d,1), 7.53–7.15 (m,7), 6.90 (dd, 1), 6.28 (d,1), 5.36 (m,1), 4.85 (m,3), 2.90 (m,1), 2.38–2.04 (m,2). Analysis of this material by HPLC on a chiral stationary phase showed it to have the following composition: 86.5% (1S,2S), retention time=18.1 min 7.5% (1R,2S), retention time=13.7 min 5.4% (1R,2R), retention time=16.8 min 0.5% (1S, 2R). retention time=15.3 min Analysis conditions: Column: 4.6 mm×25 cm Chiralcel OD Eluent: 90:10 hexane/isopropanol Flow rate: 0.8 mL/min Detection: uv @215 nM, 0.2 AUFS e. 5-[(1S,2S)-1-Acetoxy-2-(3,4-dichlorophenyl)-4-pentenyl]-1-phenylpyrazole. A solution of 5-[(1S,2S)-2-(3, 4-dichlorophenyl)-1-hydroxy-4-pentenyl]-1-phenylpyrazole (110 mg) in dichloromethane (2 mL) was treated with triethylamine (35 mg), acetic anhydride (36 mg) and 4-N, N-dimethylaminopyridine (3 mg). The resulting mixture was stirred at room temperature for 0.5h, was poured into 1N hydrochloric acid (10 mL) and extracted with ethyl acetate (2×). The organic extracts were washed with 10% (w/v) aqueous sodium bicarbonate and brined, combined, dried, filtered and evaporated to give the acetoxy compound as a clear oil (92 mg), which was used without purification; MS: m/z=417 ((M+1), 37Cl), 415((M+1), 35Cl).

f. 5-[(1S,2S)-1-Acetoxy-2-(3,4-dichlorophenyl)-4-oxobutyl]-1-phenylpyrazole. A solution of 5-[(1S,2S)-1-acetoxy-2-(3,4-dichlorophenyl)-4-pentenyl]-1-phenylpyrazole (90 mg) in tetrahydrofuran (1 mL), diethyl ether (2 mL) and water (2 mL) was treated with osmium tetraoxide (0.07 mL of a 0.2M solution in water) and sodium periodate (100 mg). The resulting biphasic mixture was stirred vigorously at room temperature for 4 hours. The mixture was diluted with water and extracted with ethyl acetate. The organic extracts were washed (brine), dried, and evaporated to afford the title compound as a pale amber foam (89 mg). This material was used immediately; NMR: 9.57 (s,1), 7.62 (d,1), 7.45–7.21 (m,6), 6.99 (d,1), 6.72 (dd,1), 6.31 (d,1), 6.15 (d,1), 3.63 (m,1), 2.77 (m,2), 2.03 (s,3); MS: m/z=419((M+1), 37Cl), 417((M+1), 35Cl).

EXAMPLE 8

4-[(1RS,2RS)-2-(3,4-Dichlorophenyl)-1-hydroxy-4-(4-hydroxy-4-phenylpiperidino)butyl]-5-phenyl-(1H)-1,2,3-triazole Bishydrochloride Using a procedure similar to that described in Example 2, except using 5-[2-(3,4-dichlorophenyl)-4-(4-hydroxy-4-phenylpiperidino)butyroyl]-4-phenyl-(1H)-1,2,3-triazole, the title hydrochloride salt was obtained as a white powder; mp 153°–155° C.; NFER (d4 MeOH): 7.50–7.20 (broad m,12), 6.99 (m,1), 5.24 (d,1), 5.07 (d,1), 3.52–3.20 (broad m,6), 2.91 (m,1), 2.32–2.02 (broad m,4), 1.96 (m,2); MS: m/z=539 ((M+1), 37Cl), 537 ((M+1), 35Cl). Analysis for $C_{29}H_{30}Cl_2N_4O_2 \cdot 2.00$ HCl·2.5 $H_2O$: Calculated C, 53.14; H, 5.68; N, 8.54; Found: C, 53.14; H, 5.40; N, 8.52. Found C: 53.14; H: 5.40; N: 8.52

The starting material 5-[2-(3,4-Dichlorophenyl)-4-(4-hydroxy-4-phenyl-piperidino)butyroyl]-4-phenyl-(1H)-1,2, 3-triazole was prepared as follows:

a. 4-(3,4-Dichlorophenyl)-6-(4-hydroxy-4-phenylpiperidino)-1-phenyl-1-hexyn-3-one. A solution of phenylacetylene (454 mg) in tetrahydrofuran (8 mL) was cooled to −20° C. and was treated with n-butyllithium (1.91 mL of a 2.44M solution in hexanes). This mixture was stirred at −20° C. for 0.25 hours, was cooled to −78° C. and was treated with a solution of 2-(3,4-dichlorophenyl)-4-(4-hydroxy-4-phenylpiperidino)-N-methoxy-N-methylbutyramide (1.00 g), prepared as described in Example 1.e., in tetrahydrofuran (10 mL). The reaction mixture was stirred at −78° C. for 2 hours, warmed to −30° C., quenched by addition of saturated aqueous ammonium chloride and extracted with ethyl acetate. The organic extracts were washed (saturated aqueous ammonium chloride, brine), dried, and evaporated to leave a green syrup (1.12 g). Chromatography, eluting with hexane:ethyl acetate (80:20) afforded the acetylene (703 mg) as a tan foam; A sample (100 mg) of this product was converted to the hydrochloride salt with hydrogen chloride (g) in diethyl ether, and isolated as a tan powder; mp 99°–100° C.; NMR (d4-MeOH): 7.65–7.25 (m,13), 4.11 (5,1), 3.64–3.31 (m,5), 3.07 (m,1), 2.68 (m,1), 2.30 (m,3), 1.98 (m,2); MS: m/z=494 ((M+1), 37Cl), 492 ((M+1), 35Cl). Analysis for $C_{29}H_{27}Cl_2NO_2 \cdot 1.0$ HCl·0.5 $H_2O$: Calculated C, 64.75; H, 5.43; N, 2.60; Found: C, 64.72; H, 5.32; N, 2.56.

b. 5-[2-(3,4-Dichlorophenyl)-4-(4-hydroxy-4-phenylpiperidino)butyroyl]-4-phenyl-(1H)-1,2,3-triazole. A suspension of sodium azide (38 mg) in N,N-dimethylformamide (1 mL) was treated dropwise with a solution of 4-(3,4-dichlorophenyl)-6-(4-hydroxy-4-phenyl-piperidino)-1-phenyl-1-hexyn-3-one (287 mg) in N,N-dimethylformamide (4 mL). The reaction mixture was warmed to 35° C. and was stirred for 3 hours. The reaction was quenched by addition of water and extracted with ethyl acetate. The organic extracts were combined, washed (water, brine) and evaporated to leave an orange syrup. The syrup was triturated with dichloromethane to afford the triazole as a pale tan powder (260 mg, 83%). NMR (d6-DMSO): 7.89 (m,2), 7.63 (d, J=1.8 Hz, 1), 7.57 (d, J=8.3 Hz, 1), 7.45–7.17 (m,9), 5.24 (t, J=7.3 Hz, 1H, H-C(2')), 4.91 (broad s, 1H, O), 2.86–2.50 (m,7), 1.95–1.49 (m,5H).

EXAMPLE 9

5-[(1RS,2SR)-1-Acetoxy-2-(3,4-dichlorophenyl)-4-(4-hydroxy-4-phenylpiperidino)butyl]-1-phenylpyrazole Citrate Salt Using a procedure similar to that described in Example 7, except using 5-[(1RS,2SR)-1-acetoxy-2-(3,4-dichlorophenyl)-4-oxobutyl]-1-phenylpyrazole as the aldehyde component in the reductive alkylation, the citrate salt of the title compound was prepared as a white powder (43%); mp 93°–95° C.; NMR (d4-MeOH): 7.60 (d,1), 7.50–7.32 (m,6), 7.24 (m,3), 7.15 (m,2), 7.10 (s,1), 6.73

(d,1), 6.60 (d,1), 5.88 (d,1), 3.36 (m,2), 3.20 (m,2), 3.07 (m,1), 2.86–2.71 (q, citrate), 2.45 (m,1), 2.32 (m,2), 2.18 (s,3), 1.86 (broad d, 2); MS: m/z=580((M+1), 37Cl), 578 ((M+1), 35Cl). Analysis for $C_{32}H_{32}Cl_2N_3O_3 \cdot 1.0$ $C_6H_8O_7 \cdot 1.5\ H_2O$: Calculated C, 57.22; H, 5.56; N, 5.27; Found: C, 57.22; H, 5.41; N, 4.91.

The starting material aldehyde was prepared as follows.

a. 2-(3,4-Dichlorophenyl)-4-pentenol. A suspension of lithium aluminum hydride (1.65 g) in diethyl ether (25 mL) was cooled to 0° C. and was treated dropwise with a solution of methyl 2-(3,4-dichlorophenyl)-4-pentenoate (7.50 g), prepared as described in Example 1.a., in diethyl ether (75 mL). The reaction mixture was stirred at 0° C. for 2 hours, was warmed to room temperature and stirred for 1 hour. The mixture was cooled to 0° C. and quenched by addition of saturated aqueous sodium sulfate solution (10 mL). The mixture was partitioned between water and diethyl ether (3×). The organic extracts were combined, washed (water, brine) dried, and evaporated to afford the title compound as a clear oil (6.69 g, 94%); NMR: 7.40 (d,1), 7.32 (d,1), 7.05 (dd,1), 5.65 (m,1), 4.99 (m,1), 3.87–3.71 (m,3), 2.84 (m,1), 2.51–2.31 (broad m,2).

b. 2-(3,4-Dichlorophenyl)-4-pentenal. A solution of oxalyl chloride (6.85 g) in dichloromethane (35 mL) was cooled to −78° C. and was treated dropwise with dimethyl sulfoxide (4.64 g) in dichloromethane (10 mL). The resulting solution was stirred at −78° C. for 0.5 hours, was treated with a solution of 2-(3,4-dichlorophenyl)-4-pentenol (6.24 g) in dichloromethane (50 mL). The reaction mixture was stirred at −78° C. for 2 hours, was treated with triethylamine (13.66 g). The mixture was allowed to warm to room temperature and was stirred for 1 hour. The mixture was diluted with dichloromethane (250 mL), washed (water, brine), dried, and evaporated to afford the aldehyde as a pale yellow oil (6.35 g) which was used without purification in the next step; MS: m/z=231((M+1), 37Cl), 229((M+1), 35Cl).

c. 5-((1RS,2SR)-2-(3,4-Dichlorophenyl)-1-hydroxy-4-pentenyl)-1-phenylpyrazole. Cerium (III) chloride heptahydrate (9.70 g) was dried at 140° C. at 0.2 torr for 2 hours, and was cooled to room temperature and suspended in tetrahydrofuran (100 mL). The suspension was stirred at room temperature for 2 hours. In a separate flask, a solution of n-butyllithium (9.14 mL of a 2.44M solution in hexanes) in tetrahydrofuran (40 mL) was cooled to −30° C. and was treated with a solution of 1-phenylpyrazole (3.22 g) in tetrahydrofuran (10 mL). The resulting orange solution was warmed to room temperature, stirred for 0.5 hours, and added to the cooled (−78° C.) cerium chloride/tetrahydrofuran suspension. The resulting orange suspension was stirred at −78° C. for 0.5 hours and treated with a solution of 2-(3,4-dichlorophenyl)-4-pentenal (4.26 g) in tetrahydrofuran (30 mL). The reaction mixture was allowed to warm to 0° C., was stirred at 0° C. for 1 hour and quenched by addition of aqueous acetic acid (1%). The mixture was poured into aqueous acetic acid (100 mL, 1%) and extracted with ethyl acetate. The organic extract was washed (aqueous acetic acid (1%), brine), dried, and evaporated to leave an orange oil (8.45 g). Chromatography, eluting with hexane:ethyl acetate (80:20), afforded the title compound (2.35 g) as a pale amber oil, along with fractions containing the title compound mixed with the (1RS,2RS) diastereomer (2.20 g). Further purification of these mixed fractions by radial chromatography (4 mm SiO2, 97:3 dichloromethane/methanol) afforded additional (1RS,2SR) compound (0.22 g) as a pale amber oil; NMR: 7.54 (d,1), 7.49–7.15 (m,6), 6.86 (d,1), 6.62 (dd,1), 6.27 (d,1), 5.45 (m,1), 4.93–4.81 (m,3), 2.91 (m,1), 2.71 (m,1), 2.33 (m,1).

d. 5-((1RS,2SR)-1-Acetoxy-2-(3,4-dichlorophenyl)-4-pentenyl)-1-phenylpyrazole. Using a procedure similar to that described in Example 7.e., except using 5-((1RS,2SR)-2-(3,4-dichlorophenyl)-1-hydroxy-4-pentenyl)-1-phenylpyrazole, the title compound was prepared as a white foam (73%); NMR: 7.56 (d, 1), 7.46–7.02 (m,6), 6.75 (d,1), 6.48 (dd,1), 6.40 (d,1), 5.96 (d,1), 5.39 (m,1), 4.89 (m,2), 2.96 (m,1), 2.60 (m,1), 2.32 (m,1), 2.14 (s,3).

e. 5-[(1RS,2SR)-1-Acetoxy-2-(3,4-dichlorophenyl)-4-oxobutyl]-1-phenylpyrazole. Using a procedure similar to that described in Example 7.f., except using 5-((1RS,2SR)-1-acetoxy-2-(3,4-dichlorophenyl)-4-pentenyl)-1-phenylpyrazole, the aldehyde was prepared as a white foam (89%); MS: m/z=419((M+1), 37Cl), 417((M+1), 35Cl).

EXAMPLE 10

5-[(1RS,2SR)-2-(3,4-Dichlorophenyl)-1-hydroxy-4-(4-hydroxy-4-phenylpiperidino)butyl]-1-phenylpyrazole Citrate Salt A solution of 5-[(1RS,2SR)-1-Acetoxy-2-(3,4-dichlorophenyl)-4-(4-hydroxy-4-phenylpiperidino)butyl]-1-phenylpyrazole (150 mg), prepared as described in Example 9, in methanol (5 mL) was treated with a solution of lithium hydroxide monohydrate (22 mg) in water (0.6 mL). The resulting mixture was stirred at room temperature for 16 hours, was adjusted to pH=3 by addition of 1N hydrochloric acid. The solvents were evaporated and the residue was purified by chromatography, eluting with dichloromethane:methanol:ammonium hydroxide (95:5:0.1) to leave an off white foam (115 mg). This product was dissolved in diethyl ether (25 mL) and was treated with a solution of citric acid (0.5 N in methanol) to afford the title compound (98 mg) as a white powder; mp 127°–130° C.; NMR (d4-MeOH): 7.55–7.24 (broad m,11), 7.12 (d,1), 6.81(s,1), 6.60 (d,1), 6.39 (s,1), 4.84 (d,1), 3.06–2.83 (broad m,3), 2.78 (m,1), 2.53 (m,3), 2.39–2.18 (broad m,2), 2.10 (m,1), 1.85 (m,3); MS: m/z=538((M+1), 37Cl), 536((M+1), 35Cl). Analysis for $C_{30}H_{31}Cl_2N_3O2 \cdot 1.00\ C_6H_8O_7$: Calculated C, 59.34; H, 5.40; N, 5.77; Found: C, 59.70; H, 5.47; N, 5.83.

EXAMPLE 11

5-[(1RS,2SR)-1-Acetoxy-2-(3,4-dichlorophenyl)-4-(4-acetamido-4-phenylpiperidino)butyl]-1-phenylpyrazole Citrate Salt Using a procedure similar to that described in Example 7, except using 4-acetamido-4-phenylpiperidine as the piperidine component, and 5-[(1RS,2SR)-1-acetoxy-2-(3,4-dichlorophenyl)-4-oxobutyl]-1-phenylpyrazole as the aldehyde component, the title compound was prepared as the citrate salt (58%); mp 112°–115° C.; NMR (d4-MeOH): 8.19 (s,1), 7.61 (d,1), 7.44–7.36 (m,6), 7.25 (m,3), 7.12 (m,2), 7.00 (s,1), 6.74 (d,1), 6.62 (d,1), 5.90 (d,1), 3.34 (m,2), 3.19 (m,1), 2.89–2.73 (m,2), 2.89 (q,4), 2.64 (m,3), 2.45 (m,1), 2.19 (s,3), 2.38–2.08 (m,4), 1.98 (s,3); MS: m/z=621((M+1), 37Cl), 619((M+1), 35Cl). Analysis for $C_{34}H_{36}Cl_2N_4O_3 \cdot 1.25\ C_6H_8O_7 \cdot 1.0\ H_2O$: Calculated C, 56.78; H, 5.51; N, 6.38; Found C, 57.13; H, 5.55; N, 5.98.

The starting material 4-acetamido-4-phenylpiperidine was prepared as follows.

a. 4-Hydroxy-4-phenyl-1-trifluoroacetylpiperidine. To a suspension of 4-hydroxy-4-phenylpiperidine (20 g) in dichloromethane (100 mL) was added ethyl trifluoroacetate (14.8 mL). Acetonitrile (50 mL) was added as a co-solvent, and the solution was stirred overnight. The mixture was washed (aqueous sodium bicarbonate), and the separated organic phase was dried and evaporated to give the trifluoromethylacetyl compound as a yellow solid; MS: m/z=274 (M+1).

p b. 4-Azido-4-phenyl-1-trifluoroacetylpiperidine. To a suspension of sodium azide (9.5 g) in chloroform (100 mL) and trifluoroacetic acid (115 mL) cooled to 0° C. was added the above piperidine (20 g) in chloroform (100 mL) dropwise over a period of 1 hour. The mixture was allowed to warm to ambient temperature gradually and stirred overnight. After evaporating the chloroform and trifluoroacetic acid, the resulting mixture was diluted with aqueous sodium bicarbonate and extracted with dichloromethane. The organic extracts were dried and evaporated to give the azido piperidine as a viscous oil (20 g); NMR: 7.41 (m,5), 4.51 (m,1), 3.97 (m,1), 3.61 (m,1), 3.26 (m,1), 2.10 (m,4); MS: m/z=299(M+1).

c. 4-Amino-4-phenyl-1-trifluoroacetylpiperidine and N-[4-Phenyl-1-(2,2,2-trifluoroacetyl)piperidin-4-yl] acetamide. A solution of the above azide (15 g) and 20% palladium hydroxide on carbon (1.5 g) in ethanol (150 mL) was stirred overnight under 1 barr of hydrogen. The reaction mixture was filtered through diatomaceous earth and the filtrate was concentrated in vacuo. The resulting oil was dissolved in dichloromethane and extracted with dilute aqueous hydrochloric acid. The acidic aqueous phase was extracted two times with dichloromethane (discarded), neutralized with saturated aqueous sodium bicarbonate, and extracted with dichloromethane. The organic extracts were dried and evaporated to give the amine; NMR (CD$_3$OD): 7.34 (m,5), 3.17 (m,1), 3.04 (m,1), 2.64 (m,1), 2.15 (m,1).

d. 4-Acetamido-4-phenyl-1-trifluoroacetylpiperidine. To the above amine in dichloromethane (80 mL) was added acetic anhydride (1.6 mL) and triethylamine (2.5 mL). The mixture was stirred overnight, washed, (dilute hydrochloric acid, dilute aqueous sodium bicarbonate), dried and evaporated to give the acetamide as a white solid (13.0 g); NMR: 7.30 (m,5), 6.08 (s,1), 4.24 (m,1), 3.82 (m,1), 3.48 (m,1), 3.23 (m,1), 2.65 (m,1), 2.42 (m,1), 2.09 (m,2), 2.00 (s,3); MS: m/z=315(M+1).

e. 4-Acetamido-4-phenylpiperidine. To a solution of the above acetamide (13.0 g) in methanol (120 mL) was added lithium hydroxide monohydrate (5.2 g) in water (30 mL). After being stirred for 3 hours, the mixture was evaporated, diluted with water, and extracted with dichloromethane. The aqueous layer was saturated with sodium chloride and extracted with ethyl acetate. The combined organic extracts were dried and evaporated to give the deprotected piperidine as a white solid (2.5 g) by precipitation from acetonitrile; NMR (CD$_3$OD): 7.29 (m,5), 2.98 (m,4), 2.44 (m,2), 1.97 (m,5); NMR (CD$_3$OD/CF$_3$COOH): 7.31 (m,5), 3.28 (m,4), 2.68 (m,2), 2.18 (m,2), 2.02 (s,3); MS: m/z=219(M+1).

EXAMPLE 12

5-[(1RS,2SR)-2-(3,4-Dichlorophenyl)-1-hydroxy-4-(4-(N-acetylamino)-4-phenylpiperidino)butyl]-1-phenylpyrazole Using a procedure similar to that described in Example 10, except using 5-[(1RS,2SR)-1-acetoxy-2-(3,4-dichlorophenyl)-4-(4-acetamido-4-phenylpiperidino)butyl]-1-phenylpyrazole, the title compound was prepared as a white powder (54%); mp 115°–118° C.; NMR: 7.51 (s,1), 7.45–7.32 (broad m,6), 7.27 (m,4), 7.21 (d,1), 6.80 (s,1), 6.58 (d,1), 6.37 (s,1), 5.49 (s,1), 4.82 (d,1), 2.94 (m,2), 2.81 (m,1), 2.54–2.41 (broad m,5), 2.28 (broad m,3), 2.01 (broad s,4), 1.85 (m,1); MS: m/z=579((M+1), 37Cl), 577((M+1), 35Cl).

EXAMPLE 13

5-[(1RS,2SR)-1-Acetoxy-2-(3,4-dichlorophenyl)-4-(4-(1-ethyl-1-hydroxypropyl)piperidino)butyl]-1-phenylpyrazole Citrate Salt Using a procedure similar to that described in Example 7, except using 4-(1-ethyl-1-hydroxypropyl)piperidine, as the amine component, and 5-[(1RS,2SR)-1-acetoxy-2-(3,4-dichlorophenyl)-4-oxobutyl]-1-phenylpyrazole as the aldehyde component, the title compound was prepared as the citrate salt (53%); mp 76°–79° C.; NMR (d4-MeOH): 7.61 (d,1), 7.61–7.36 (m,3), 7.21 (d,1), 7.12 (m,2), 6.97 (s,1), 6.71 (d,1), 6.61 (d,), 5.89 (d, 1), 3.47 (m,2), 3.25 (m,1), 2.91–2.72 (m,4), 2.91 (m,4), 2.55–2.45 (broad m,2), 2.19 (s,3), 1.85 (broad s,2), 1.56 (broad s,3), 1.51 (m,4); MS: m/z=574 ((M+1), 37Cl), 572((M+1), 35Cl). Analysis for C$_{31}$H$_{39}$Cl$_2$N$_3$O$_3$·1.00 C6H8O7·1.5 H$_2$O; Calculated: C, 56.13; H, 6.37; N, 5.31; Found C, 56.44; H, 6.24; N, 4.94.

The starting material 4-(1-ethyl-1-hydroxypropyl) piperidine was prepared as follows:

a. Ethyl 1-(benzyloxycarbonyl)-4-piperidine carboxylate. A solution of ethyl 4-piperidine carboxylate (14.71 g) and triethylamine (12.04 g) in chloroform (200 mL) was cooled to 0° C. and treated dropwise with benzyl chloroformate (17.91 g). The resulting mixture was stirred at 0° C. for 1 hour, was allowed to warm to room temperature and was stirred for 12 hours. The mixture was washed (brine, 1N hydrochloric acid), dried, and evaporated to yield a pale yellow oil (26.4 g). Chromatography, eluting with dichloromethane:methanol (95:5) gave the benzyl compound as a colorless syrup (22.15 g); NMR: 7.35 (m,5, 5.07 (s,2), 4.06 (q,2), 3.91 (broad d,2), 2.95 (broad, 2), 2.53 (m,1), 1.82 (broad d,2), 1.41 (m,2), 1.18 (t,3).

b. 1-(Benzyloxycarbonyl)-4-(1-ethyl-1-hydroxypropyl) piperdine. A solution of ethyl magnesium chloride (10.7 mL of a 2M solution in tetrahydrofuran) in tetrahydrofuran (25 mL) was cooled to −60° C. and treated dropwise with a solution of ethyl 1-(benzyloxycarbonyl)-4-piperidine carboxylate (2.50 g) in tetrahydrofuran (10 mL). The resulting solution was stirred at −60° C. for 1 hour, was warmed to 0° C. for 1 hour, quenched by addition of 1N hydrochloric acid, diluted with water and extracted with ethyl acetate. The organic extracts were washed (brine, 1N hydrochloric acid), dried, and evaporated to afford the title compound as a colorless oil (2.49 g). This material was used without purification in the next step; NMR: 7.35 (m,5), 5.12 (s,2), 4.27 (m,2), 2.71 (broad, 2), 1.67–1.29 (m,10), 0.86 (t,6).

c. 4-(1-Ethyl-1-hydroxypropyl)piperidine. A solution of 1-(benzyloxycarbonyl)-4-(1-ethyl-1-hydroxypropyl) piperidine (2.44 g) in ethanol (50 mL) was hydrogenated over 10% palladium on carbon (100 mg, 3.45 bar) for 4 hours. The mixture was filtered and evaporated to afford the piperidine as a clear oil which solidified upon standing (1.37 g); NMR: 3.26 (broad d,2), 2.69 (m,2), 1.71 (broad d,2), 1.60–1.39 (m,7), 0.86 (t,6)

EXAMPLE 14

5-[(1RS,2SR)-2-(3,4-Dichlorophenyl)-1-hydroxy-4-(4-(1-ethyl-1-hydroxypropyl)piperidino)butyl]-1-phenylpyrazole Citrate Salt Using a procedure similar to that described in Example 10, except using 5-[(1RS,2SR)-1-acetoxy-2-(3,4-dichlorophenyl)-4-(4-(1-ethyl-1-hydroxypropyl)piperidino) butyl]-1-phenylpyrazole, the title compound was prepared as a white powder (54%); mp 80°–83° C.; NMR (d4-

MeOH): 7.57 (s 1), 7.47 (m,3), 7.22 (d,1), 7.08 (m,2), 7.01 (s,1), 6.78 (d,1), 6.60 (s,1), 4.75 (d,1), 3.50(m,2), 2.95 (m,3), 2.83–2.59 (broad m,4), 2.00 (broad s,1), 1.86 (broad s,2), 1.58 (broad s,2), 1.48(m,4), 0.85 (t,6); MS: m/z=532 ((M+1), 37Cl), 530((M+1), 35Cl). Analysis for $C_{29}H_{37}Cl_2N_3O_2 \cdot 1.00\ C_6H_8O_7 \cdot 0.75\ H_2O$: Calculated: C, 57.10; H, 6.37; N, 5.71; Found: C, 57.14; H, 6.28; N, 5.48.

EXAMPLE 15

5-[(1RS,2SR)-2-(3,4-Dichlorophenyl)-1-hydroxy-4-(4-acetamido-4-phenylpiperidino)butyl]-1-phenyl-1,2,3-(1H)triazole Using a procedure similar to that described in Example 10, except using 5-[(1RS,2SR)-1-acetoxy-2-(3,4-dichlorophenyl)-4-(4-acetamido-4-phenylpiperidino)butyl]-1-phenyl-1,2,3-(1H)-triazole, the title compound was prepared as a light tan powder (78%); mp 125°–128° C.; NMR: 7.72 (s,1), 7.50–7.23 (broad m,10), 7.12 (d,1), 6.80 (s,1), 6.56 (d,1), 5.57 (s,1), 4.85 (d,1), 2.93–2.66 (broad m,3), 2.60–2.22 (broad m,8), 2.02 (s,4), 1.86 (broad d,1); MS: m/z=580((M+1), 37Cl), 578((M+1), 35Cl). Analysis for $C_{31}H_{33}Cl_2N_5O_2 \cdot 0.5\ H_2O$; Calculated: C, 63.37; H, 5.83; N, 11.92; Found: C, 63.51; H, 5.76; N, 11.56.

The starting material 5-[(1RS,2SR)-1-acetoxy-2-(3,4-dichlorophenyl)-4-(4-acetamido-4-phenylpiperidino)butyl]-1-phenyl-1,2,3-(1H)-triazole was prepared as follows:

a. 1-Phenyl-4-trimethylsilyl-1,2,3-triazole. A solution of phenyl azide (2.10 g, 20% in hexane) and trimethylsilylacetylene (5.18 g) in hexane (35 mL) was heated to 50° C. for 3 days. The mixture was cooled to room temperature and the resulting crystals were isolated by filtration and was washed with cold hexane to give 1-phenyl-4-trimethylsilyl-1,2,3-triazole (46%); NMR: 7.94 (s,1), 7.74 (m,2), 7.54–7.26 (m,3), 0.38 (s,9).

b. 1-Phenyl-1,2,3-triazole. A solution of 1-phenyl-4-trimethylsilyl-1,2,3-triazole (1.76 g) in 10% (w/v) aqueous potassium hydroxide was treated with tetrabutylammonium fluoride (2 mg) at 50° C. for 16 hours. An additional quantity (10 mg) of tetrabutylammonium fluoride was added, and the reaction continued for an additional 24 hours at 50° C.; The cooled reaction mixture was partition between diethyl ether and water. The organic extract was washed (water, brine) dried, and evaporated to leave a white foam. crystallization from diethyl ether:hexane (1:2) gave the title compound as an off white solid (970 mg); NMR: 8.00 (d,1), 7.86 (d,1), 7.74 (m,2), 7.57–7.26 (m,3).

c. 5-[(1RS,2SR)-2-(3,4-Dichlorophenyl)-1-hydroxy-4-pentenyl]-1-phenyl-1,2,3-(1H)-triazole. Using a procedure similar to that described in Example 9.c., except using 1-phenyl-1,2,3-triazole in the lithiation reaction at –50° C., the alcohol was prepared as a pale amber syrup (17%); NMR: 7.71 (s,1), 7.54–7.50 (m,3), 7.26–7.17 (m,3), 6.85 (d,1), 6.62 (dd,1), 5.44 (m,1), 4.94–4.90 (m,3), 2.92 (m,2), 2.74 (m,1), 2.38 (m,1).

d. 5-[(1RS,2SR)-1-Acetoxy-2-(3,4-dichlorophenyl)-4-pentenyl]-1-phenyl-1,2,3-(1H)-triazole. Using a procedure similar to that described in Example 7.e., except using 5-[(1RS,2SR)-2-(3,4-dichlorophenyl)-1-hydroxy-4-pentenyl]-1-phenyl-1,2,3-(1H)-triazole and purifying by radial chromatography (2 mm SiO275:25 hexane/ethyl acetate), the acetate was prepared as a colorless glass (61%); NMR: 7.75 (s,1), 7.47 (m,3), 7.18 (m,2), 7.09 (d,1), 6.76 (d,1), 6.49 (dd,1), 5.92 (d,1), 5.38 (m,1), 4.91 (m,2), 3.00 (m,1), 2.70 (m,1), 2.32 (m,1), 2.16 (s,3).

e. 5-[(1RS,2SR)-1-Acetoxy-2-(3,4-dichlorophenyl)-4-oxobutyl]-1-phenyl-1,2,3-(1H)-triazole. Using a procedure similar to that described in Example 7.f., except using 5-[(1RS,2SR)-1-acetoxy-2-(3,4-dichlorophenyl)-4-pentenyl]-1-phenyl-1,2,3-(1H)-triazole, the aldehyde was prepared as a white foam which was used without purification in the next step; MS: m/z=420((M+1), 37Cl), 418((M+1), 35Cl).

f. 5-[(1RS,2SR)-1-acetoxy-2-(3,4-dichlorophenyl)-4-(4-acetamido-4-phenylpiperidino)butyl]-1-phenyl-1,2,3-(1H)-triazole. Using a procedure similar to that described in Example 7, except using 4-acetamido-4-phenylpiperidine as the amine component, and 5-[(1RS,2SR)-1-acetoxy-2-(3,4-dichlorophenyl)-4-oxobutyl]-1-phenyl-1,2,3-(1H)-triazole as the aldehyde component, the coupling product was prepared as a white foam (61%); NMR: 7.75 (s,1), 7.50–7.01 (m,10), 6.79 (d,1), 6.53 (dd,1), 5.94 (d, 1), 5.41 (s,H), 3.03 (m,1), 2.65–2.45 (m,2), 2.33 (m,2), 2.16 (s,3), 2.10–1.98 (m,6), 1.97 (s,3), 1.65 (broad m,2).

The compound of Example 15.f. is also a compound of the invention.

EXAMPLE 16

5-[(1RS,2RS)-2-(3,4-Dichlorophenyl)-1-hydroxy-4-(4-acetamido-4-phenylpiperidino)butyl]-1-phenylpyrazole Using a procedure similar to that described in Example 10, except using 5-[(1RS,2RS)-1-acetoxy-2-(3,4-dichlorophenyl)-4-(4-acetamido-4-phenylpiperidino)butyl]-1-phenylpyrazole, the title compound was prepared as a white powder (77%); mp 128°–130° C.; NMR: 7.55 (s,1), 7.45–7.20 (broad m,12), 6.94 (d,1), 6.17 (s,1), 5.47 (s,1), 5.03 (d,1), 3.00 (m,1), 2.82 (m,1), 2.66 (m,1), 2.47–2.16 (broad m,8), 2.02 (s,3), 1.95 (m,1), 1.78–1.52 (broad m,2); MS: m/z=579((M+1), 37Cl), 577((M+1), 35Cl). Analysis for $C_{32}H_{34}Cl_2N_4O_2 \cdot 0.25\ H2O$; Calculated: C, 66.03; H, 5.97; N, 9.63; Found: C, 66.01; H, 6.04; N, 9.37.

The starting material 5-[(1RS,2RS)-1-acetoxy-2-(3,4-dichlorophenyl)-4-(4-acetamido-4-phenylpiperidino)butyl]-1-phenylpyrazole was prepared as follows.

a. 5-[2-(3,4-Dichlorophenyl)-4-pentenoyl]-1-phenylpyrazole. A solution of oxalyl chloride (633 mg) in dichloromethane (5 mL) was cooled to –78° C. and was treated dropwise with dimethyl sulfoxide (442 mg) in dichloromethane (2 mL). The resulting mixture was stirred at –78° C. for 0.5 hours, was treated with a solution of 5-[2-(3,4-dichlorophenyl)-1-hydroxy-4-pentenyl]-1-phenylpyrazole (70:30 anti/syn) (960 mg), prepared as described in Example 9.c., in dichloromethane (5 mL). The mixture was stirred at –78° C. for 2 hours, was treated with triethylamine (1.30 g), warmed to room temperature and stirred for 1 hour. The mixture was poured into, water and extracted with dichloromethane. The organic extract was washed (water, brine) dried, and evaporated to afford the ketone as a yellow oil (880 mg); NMR: 7.66 (d, 1), 7.46–7.36 (m,5), 7.25–7.22 (m,2), 7.11 (dd,1), 6.96 (d, 1), 5.64 (m,1), 5.02 (m,2), 4.30 (t,1), 2.82 (m,1), 2.49 (m,1).

b. 5-[(1RS,2RS)-2-(3,4-Dichlorophenyl)-1-hydroxy-4-pentenyl]-1-phenylpyrazole. Using a procedure similar to that described in Example 2, except using 5-[(2RS)-2-(3,4-dichlorophenyl)-4-pentenoyl]-1-phenylpyrazole, the title alcohol was obtained as a clear glass (87%); NMR: 7.55 (d,1), 7.46–7.36 (m,5), 7.27 (d,1), 7.12 (d,1), 6.84 (dd,1), 6.21 (d,1), 5.31 (m,1), 4.81 (m,3), 2.85 (m,1), 2.28 (m,1), 2.14 (m,1).

c. 5-[(1RS,2RS)-1-Acetoxy-2-(3,4-dichlorophenyl)-4-pentenyl]-1-phenylpyrazole. Using a procedure similar to that described in Example 7.e., except using 5-[(1RS,2RS) -2-(3,4-dichlorophenyl)-1-hydroxy-4-pentenyl]-1- phenylpyrazole, the acetate was obtained as a clear syrup (85%); NMR: 7.58 (d,1), 7.50–7.38 (m,5), 7.23 (d,1), 7.02 (d,1), 6.74 (dd, 1), 6.20 (d, 1)), 6.09 (d, 1), 5.33 (m,1), 4.84 (m,2), 2.90 (m,1), 2.29 (m,2), 1.99 (s,3).

d. 5-[(1RS,2RS)-1-Acetoxy-2-(3,4-dichlorophenyl)-4-oxobutyl]-1-phenylpyrazole. Using a procedure similar to that described in Example 7.f., except using 5-[(1RS,2RS) -1-acetoxy-2-(3,4-dichlorophenyl)-4-pentenyl]-1-phenylpyrazole, the aldehyde was prepared as an amber oil (97%); MS: m/z=419((M+1), 37Cl), 417((M+1), 35Cl.

e. 5-[(1RS,2RS)-1-Acetoxy-2-(3,4-dichlorophenyl)-4-(4-acetamido-4-phenylpiperidino)butyl]-1-phenylpyrazole. Using a procedure similar to that described in Example 7, except using 4-acetamido-4-phenylpiperidine as the amine component and 5-[(1RS,2RS)-1-acetoxy-2-(3,4-dichlorophenyl)-4-oxobutyl]-1-phenylpyrazole as the aldehyde component, the title compound was obtained as a white foam (65%; NMR: 7.58 (d,1), 7.48–7.21 (m,11), 7.09 (d, 1), 6.81 (dd, 1), 6.22 (d, 1), 6.09 (d, 1), 5.39 (s,1), 3.06 (m,1), 2.51 (m,2), 2.31 (m,2), 2.15–2.00 (m,7), 1.98 (s,3), 1.96 (s,3), 1.75 (m,1), 1.43 (m,1).

The compound of Example 16.e. is also a compound of the invention.

EXAMPLE 17

5-[(1RS,2RS)-2-(3,4-Dichlorophenyl)-1-hydroxy-4-(4-(2-oxoperhydropyrimidin-1-yl)piperidino)butyl]-1-phenylpyrazole Using a procedure similar to that described in Example 7, except using 4-(2-oxoperhydropyrimidin-1-yl)piperidine as the amine component the title compound was prepared as a white powder; mp 174.5°–176° C.; NMR: 7.55 (s,1), 7.44–7.22 (broad m,6), 7.15(s,1), 6.88 (d,1), 6.17 (s,1), 5.06 (d,1), 4.57 (broad s,1), 4.40 (m,1), 3.28 (m,2), 3.20 (m,2), 3.08 (broad d,1), 2.98–2.78 (broad m,2), 2.32–2.11 (broad m,4), 1.93 (m,3), 1.78–1.52 (broad m,7); MS: m/z=544((M+ 1), 37Cl), 542((M+1), 35Cl). Analysis for $C_{28}H_{32}Cl_2N_5O_2 \cdot 0.25 H_2O$: Calculated: C, 61.59; H, 6.00; N, 12.83; Found: C, 61.66; H, 6.10; N, 12.33.

The starting material 4-(2-oxoperhydropyrimidin-1-yl) piperidine was prepared as follows.

a. 8-Benzyloxycarbonyl-1,4-dioxa-8-azaspiro[4.5] decane. Benzyl chloroformate (57.0 g) was added dropwise to a solution of 1,4-dioxa-8-azaspiro[4.5]decane (50.2 g) and pyridine (54.0 mL) in dichloromethane (300 mL) at –5° C. The mixture was allowed to warm to ambient temperature and was stirred overnight. The mixture was washed (1N hydrochloric acid, aqueous sodium bicarbonate), dried and evaporated to give the benzyloxycarbonyl compound as an oil (92.9 g), which was used in the next step without purification; NMR: 7.35 (m,5), 5.13 (s,2), 3.96 (s,4), 3.59 (m,4), 1.67 (m,4); MS: m/z=278(M+1).

b. 1-Benzyloxycarbonyl-4-oxopiperidine. A solution of the above benzyloxycarbonyl compound (92.9 g) in trifluoroacetic acid (100 mL) and water (20 mL) was heated at 50° C. for 1.5 hours, followed by a 2 minute reflux. The mixture was evaporated, neutralized with saturated aqueous sodium bicarbonate, diluted with water, and extracted with dichloromethane. The organic extracts were dried, evaporated, and distilled (156°–164° C.; 11.33–12.00 Pa) to give the ketone as a colorless liquid (59 g); NMR: 7.37 (m,5), 5.18 (s,2), 3.80 (m,4), 2.46 (m,4); MS: m/z=234(M+1).

c. 1-Benzyloxycarbonyl-4-(3-aminopropylamino) piperidine. The above ketone (32.0 g) in methanol (250 mL) was added to a solution of 1,3-diaminopropane (17.2 mL) and acetic acid (23.6 mL) in methanol (250 mL). After 30 minutes, sodium cyanoborohydride (25.9 g) in methanol (250 mL) was added in a single portion. After stirring overnight, the mixture was evaporated and the resulting residue was dissolved in 1N hydrochloric acid (100 mL). Concentrated hydrochloric acid was added dropwise and stirring was continued until the evolution of gas ceased. The acidic aqueous mixture was extracted with dichloromethane (discarded), made basic to pH 10 with 10N sodium hydroxide, and extracted with dichloromethane. The latter dichloromethane extracts were dried and evaporated to give the diamine as a viscous, light yellow oil (25.4 g); NMR (CD$_3$OD): 7.33 (m,5), 5.10 (s,2), 4.13 (m,2), 2.86 (m,2), 2.65 (m,5), 1.90 (m,2), 1.65 (m,2), 1.23 (m,2); MS: m/z= 292(M+1).

d. 1-Benzyloxycarbonyl-4-(2-oxotetrahydropyrimidin-1-yl)piperidine. A stirred solution of the above diamine (10.1 g) and 1,1'-carbonyldiimidazole (6.2 g) in chloroform (250 mL) was heated at reflux for 2 hours. The mixture was washed with water, and the separated organic phase was dried, evaporated, and chromatographed, with dichloromethane:methanol (90:10) as the eluent, to give 1-Benzyloxycarbonyl-4-(2-oxotetrahydropyrimidin-1-yl)-piperidine as a white solid (7.4 g); NMR: 7.35 (m,5), 5.12 (s,2), 4.75 (m,1), 4.50 (m,1), 4.26 (m,2), 3.27 (m,2), 3.13 (m,2), 1.89 (m,2), 1.63 (m,4); MS: m/z=318(M+1).

e. 4-(2-Oxoperhydropyrimidin-1-yl)piperidine. A solution of 1-Benzyloxycarbonyl-4-(2-oxotetrahydropyrimidin-1-yl) piperidine (3.0 g) and 20% palladium hydroxide on carbon (0.410 g) in ethanol (100 mL) was stirred for 3.5 hours under 1 atmosphere of hydrogen. The reaction mixture was filtered through diatomaceous earth and the filtrate was evaporated to give the pyrimidone as a white solid (1.6 g); NMR (CD$_3$OD): 4.25 (m,1), 3.22 (m,4), 3.08 (m,2), 2.63 (m,2), 1.87 (m,2), 1.60 (m,4); MS: m/z=184(M+1).

EXAMPLE 18

5-[(1S,2S)-4-(4-Acetamido-4-phenylpiperidino)-2-(3,4-dichlorophenyl)-1-hydroxybutyl]-1-phenyltriazole Using a procedure similar to that described in Example 10, except substituting 5-[(1S,2S)-4-(4-acetamido-4-phenylpiperidino)-1-acetoxy-2-(3,4-dichlorophenyl)butyl]-1-phenyltriazole, for the acetoxy compound used therein, the title compound was prepared as a white powder; mp 124°–126° C.; NMR: 7.49–7.23 (broad m,12), 7.19(s,1), 6.93 (d, 1), 5.57 (s,1), 5.10 (d,1), 3.03 (s,1), 2.92 (m,1), 2.79 (m,1), 2.58–2.25 (broad m,5), 2.21 (m,2), 2.02 (broad s,4), 1.86 (m,1), 1.47 (m,2); MS: m/z=580((M+1), 37Cl), 58), 578((M+1), 35Cl). Analysis for $C_{31}H_{33}Cl_2N_5O_2 \cdot 1.00 H_2O$: Calculated: C, 62.42; H, 5.91; N, 11.74; Found: C, 62.39; H, 5.81; N, 11.59.

The starting material 5-[(1S,2S)-4-(4-acetamido-4-phenyl-piperidino)-1-acetoxy-2-(3,4-dichlorophenyl)butyl]-1-phenyltriazole, which is also a compound of the invention, was prepared using a sequence similar to that described in Example 7 and the sub-parts thereof, except substituting 1-phenyl-1,2,3-(1H)-triazole for the 1-phenylpyrazole used in 7.c. and substituting 4-acetamido-4-phenylpiperidine for the 4-hydroxy-4-phenylpiperidine used in the reductive amination.

EXAMPLE 19

5-[(1S,2S)-2-(3,4-Dichlorophenyl)-1-hydroxy-4-(2-oxoperhydropyrimidin-1-yl)piperidino)butyl]-1-phenyltriazole Using a procedure similar to that described in Example 10, except substituting 5-[(1S,2S)-4-(4-acetamido-4- phenylpiperidino)-1-acetoxy-2-(3,4-dichlorophenyl)butyl]-1-phenyltriazole for the acetoxy compound used therein, the title compound was prepared as a white powder; mp 130°–132° C.; NMR: 7.52 (s,1), 7.47 (m,3), 7.26 (m,2), 7.20 (d,1), 7.11 (s,1), 6.86 (d,1), 5.10 (d, 1), 4.57 (s,1), 4.48 (m,1), 3.28 (m,2), 3.18 (m,2), 3.08 (broad d,1), 2.98 (m,1), 2.48–2.07 (broad m,4), 2.02–1.51 (broad m,11); MS: m/z= 545((M+1), 37Cl), 543((M+1), 35Cl). Analysis for $C_{28}H_{32}Cl_2N_5O_2 \cdot 0.25\ H_2O$: Calculated: C, 61.59; H, 6.00; N, 12.83; Found: C, 61.66; H, 6.10; N, 12.33.

The starting material 5-[(1S,2S)-4-(4-acetamido-4-phenylpiperidino)-1-acetoxy-2-(3,4-dichlorophenyl)butyl]-1-phenyltriazole, which is also a compound of the invention, was prepared using a sequence similar to that described in Example 7 and the sub-parts thereof, except substituting 1-phenyl-1,2,3-(1H)-triazole for the 1-phenylpyrazole used in 7.c. and substituting 4-(2-oxoperhydropyrimidin-1-yl) piperidine for the 4-hydroxy-4-phenylpiperidine used in the reductive amination.

EXAMPLE 20

5-[(1R,2S)-2-(3,4-Dichlorophenyl)-1-hydroxy-4-(2-oxoperhydropyrimidin-1-yl)piperidino)butyl]-1-phenyl-1,2,3-(1H)-triazole Using a procedure similar to that described in Example 10, except using 5-[(1R,2S)-1-acetoxy-2-(3,4-dichlorophenyl)-4-(2-oxoperhydropyrimidin-1-yl) piperidino)butyl]-1-phenyltriazole, the title compound was prepared as a white powder (73%); mp 116°–118° C.; NMR: 7.75 (s,1), 7.47 (m,3), 7.25 (m,2), 7.11 (d,1), 6.77 (s,1), 6.55 (d,1), 4.85 (d,1), 4.59 (s,1), 4.44 (broad s,1), 3.31–3.17 (broad m,4), 3.00 (broad d,1), 2.86 (broad t,1), 2.50–2.40 (broad m,3), 2.12–1.53 (broad m,12); MS: m/z=545((M+1), 37Cl), 543((M+1), 35Cl). Analysis for $C_{27}H_{32}Cl_2N_6O_2 \cdot 0.75\ H_2O$: Calculated: C, 58.22; H, 6.06; N, 15.09; Found: C, 58.31; H, 5.89; N, 15.09.

The starting material 5-[(1R,2S)-1-acetoxy-2-(3,4-dichlorophenyl)-4-(2-oxoperhydropyrimidin-1-yl)piperidino)butyl]-1-phenyltriazole was prepared as follows.

a. (S)-2-(3,4-Dichlorophenyl)-4-pentenol. Using a procedure similar to that described in Example 9.a., except using (S)-2-(3,4-dichlorophenyl)-4-pentenoic acid and purifying by bulb-to-bulb distillation, the alcohol was prepared as a clear oil which crystallized on standing to afford a waxy solid (86%); mp 33°–34.5° C.; $[\alpha]_D$=+10.1 (c=3.475, methanol); NMR: 7.38 (d,1), 7.31 (d, 1), 7.05 (dd,1), 5.65 (m,1), 4.99 (m,2), 3.77 (m,2), 2.83 (m,1), 2.51–2.28 (m,2). Analysis for $C_{11}H_{12}Cl_2O$: Calculated: C, 57.17; H, 5.23; Found: C, 57.17; H, 5.26.

b. (S)-2-(3,4-Dichlorophenyl)-4-pentenal. Using a procedure similar to that described in Example 9.b., except using (S)-2-(3,4-dichlorophenyl)-4-pentenol, the aldehyde was prepared as a pale yellow syrup (99%), which was used immediately in the next step, and was found racemize on standing; MS: m/z=231((M+1), 37Cl), 229((M+1), 35Cl).

c. 5-[(1R,2S)-2-(3,4-Dichlorophenyl)-1-hydroxy-4-pentenyl]-1-phenyl-1,2,3-(1H)-triazole. Lanthanum (III) chloride (3.24 g) was dried (140° C., 0.2 torr) for 2.5 hours, was cooled to room temperature under nitrogen and suspended in tetrahydrofuran (25 mL). The suspension was stirred for 16 hours. In a separate flask, a solution of n-butyllithium (2.27 mL of a 2.44M solution in hexanes) and tetrahydrofuran (5 mL) was cooled to −50° C. and was treated dropwise with a solution of 1-phenyl-1,2,3-(1H) triazole (760 mg) in tetrahydrofuran (10 mL). The resulting solution was stirred at −50° C. for 1 hour, transferred via cannula onto the cold (−78° C.) lanthanum chloride/ tetrahydrofuran suspension, stirred at −50° C. for 1 hour, and was treated with a solution of (S)-2-(3,4-dichlorophenyl)-4-pentenal (1.00 g) in tetrahydrofuran (25 mL). The mixture was stirred for 1 hour at −50° C.; warmed to 0° C. and quenched by addition of 1% aqueous acetic acid (50 mL). The mixture was diluted with 1% aqueous acetic acid and extracted with ethyl acetate. The organic extract was washed (brine, 1% aqueous acetic acid), dried, and evaporated to leave a yellow syrup. Purification by radial chromatography (2 mm SiO2, 80:20 hexane/ethyl acetate, 50:50 hexane/ethyl acetate, 2 runs, one-half of crude material on each run) afforded the alcohol as a pale yellow foam (502 mg); NMR: 7.70 (s,1), 7.57–7.48 (m,3), 7.23–7.16 (m,3), 6.86 (d,1), 6.62 (dd,1), 5.45 (m,1), 4.92 (m,3), 2.90 (m,1), 2.74 (m,1), 2.38 (m,1).

Also isolated from the chromatographic purification was the (1S,2S) diastereomer as a pale yellow oil (420 mg); NMR: 7.56 (s,1), 7.56–7.16 (m,7), 6.84 (dd,1), 5.38 (m,1), 5.08 (m,1), 4.85 (m,2), 2.88 (m,1), 2.44–2.21 (m,2).

d. 5-[(1R,2S)-1-Acetoxy-2-(3,4-dichlorophenyl)-4-pentenyl]-1-phenyl-1,2,3-(1H)-triazole. Using a procedure similar to that described in Example 7.e., except using 5-[(1R,2S)-2-(3,4-dichlorophenyl)-1-hydroxy-4-pentenyl]-1-phenyl-1,2,3-(1H)-triazole, the acetoxy compound was prepared as a clear syrup (84%); NMR: 7.76 (s,1), 7.49–7.45 (m,3), 7.19–7.08 (m,2), 6.75 (d,1), 6.49 (dd,1), 5.92 (d,1), 5.36 (m,1), 4.91 (m,2), 3.00 (m,1), 2.74 (m,1), 2.32 (m,1).

e. 5-[(1R,2S)-1-Acetoxy-2-(3,4-dichlorophenyl)-4-oxobutyl]-1-phenyl-1,2,3-(1H)-triazole. Using a procedure similar to that described in Example 7.f., except using 5-[(1R,2S)-1-acetoxy-2-(3,4-dichlorophenyl)-4-pentenyl]-1-phenyl-1,2,3-(1H)-triazole, the aldehyde was prepared as a white foam (98%); NMR: 9.63 (s,1), 7.81 (s,1), 7.52–7.45 (m,5), 7.18–7.12 (m,3), 6.80 (d,1), 6.56 (dd,1), 5.89 (d,1), 3.63 (m,1), 2.98–2.73 (m,2).

f. 5-[(1R,2S)-1-Acetoxy-2-(3,4-dichlorophenyl)-4-(2-oxoperhydropyrimidin-1-yl)piperidino)butyl]-1-phenyl-1,2, 3-(1H)triazole. Using a procedure similar to that described in Example 7, except using 4-(2-oxoperhydropyrimidin-1-yl)piperidine and 5-[(1R,2S)-1-acetoxy-2-(3,4-dichlorophenyl)-4-oxobutyl]-1-phenyl-1,2,3-(1H)-triazole, the title compound was prepared as a white foam (34%); MS: m/z=587((M+1), 37Cl), 585((M+1), 35Cl).

The compound of Example 20.f. is also a compound of the invention.

The title compound can alternatively be prepared as follows.

g. A solution of 0.709 g of the compound of Example 22, in 40 mL of methanol was treated with 2.7 mL of 0.9N lithium hydroxide. After stirring for 1 hour the reaction mixture was evaporated and the resulting product was purified by rotory chromatograph using 39:1 chloroform- :methanol to afford the desired product; mp: 115°–117° C.; MS: m/z=542(M+1); NMR (CD3OD): 2.0 (m,12), 3.0 (m,3), 3.5 (m,4), 4.17 (m,1), 4.91 (m,1), 6.82 (dd,1, J=2, 8), 7.05 (d,1, J=2), 7.27 (m,3), 7.61 (m,3), 7.88 (s,1); Analysis for C27H32N6O2Cl2: Calculated: C, 59.66; H, 5.93; N, 15.46; Found: C, 58.75; H, 5.95; N, 14.78.

EXAMPLE 21

5-[(1R,2S)-4-(4-Acetamido-4-phenylpiperidino)-2-(3,4-dichlorophenyl)-1-hydroxybutyl]-1-phenyl-1,2, 3-(1H)-triazole Using a procedure similar to that described in Example 10, except substituting 5-[(1R,2S)-4-(4-acetamido-4- phenylpiperidino)-1-acetoxy-2-(3,4-Dichlorophenyl)butyl]-1-phenyl-1,2,3-(1H)-triazole for the acetoxy compound used therein, the title compound was prepared as a white powder; mp 129.5°–131.5° C.; NMR: 7.73 (s,1), 7.48 (broad m,3), 7.35 (m,3), 7.26 (m,4), 7.12 (d,1), 6.80 (s,1), 6.56 (d,1), 5.54 (s,1), 4.86 (d, 1), 3.01–2.75 (m,3), 2.59–2.18 (broad m,9), 2.03 (broad s,4), 1.78 (m,1); MS: m/z=580 ((M+1), 37Cl), 578((M+1), 35Cl). Analysis for $C_{31}H_{33}Cl_2N_5O_2 \cdot 0.25$ $H_2O$: Calculated: C, 63.86; H, 5.79; N, 12.01; Found: C, 63.76; H, 5.77; N, 11.53.

The starting material 5-[(1R,2S)-4-(4-Acetamido-4-phenylpiperidino)-1-acetoxy-2-(3,4-dichlorophenyl)butyl]-1-phenyl-1,2,3-(1H)-triazole, which is also a compound of the invention, was prepared using a procedure similar to that described in Example 20.f., except substituting 4-acetamido-4-phenylpiperidine for the 4-(2-oxoperhydropyrimidin-1-yl) piperidine used therein.

EXAMPLE 22

5-[(1R,2S)-1-Acetoxy-2-(3,4-dichlorophenyl)-4-(2-oxo-perhydropyrimidin-1-yl)piperidino)butyl]-1-phenyl-1,2,3-(1H)-triazole Citrate Salt A solution of 0.417 g of 5-[(1S,2S)-1-Acetoxy-2-(3,4-dichloro-phenyl)-4-oxobutyl]-1-phenyl-1,2,3-(1H)-triazole in 20 mL of methanol was treated with 0.183 g of 4-(2-oxoperhydropyrimidin-1-yl)piperidine and the pH of the reaction mixture was adjusted to 5.5 by adding glacial acetic acid. After stirring the reaction mixture for 15 minutes., 0.936 g of sodium cyanoborohydride was added and the resulting mixture was stirred for 18 hours. At the end of this period, the reaction mixture was diluted with 3 mL of water and concentrated under reduced pressure. The residue was diluted with sodium chloride solution and extracted twice with chloroform. The combined organic layers were dried over anhydrous sodium sulfate and concentrated under reduced pressure. The resulting oil was purified by roto chromatography over silica gel to afford 0.27 g of the desired material. This product was converted to the citrate salt by dissolving it in ether and treating with a citric acid solution in methanol. The resulting solution was concentrated under reduced pressure and the resulting residue was triturated with ether. The oily material thus obtained was dried under reduced pressure to afford 0.254 g of the desired product; mp: 75°–77° C.; MS: m/z=585(M+1); NMR (CD3OD): 3.2 (m,5), 3.62 (s,3), 4.3 (m,1), 5.9 (d,1, J=10), 6.74 (dd,1, J=2, 8), 7.04 (m,1), 7.17 (m,2), 7.52 (m,3), 7.94 (s,1). Analysis for $C_{29}H_{34}N_6O_3Cl_2 \cdot 1.15$ $C_6H_8O_7 \cdot 0.05$ $H_2O$: Calculated C, 53.41; H, 5.41; N, 10.41; Found C, 53.77; H, 5.66; N, 9.75.

The intermediate 5-[(1S,2S)-1-Acetoxy-2-(3,4-dichlorophenyl)-4-oxobutyl]-1-phenyl-1,2,3-(1H)-triazole was prepared as follows.

a. 5-[(1R,2S)-2-(3,4-Dichlorophenyl)-1-hydroxy-4-pentenyl]-1-phenyl-1,2,3-(1H)-triazole. A solution 5-((S)-2-(3,4-dichlorophenyl)-4-pentenoyl)-1-phenyl-1,2,3-(1H)-triazole (3.11 g, prepared using a procedure similar to that described in Example 7 sub-part c except substituting 1-phenyltriazole for the 1-phenylpyrazole used therein) in 80 mL of anhydrous tetrahydrofuran was added to anhydrous lanthanum trichloride (prepared by heating 7.96 g of lanthanum trichloride heptahydrate under reduced pressure for 16h) and stirring the resulting suspension for 2.5 hours. At the end of this period the reaction mixture was cooled to –78° C., treated with 0.402 g of sodium borohydride and stirred for 1 hour. Upon allowing to warm to the room temperature, the reaction mixture was treated with additional 0.4 g of sodium borohydride and stirred for 16 hours. At the end of this period 50 mL of water and 20 mL of 1N sodium hydroxide were added and the reaction mixture was extracted with chloroform. The organic layer was washed with brine and the aqueous layers were extracted with two portions of chloroform. The organic layers dried and evaporated to afford the crude material. This product was purified by chromatography, with 70:30 hexane:ethyl acetate as the eluent to give 0.52 g of the (1S,2S) isomer; mp 50°–51° C.; $[a]_D = -89.47°$ (c=0.57, EtOH); MS: m/z=372(M+1); NMR (CDCl3): 2.22 (m,1), 2.35(m,1), 2.86(m,1), 4.85(m,2), 4.99 (d,1, J=6.6), 6.87 (dd,1, J=2, 8), 7.18 (d,1, J=2), 7.26 (m,1), 7.37 (m,2), 7.5 (m,4). Isomer 4: mp 116°–117° C.; {a}D 52, C=0.61 ETOH; MS: m/z 372(M+1); and 0.52 g of the desired (1R,2S) isomer; NMR (CDCl3): 2.4 (m,1), 2.6 (m,1), 2.7 (m,1), 4.93 (m,3), 5.46 (m,1), 6.65 (dd,1, J=2.1, 8.4), 6.87 (d,1, J=2), 7.23 (m,3), 7.53 (m,3), 7.73 (s,1).

b. 5-[(1R,2S)-1-Acetoxy-2-(3,4-Dichlorophenyl)-4-pentenyl]-1-phenyl-1,2,3-(1H)-triazole. A solution 1.14 g of the compound from (a) in 20 mL of dichloromethane was treated with 0.344 mL of acetic anhydride, 0.47 mL of triethylamine, followed by 0.037 g of dimethylaminopyridine. Upon stirring for 16 hours the reaction mixture was diluted with dichloromethane and washed with 1N hydrochloric acid. The aqueous layer was extracted with dichloromethane and the combined organic layers were dried and evaporated to afford 1.28 g of the acetate which had a mass spectrum and NMR similar to the material in sub-part f. below.

c. 5-[(1S,2S)-1-Acetoxy-2-(3,4-dichlorophenyl)-4-oxobutyl]-1-phenyl-1,2,3-(1H)-triazole. A solution of 1.28 g of the compound from (b) in 10 mL of ether containing 5 mL of tetrahydrofuran and 10 mL of water was treated with 0.3 mL of 0.16M osmium tetroxide solution followed by 1.449 g of sodium periodate in 3 portions. The reaction mixture was stirred for 3 hours and diluted with water. Extraction with ethyl acetate, washing the organic layer with water, drying the organic layer with anhydrous sodium sulfate and evaporation afforded 1.1 g of the aldehyde; NMR (CDCl3): 2.14 (s,3), 2.81 (m,2), 3.59(m 1), 5.90(d, J=10 Hz, 1), 6.57(d,d, J1=2 Hz, J2=8 Hz, 1), 7.1 (m,3), 7.45 (m,3), 7.80 (s,1), 9.62 (t,J=1).

The (1R,2S) alcohol described at (a) can be prepared from the (1S,2S) alcohol which was also isolated in (a) using the sequence described below.

d. 5-[(1S,2S)-2-(3,4-Dichlorophenyl)-1-mesyloxy-4-pentenyl]-1-phenyl-1,2,3-(1H)-triazole. A solution of 1.74 g of the (1S,2S) alcohol from (a) in 25 mL of anhydrous pyridine at 0° C. was treated with 5.59 mL of methane sulfonyl chloride. The resulting reaction mixture was stirred at 0° C. for 45 minutes and was warmed to room temperature for 1.5 hours. The reaction mixture was poured in ice water and extracted with four portions of dichloromethane. The organic layers were washed with water until the aqueous layers were neutral, dried over anhydrous sodium sulfate and evaporated to afford 2.3 g of the mesylate; NMR (CDCl3): 2.37 (m,2), 2.79 (s,3), 2.93 (m,1), 4.96 (m,2), 5.35 (m,1), 5.93 (d,1, J=6), 6.75 (dd,1, J=2, J=8), 7.04 (d,1, J=2), 7.40 (m,3), 7.58 (m,3), 7.83 (m,1).

e. 5-[(1R,2S)-2-(3,4-Dichlorophenyl)-1-hydroxy-4-pentenyl]-1-phenyl-1,2,3-(1H)-triazole. A solution of 0.56 g of (d) in 16 mL of dimethylsulfoxide and 24 mL of dimethylformamide was treated with 0.327 g of 18-crown-6 (1,4,7,10,13,16-hexaoxacyclooctadecane). Upon cooling to 0° C. the reaction mixture was treated with 0.308 g of potassium super oxide and stirred for 10 minutes. The reaction mixture was diluted with water, treated with sodium thiosulfate and extracted with 4 portions of ether. The organic layers were washed with sodium chloride solution, dried over anhydrous sodium sulfate and evaporated to afford the crude product. This material was purified by chromatography, with 6:4 hexane:ethyl acetate as the eluent to give the alcohol which had a mass spectrum and an NMR similar to the described for the (1R,2S) isomer in (a).

f. 5-[(1R,2S)-1-Acetoxy-2-(3,4-Dichlorophenyl)-4-pentenyl]-1-phenyl-1,2,3-(1H)-triazole. A solution 0.652 g of (e) in 10 mL of dichloromethane was treated with 0.196 mL of acetic anhydride, 0.289 mL of triethylamine followed by 0.021 g of dimethylaminopyridine. Upon stirring for 1.5 hours the reaction mixture was diluted with dichloromethane and washed with 1N hydrochloric acid. The aqueous layer was extracted with dichloromethane and the combined organic layers were dried and evaporated to afford 0.68 g of the acetoxy compound; MS: m/z=416(M+1); NMR (CDCl3): 2.03 (s,3), 2.31 (m,1), 2.62 (m,1), 3.02 (td,1, J=10, 4), 4.9 (m 2), 5.4 (m,1), 5.9 (d,1, J=10), 6.50 (dd,1, J1=2, 8), 6.76 (d, 1, J=2), 7.16 (d,1, J=8), 7.18 (m,2), 7.48 (m,3), 7.76 (s,1).

EXAMPLE 23

5-[(1RS,2SR)-1-Acetoxy-2-(3,4-dichlorophenyl)-4-(2-oxo-perhydropyrimidin-1-yl)piperidino)butyl]-1-phenyl-1,2,3-(1H)-triazole Citrate Salt Using a procedure similar to that described in Example 22 and the sub-parts thereof, except replacing the 5-((S)-2-(3, 4-dichlorophenyl)-4-pentenoyl)-1-phenyl-1,2,3-(1H)-triazole used in sub-part (a), with the racemic 5-(2-(3,4-dichlorophenyl)-4-pentenoyl)-1-phenyl-1,2,3-(1H)-triazole, the title compound was prepared; mp 135°–140° C.; MS and NMR similar to that described for the compound of Example 22.

EXAMPLE 24

5-[(1RS,2SR)-2-(3,4-Dichlorophenyl)-1-hydroxy-4-(2-oxo-perhydropyrimidin-1-yl)piperidino)butyl]-1-phenyl-1,2,3-(1H)-triazole The compound of Example 23 was subjected to a procedure similar to that described in Example 20 sub-part (f) to give the title compound; mp 110°–115° C.; MS and NMR were similar to that described for the compound of Example 20.

EXAMPLE 25

5-[(1RS,2SR)-1-Acetoxy-2-(3,4-dichlorophenyl)-4-[4-(2-oxopiperidino)piperidino]butyl]-1-phenyl-1,2, 3-(1H)-triazole Using a procedure similar to that described in Example 23, except replacing the 4-(2-oxoperhydropyrimidin-1-yl) piperidine used therein with 4-(2-oxopiperidino)piperidine, stirring for 2 hours instead of 18 hours, and eliminating the conversion to the citrate salt, the title compound was prepared; mp 65°–67° C.; MS: m/z=588(M+1); NMR (CD3OD): 1.7 (m,12), 2.13 (s,3), 2.35 (m,2), 2.85 (m,2), 3.13 (m,3), 4.29 (m,1), 5.92 (d,1, J=10), 6.7 (dd,1, J=2, 8), 6.98 (d,1, J=2), 7.22 (m,3), 7.50 (m,3), 7.9 (s,1). Analysis for $C_{30}H_{35}N_5O_3Cl_2 \cdot 2.0$ $H_2O$: Calculated: C, 58.06; H, 6.33; N, 11.28; Found: C, 57.54; H, 5.61; N, 11.13.

The intermediate 4-(2-oxopiperidino)piperidine can be prepared as described in International Patent Application Publication Number WO/148,184 at Example 8 sub-parts a)–c).

EXAMPLE 26

5-[(1R,2S)-2-(3,4-Dichlorophenyl)-1-hydroxy-4-(2-oxopiperidino)piperidino)butyl]-1-phenyl-1,2,3-(1H)-triazole Using a procedure similar to that described in Example 20 sub-part (g) except replacing the 5-[(1R,2S)-1-acetoxy-2-(3, 4-dichlorophenyl)-4-(2-oxoperhydropyrimidin-1-yl) piperidino)butyl]-1-phenyl-1,2,3-(1H)-triazole used therein, with 5-[(1R,2S)-1-acetoxy-2-(3,4-dichlorophenyl)-4-(2-oxopiperidino)piperidino)butyl]-1-phenyl-1,2,3-(1H)-triazole the title compound was prepared; mp 75–80; MS: m/z 546 (M+1); NMR(CD3OD): 1.57(m,2), 1.77(m,7), 2.09 (m,3), 2.27(m, 4), 2.92(m,3), 3.21(m,2), 4.34(m,1), 6.7(d,d, J1=2 Hz, J2=8 Hz, 1), 7.01(d, J=2 Hz, 1), 7.22(m,3), 7.50(m,3), 7.9(s, 1). Analysis for $C_{28}H_{33}N_5O_2Cl_2 \cdot 1.0$ $H_2O$: Calculated C, 59.50; H, 5.93; N, 12.21; Found C, 59.90; H, 6.29; N, 12.49.

The intermediate 5-[(1R,2S)-1-acetoxy-2-(3,4-dichlorophenyl)-4-(2-oxopiperidino)piperidino)butyl]-1-phenyl-1,2,3-(1H)-triazole was prepared using a procedure similar to that described in Example 22 except the 4-(2-oxoperhydropyrimidin-1-yl)piperidine used in Example 22 was replaced with 4-(2-oxopiperidino)piperidine, the reaction was allowed to stir for for 2 hours instead of 18 hours, and the conversion to the citrate salt was not performed.

EXAMPLE 27

5-[(1RS,2SR)-2-(3,4-dichlorophenyl)-1-hydroxy-4-[4-(2-oxopiperidino)piperidino]butyl]-1-phenyl-1,2, 3-(1H)-triazole 5-[(1RS,2SR)-1-Acetoxy-2-(3,4-dichlorophenyl)-4-[4-(2-oxopiperidino)piperidino]butyl]-1-phenyl-1,2,3-(1H)-triazole was subjected to a procedure similar to that described in Example 20 sub-part (g) to give the title compound; mp 85°–90° C.; mass spectrum and NMR were similar to that described for the compound of Example 26. Analysis for $C_{28}H_{33}N_5O_2Cl_2 \cdot 1.0$ $H_2O$: Calculated C, 59.50; H, 5.93; N, 12.21; Found C, 59.67; H, 5.93; N, 12.31.

EXAMPLE 28

5-[(1R,2S)-2-(3,4-dichlorophenyl)-1-hydroxy-4-[4-(methylaminocarbonyl)-4-(2-oxopiperidino) piperidino]butyl]-1-phenyl-1,2,3-(1H)-triazole 5-[(1R,2S)-1-Acetoxy-2-(3,4-dichloro-phenyl)-4-[4-(methylaminocarbonyl)-4-(2-oxopiperidino)piperidino]-butyl]-1-phenyl-1,2,3-(1H)-triazole was subjected to a procedure similar to that described in Example 20 sub-part (g), except the product was converted to the citrate salt; mp 95°–97° C.; MS: m/z=599(M+1); NMR (CD3OD): 1.7 (m,4), 2.3 (m,6), 2.35 (m,2), 2.85 (m,16), 3.43 (m,2), 6.7 (dd,1, J=2, 8), 7.06 (d,1, J=2), 7.16 (m,3), 7.57 (m,3), 7.9 (s,1). Analysis for $C_{30}H_{36}N_6O_3Cl_2 \cdot 0.8$ $H_2O$: Calculated C, 52.9; H, 5.63; N, 9.95; Found C, 53.29; H, 5.74; N, 9.07.

The intermediate 5-[(1RS,2SR)-1-Acetoxy-2-(3,4-dichlorophenyl)-4-[4-(methylaminocarbonyl)-4-(2-oxopiperidino)piperidino]butyl]-1-phenyl-1,2,3-(1H)-triazole was prepared using a procedure similar to that described in Example 22, except replacing the 4-(2-oxoperhydropyrimidin-1-yl)piperidine used therein, with 4-(methylaminocarbonyl)-4-(2-oxo-piperidino)piperidine, and allowing the reaction to stir for 11 days. The acetoxy compound is also a compound or=f the invention.

The intermediate 4-(methylaminocarbonyl)-4-(2-oxopiperidino)piperidine was prepared as follows.

a. 8-Benzyl-1,3,8-triazaspiro[4.5]decane-2,4-dione. 1-Benzyl-4-piperidone (100 g) was added in a single portion to a mechanically stirred suspension of ammonium carbonate (488.5 g) and sodium cyanide (70.0 g) in water (700 mL) and ethanol (700 mL). The reaction mixture was stirred at 60° C. for 12 hours. The inorganic salts dissolve gradually in the solution and spirohydantoin crystals formed. Upon cooling to room temperature, the solids were collected by filtration, washed with warm water (2 L), recrystallized from 80% ethanol (2 L), washed with ethanol, and dried in a vacuum oven at 50° C. to give the hydantoin (122 g) as a white solid; MS: m/z=260(M+1); NMR (DMSO-$d_6$): 10.64 (bs,1), 8.45 (broad s,1), 7.29 (m,5), 3.48 (s,2), 2.69 (m,2), 2.28 (m,2), 1.81 (m,2), 1.51 (m,2).

b. 4-Amino-1-benzyl-4-carboxypiperidine. A stirred solution of the hydantoin (40.0 g) and lithium hydroxide monohydrate (32.4 g) in water (500 mL) was heated at reflux for 40 hours. The mixture was cooled to room temperature, filtered to remove the white precipitate, and the filtrate evaporated. The pH of the concentrate was adjusted from 12 to 5 with concentrated hydrochloric acid and the solution was evaporated to dryness. The residue was suspended in methanol to provide a white precipitate that was filtered, washed with methanol, and air-dried to give the amine (32.7 g) as a white solid; MS: m/z=235(M+1); NMR (DMSO-$d_6$): 7.40 (m,5), 3.89 (m,2), 2.92 (m,4), 2.12 (m,2), 1.84 (m,2).

c. 4-Amino-1-benzyl-4-ethoxycarbonylpiperidine. Thionyl chloride (43.0 mL) was added dropwise to a suspension of the amino-acid (23.0 g) in ethanol (400 mL) at 0° C. to give a clear solution. The reaction mixture was warmed to room temperature, refluxed for 5 hours, and stirred overnight at room temperature. The mixture was evaporated and stripped twice from toluene. The resulting oil was dissolved in water, adjusted to pH 3 with 1N sodium hydroxide, neutralized with saturated aqueous sodium bicarbonate, and extracted with dichloromethane. The organic extracts were dried and evaporated to give the ester (21.5 g) as an oil; MS: m/z=263(M+1); NMR: 7.28 (m,5), 4.17 (q,2, J=7.1), 3.52 (s,2), 2.50 (m,4), 2.13 (m,2), 1.54 (m,4), 1.27 (t,3, J=7.1).

d. 1-Benzyl-4-(5-chlorovaleramido)-4-ethoxycarbonylpiperidine. 5-Chlorovaleryl chloride (13.2 g) in dichloromethane (50 mL) was added dropwise to a solution of the above amino-ester (20.3 g) and pyridine (13.1 mL) in dichloromethane (250 mL) at 0° C., resulting in the formation of a thick slurry within 20 minutes. After being warmed to room temperature overnight, the slurry was diluted with aqueous sodium bicarbonate to give a clear, biphasic solution, which was further extracted with dichloromethane. The organic extracts were dried and evaporated to a light brown semi-solid. The material was suspended in ether and filtered to give the amide (16.8 g) as a white solid; MS: m/z=381(M+1); NMR (CD$_3$OD): 7.28 (m,5), 4.11 (q,2, J=7.1), 3.55 (m,4), 2.68 (m,2), 2.26 (m,4), 2.05 (m,4), 1.75 (m,4), 1.21 (t,3, J=7.1).

e. 1-Benzyl-4-ethoxycarbonyl-4-(2-oxopiperidino) piperidine. A solution of the above amide (16.8 g) in tetrahydrofuran (50 mL) was cannulated into a suspension of sodium hydride (2.1 g) in tetrahydrofuran (150 mL). After being stirred overnight, the reaction mixture was quenched with water, concentrated (to remove tetrahydrofuran), diluted with water, and extracted with dichloromethane. The combined organic extracts were dried and evaporated. The crude product was chromatographed, with dichloromethane:methanol (gradient 97:3, 95:5) as eluent, to give 1-benzyl-4-ethoxycarbonyl-4-(2-oxopiperidino)piperidine (13.2 g) as a solid; MS: m/z=345(M+1); NMR (CD$_3$OD): 7.30 (m,5), 4.11 (q,2, J=7.1), 3.54 (s,2), 3.44 (m,2), 2.66 (m,2), 2.52 (m,2), 2.32 (m,2), 2.20 (m,2), 2.01 (m,2), 1.85 (m,2), 1.74 (m,2), 1.20 (t,3, J=7.1).

f. 4-Ethoxycarbonyl-4-(2-oxopiperidino)piperidine. A solution of 1-benzyl-4-ethoxycarbonyl-4-(2-oxopiperidino) piperidine (12.4 g) and 20% palladium hydroxide on carbon (2.0 g) in ethanol (150 mL) was stirred overnight under hydrogen (1 bar). The reaction mixture was filtered through diatomaceous earth, and the filtrate was evaporated to give 4-ethoxycarbonyl-4-(2-oxopiperidino)piperidine (9.1 g) as a viscous oil; MS: m/z=255(M+1); NMR (CD$_3$OD): 4.13 (q,2, J=7.1), 3.44 (m,2), 2.95 (m,4), 2.32 (m,2), 2.19 (m,2), 1.88 (m,4), 1.74 (m,2), 1.23 (t,3, J=7.1).

g. 1-Benzyloxycarbonyl-4-(ethoxycarbonyl)-4-(2-oxopiperidino)piperidine. 4-(Ethoxycarbonyl)-4-(2-oxopiperidino)piperidine (9.0 g) in dichloromethane (25 mL) was added to a solution of N-(benzyloxycarbonyloxy) succinimide (8.8 g) and triethylamine (5.4 mL) in dichloromethane (150 mL). After 1.5 hours, the reaction mixture was washed successively with 1.0N hydrochloric acid and saturated aqueous sodium bicarbonate. The separated organic layer was dried and evaporated to give the title compound (11.6 g) as a light yellow solid; MS: m/z=389 (M+1); NMR (CDCl$_3$/CF$_3$COOH): 7.37 (m,5), 5.16 (s,2), 4.28 (q,2, J=7.1), 4.09 (m,2), 3.40 (m,2), 3.28 (m,2), 2.53 (m,2), 2.34 (m,2), 1.83 (m,6), 1.30 (t,3, J=7.1).

h. 1-Benzyloxycarbonyl-4-carboxy-4-(2-oxopiperidino) piperidine. A solution of 1-benzyloxycarbonyl-4-ethoxycarbonyl-4-(2-oxopiperidino)piperidine (11.4 g) in tetrahydrofuran (150 mL), 1.0N sodium hydroxide (50 mL), and methanol (volume necessary to obtain clear solution) was heated at reflux for 10 hours. The reaction mixture was evaporated and the resulting aqueous solution was diluted with water and extracted with dichloromethane to recover unreacted starting material (3.7 g). The aqueous phase was acidified to pH 3 with 1.0N hydrochloric acid and extracted with dichloromethane. The combined organic extracts were washed with water, dried, and evaporated to furnish a light yellow solid. The material was suspended in ether and filtered to give the title compound (6.3 g) as a white solid; MS: m/z=361(M+1); NMR (CDCl$_3$/CF$_3$COOH): 7.37 (m,5), 5.17 (s,2), 4.11 (m,2), 3.45–3.32 (m,4), 2.55 (m,2), 2.37 (m,2), 1.94–1.78 (m,6).

i. 1-Benzyloxycarbonyl-4-(methylaminocarbonyl)-4-(2-oxopiperidino)piperidine. A solution of 1-benzyloxycarbonyl-4-carboxy-4-(2-oxopiperidino) piperidine, methylamine hydrochloride, 4-(dimethylamino) pyridine, triethylamine, and 1-(3-dimethylaminopropyl)-3-ethylcarbodiimide hydrochloride in dichloromethane was stirred overnight. The reaction mixture was diluted with dichloromethane and washed successively with 1.0N hydrochloric acid, saturated aqueous sodium bicarbonate, and water. The separated organic layer was dried and evaporated to give the amide as a hygroscopic, white solid; NMR: 7.35 (m,5), 6.72 (m,1), 5.12 (s,2), 3.56 (m,4), 3.30 (m,2), 2.78 (d,3, J=4.8), 2.43 (m,2), 2.27 (m,2), 2.20 (m,2), 1.76 (m,4).

j. 4-(Methylaminocarbonyl)-4-(2-oxopiperidino) piperidine. 1-Benzyloxycarbonyl-4-(methylaminocarbonyl)-4-(2-oxopiperidino)piperidine was hydrogenated over 20% palladium hydroxide on carbon in ethanol overnight. The mixture was filtered through diatomaceous earth, and the filtrate was evaporated to give the piperidine; MS: m/z=240 (M+1); NMR (CD$_3$OD): 3.45 (m,2), 3.10 (m,2), 2.96 (m,2), 2.68 (m,3), 2.32 (m,2), 2.22 (m,2), 1.90 (m,4), 1.75 (m,2).

EXAMPLE 29

5-[(1RS,2SR)-2-(3,4-Dichlorophenyl)-1-methoxy-4-(2-oxoperhydropyrimidin-1-yl)piperidino)butyl]-1-phenyl-1,2,3-(1H)-triazole Using a procedure similar to that described in Example 22, except replacing the 5-[(1S,2S)-1-acetoxy-2-(3,4- dichlorophenyl)-4-oxobutyl]-1-phenyl-1,2,3-(1H)-triazole used therein with 5-[(1RS,2SR)-2-(3,4-dichloro-phenyl)-1-methoxy-4-oxobutyl]-1-phenyl-1,2,3-(1H)-triazole, the title compound was prepared; mp 68–70; MS: m/z 535(M+1); NMR(CD$_3$OD): 1.28 (m,4), 2.0 (m,12), 2.3 (m,1), 2.85 (m,3), 3.2 (m,4), 3.36 (s,3), 4.09 (m,1), 4.58 (d,1, J=9), 6.77 (dd, 1, J=2, 8), 7.00 (d,1, J=2), 7.21 (m,3), 7.55 (m,3), 7.89 (s,1). Analysis for C$_{28}$H$_{34}$N$_6$O$_2$Cl$_2$·0.7 H$_2$O: Calculated C, 58.80; H, 6.27; N, 14.69; Found C, 58.86; H, 6.53; N, 13.11.

The intermediate 5-[(1S,2S)-2-(3,4-dichlorophenyl)-1-methoxy-4-oxobutyl]-1-phenyl-1,2,3-(1H)-triazole was prepared as follows.

a. 5-[(1RS,2SR)-2-(3,4-Dichlorophenyl)-1-methoxy-4-pentenyl]-1-phenyl-1,2,3-(1H)-triazole. A solution of 5-[(1RS,2SR)-2-(3,4-dichlorophenyl)- 1-hydroxy-4-pentenyl]-1-phenyl-1,2,3-(1H)-triazole (0.857 g) in 10 mL of tetrahydrofuran was added to a suspension of 0.0549 g of sodium hydride in 10 mL of tetrahydrofuran at 0° C. After stirring for 0.5 hours the reaction mixture was treated with a solution of 0.712 mL of methyl iodide in 3 mL of tetrahydrofuran and stirred for 2.5 hours. At the end of this period, the reaction mixture was treated with sodium chloride solution and extracted twice with ethyl acetate. The organic layer was dried over anhydrous sodium sulfate and evaporated to afford the crude product which was purified by rotatory chromatography to afford 0.525 g of the desired product; MS: m/z 388 (M+1); NMR (CDCl3): 2.29 (m,1), 2.78 (m,2), 3.32 (s, 3), 4.4 (d,1), 4.9 (m,2), 5.43 (m,1), 6.57 (dd,1, J=2, 8), 6.87 (d, 1, J=2), 7.1 (m,2), 7.49 (m,3), 7.75 (s,1).

b. 5-[(1RS,2SR)-2-(3,4-dichlorophenyl)-1-methoxy-4-oxobutyl]-1-phenyl-1,2,3-(1H)-triazole. Using a procedure similar to that described in Example 22 sub-part (c), except replacing the 5-[(1R,2S)-1-acetoxy-2-(3,4-Dichlorophenyl)-4-pentenyl]-1-phenyl-1,2,3-(1H)-triazole used therein, with 5-[(1RS,2SR)-2-(3,4-dichlorophenyl)-1-methoxy-4-pentenyl]-1-phenyl-1,2,3-(1H)-triazole, the aldehyde was prepared; MS: m/z 326(M+1); NMR(CDCl3): 2.68 (m,1), 3.0 (m,1), 3.0 (s,3), 3.43 (m,1), 4.4 (d,1, J=9), 6.61 (dd,1, J=2 8), 6.83 (d,1, J=2), 7.06 (m,2), 7.53 (m,3), 7.78 (s,1).

EXAMPLES 30–35

Using a reductive coupling procedure similar to that described in Example 7, except replacing the 5-[(1S,2S)-1-acetoxy-2-(3,4-dichlorophenyl)-4-oxobutyl]-1-phenylpyrazole and 4-hydroxy-4-phenylpiperdine used therein, with the requisite aldehyde and piperidine components, the following compounds were prepared.

EXAMPLE 30

5-[(1RS,2SR)-2-(3,4-Dichlorophenyl)-1-pivaloyloxy-4-(2-oxoperhydropyrimidin-1-yl)piperidino)butyl]-1-phenyl-1,2,3-(1H)-triazole citrate salt; NMR (selected signals): 7.68 (s,1), 7.44 (m,2), 7.27 (m,2), 7.10 (d,1), 6.79 (m,1), 6.50 (d,1), 5.88 (d,1), 4.60 (m,1), 4.24 (m,1). Analysis for C$_{32}$H$_{40}$Cl$_2$N$_6$O$_3$·1.1 C$_6$H$_8$O$_7$·0.5 H$_2$O; Calculated: C, 54.68; H, 5.92; N, 9.91; Found C, 54.93; H, 6.07; N 9.68.

EXAMPLE 31

5-[(1RS,2SR)-2-(3,4-Dichlorophenyl)-1-pivolyloxy-4-(2-oxopiperidino)piperidino)butyl]-1-phenyl-1,2,3-(1H)-triazole citrate salt; NMR (selected signals):7.68 (s,1), 7.47 (m,2), 7.27 (m,2), 7.08 (d,1), 6.78 (d,1), 6.48 (dd,1), 5.85 (d,1), 4.45 (m,1); Analysis for C$_{33}$H$_{41}$Cl$_2$N$_5$O$_3$·C$_6$H$_8$O$_7$·$_{H_2}$O; Calculated: C, 55.98; H, 6.14; N, 8.37; Found C, 56.23; H, 6.00; N 8.26.

EXAMPLE 32

5-[(1RS,2SR)-2-(3,4-Dichlorophenyl)-1-benzoyloxy-4-(2-oxoperhydropyrimidin-1-yl)piperidino)butyl]-1-phenyl-1,2,3-(1H)-triazole citrate salt; NMR (selected signals):8.07 (d,1), 7.77 (s,1), 7.63 (m,1), 7.49 (m,3H), 7.15 (d,1), 6.61 (dd,1), 6.21 (d,1); Analysis for C$_{35}$H$_{37}$Cl$_2$N$_5$O$_3$·1.2 C$_6$H$_8$O$_7$; Calculated: C, 56.35; H, 5.23; N, 9.57; Found C, 56.25; H, 5.57; N 9.32.

EXAMPLE 33

5-[(1RS,2SR)-2-(3,4-Dichlorophenyl)-1-benzoyloxy-4-(2-oxopiperidino)piperidino)butyl]-1-phenyl-1,2,3-(1H)-triazole citrate salt; NMR (selected signals):8.08 (d, 1), 7.54 (m,1), 7.49 (m, 3H), 7.32 (m,1), 7.12 (d,1), 6.61 (dd,1), 6.21 (d,1), 4.45 (m,1); Analysis for C$_{35}$H$_{37}$Cl$_2$N$_5$O$_3$·C$_6$H$_8$O$_7$·H$_2$O; Calculated: C, 57.48; H, 5.53; N, 8.17; Found C, 57.215; H, 5.35; N 8.09.

EXAMPLE 34

5-[(1RS,2SR)-2-(3,4-Dichlorophenyl)-1-(4-methoxybenzoyloxy)-4-(2-oxoperhydropyrimidin-1-yl)piperidino)butyl]-1-phenyl-1,2,3-(1H)-triazole citrate salt; NMR (selected signals): 8.03 (d, 1), 7.50 (m,2), 7.31 (m,1), 7.14 (d,2), 6.99 (d,1), 6.85 (d,1), 6.60 (dd,1), 6.18 (d,1), 4.55 (s,1), 4.23 (m,1), 3.90 (s,3); Analysis for C$_{35}$H$_{38}$Cl$_2$N$_6$O$_4$·1.1C$_6$H$_8$O$_7$·0.5 H$_2$O; Calculated: C, 55.35; H, 5.37; N, 9.16; Found C, 55.64; H, 5.36; N 9.36.

EXAMPLE 35

5-[(1RS,2SR)-2-(3,4-Dichlorophenyl)-1-(4-methoxybenzoyloxy)-4-(2-oxopiperidino)piperidino)butyl]-1-phenyl-1,2,3-(1H)-triazole citrate salt; NMR (selected signals): 8.03 (d,1), 7.52 (m,2), 7.32 (m,1), 7.14 (d,1), 6.99 (d,2), 6.96 (d,1), 6.60 (dd,1), 6.19 (d,1), 4.45 (m,1), 3.90 (s,3); Analysis for C$_{36}$H$_{39}$Cl$_2$N$_5$O$_4$·1.1 C$_6$H$_8$O$_7$·0.5 H$_2$O; Calculated: C, 57.04; H, 5.48; N, 7.80; Found C, 56.89; H, 5.43; N 7.88.

The intermediate aldehydes used in Examples 30–35 were prepared as follows.

EXAMPLES 30a.–35a.

Using a procedure similar to that described in Example 7 sub-part (e), except replacing the acetic anhydride used therein, with the requsite acid chloride, the following compounds of formula XXIII, wherein R$^9$ has the indicated value were prepared.

EXAMPLE 30a. AND EXAMPLE 31a.

R$^9$=pivaloyl; MS (CI) 458 (M+H).

EXAMPLE 32a. AND EXAMPLE 33a.

R$^9$=benzoyl; MS (CI) 478 (M+H).

EXAMPLE 34a. AND EXAMPLE 35a.

R$^9$=4-methoxybenzoyl; MS (CI) 508 (M+H).

EXAMPLES 30b.–35b.

Using a procedure similar to that described in Example 7 sub-part (f), except replacing the 5-[(1S,2S)-1-acetoxy-2-(3,4-dichlorophenyl)-4-pentenyl]-1-phenyl-pyrazole used therein, with the requsite alkene, the following aldehydes of formula XXIV wherein R$^{10}$ has the indicated value were prepared.

EXAMPLE 30b. AND EXAMPLE 31b.

$R^{10}$=pivaloyl; MS (CI): 460 (M+H).

EXAMPLE 32b. AND EXAMPLE 33b.

$R^{10}$=benzoyl; MS (CI): 480 (M+H).

EXAMPLE 34b. AND EXAMPLE 35b.

$R^{10}$=4-methoxybenzoyl; MS (CI): 510 (M+H).

EXAMPLE 36

5-[(1RS,2SR)-2-(3,4-Dichlorophenyl)-1-acetylthio-4-(2-oxoperhydropyrimidin-1-yl)piperidino)butyl]-1-phenyl-1,2,3-(1H)-triazole Citrate Salt To a stirred solution of 5-[(1RS,2SR)-1-acetylthio-2-(3,4-dichlorophenyl)-4-oxobutyl]-1-phenyl-1,2,3-(1H)-triazole (0.43 g) in methanol (13 mL) was added 4-(2-oxoperhydropyrimidin-1-yl)piperidine (0.218 g) and the pH adjusted to approximately 6.0 with a few drops of acetic acid. The solution was chilled (ice bath) and sodium cyanoborohydride (0.087 g) was added in one portion. After 10 minutes the ice bath was removed and the solution was stirred at room temperature overnight. Water was added and the reaction mixture made basic using 1N NaOH. The mixture was extracted with ethyl acetate and the combined organic layer dried, filtered, and evaporated to yield a white solid (0.60 g). To the solid dissolved in a small amount of methanol was added anhydrous citric acid (0.188 g). The methanol was removed in vacuo, diethyl ether (10 mL) added and removed in vacuo. The process was repeated with a second portion of diethyl ether to yield the title compound (0.60 g) as a white solid; mp 120°–125° C.; NMR: 1.47–3.39 (m,30) 4.09 (m,1) 4.77 (d,1) 6.23 (s,1), 6.93–7.94 (m,9); MS (CI, $CH_4$): 601(M+1). Analysis for $C_{29}H_{34}Cl_2N_6O_2S\cdot 1.0$ $C_6H_8O_4\cdot 1.0$ $H_2O$: Calculated: C, 51.79; H, 5.46; N, 10.35; Found: C, 51.97; H, 5.26; N, 9.97.

The intermediate 5-[(1RS,2SR)-1-acetylthio-2-(3,4-dichlorophenyl)-4-oxobutyl]-1-phenyl-1,2,3-(1H)-triazole was prepared as follows.

a. 5-[(1RS,2SR)-1-Acetylthio-2-(3,4-dichlorophenyl)-4-pentenyl]-1-phenyl-1,2,3-(1H)-triazole. A solution of freshly prepared cesium thioacetate (1.02 g) and 5-[(1S,2S)-2-(3,4-dichlorophenyl)-4-mesyloxy-4-pentenyl]-1-phenyl-1,2,3-(1H)-triazole (2.0 g) in dimethylformamide (40 mL) were stirred at room temperature overnight. The reaction mixture was partitioned between water and ethyl acetate; the organic layer separated, washed with water (3×50 mL), dried, filtered, and evaporated. Chromatography, with hexane:ether as the eluent 3:2 provided the thio-compound (1.20 g) as a clear tacky solid; NMR (CDCl$_3$): 2.17–2.28 (m,1) 2.38 (s,3) 2.57–2.65 (m,1) 2.88–2.96 (m,1), 4.80–4.95 (m,3), 5.26–5.39 (m,1), 6.58 (dd,1), 7.00 (d,1), 7.18 (d,1), 7.25 (m,2), 7.59 (m,3), 7.63 (s,1); MS (CI, $CH_4$): 432 (M+1).

b. 5-[(1RS,2SR)-1-acetylthio-2-(3,4-dichlorophenyl)-4-oxobutyl]-1-phenyl-1,2,3-(1H)-triazole. To a stirred solution of 5-[(1RS,2SR)-1-acetylthio-2-(3,4-dichloro-phenyl)-4-pentenyl]-1-phenyl-1,2,3-(1H)-triazole (1.2 g) in diethyl ether (4 mL), water (4 mL), and tetrahydrofuran (2 mL) was added a solution of 0.16M osmium tetroxide in water (0.26 mL). After 5 minutes sodium periodate (1.3 g) was added portionwise. After 2 hours at room temperature water was added to the reaction mixture until most of the solids dissolved. The mixture was extracted with ethyl acetate (2×50 mL); the combined organics dried, filtered, and the solvent evaporated. Chromatography, with dichloromethane:ethyl acetate (9:1) as the eluent gave the title compound (1.0 g) as a tacky foam; NMR (CDCl$_3$): 2.39 (s,3) 2.71–2.97 (m 2), 3.54–3.62 (m,1), 4.93 (d,1), 6.67 (dd,1), 6.89 (d,1), 7.17–7.21 (m,3), 7.52–7.57 (m,3), 7.70 (s,1), 9.52 (s,1); MS (CI, $CH_4$): 434 (M+1).

EXAMPLE 37

5-[(1RS,2SR)-2-(3,4-Dichlorophenyl)-1-acetylthio-4-(2-oxopiperidino)piperidino)butyl]-1-phenyl-1,2,3-(1H)-triazole Citrate Salt To a stirred solution of 5-[(1RS,2SR)-1-acetylthio-2-(3,4-dichlorophenyl)-4-pentenyl]-1-phenyl-1,2,3-(1H)-triazole (0.43 g) in methanol (13 mL) was added 4-(2-oxopiperidino) piperidine (0.218 g) and the pH adjusted to approximately 6.0 with a few drops of acetic acid. The solution was chilled (ice bath) and sodium cyanoborohydride (0.087 g) was added in one portion. After 10 minutes the ice bath was removed and the solution stirred at room temperature overnight. Water was added and the reaction mixture was made basic with 1N NaOH. The mixture was extracted with ethyl acetate, the combined organics dried, filtered, and evaporated to yield a white solid (0.51 g). To the solid dissolved in a small amount of methanol was added anhydrous citric acid (0.163 g). The methanol was removed by evaporation and diethyl ether (10 mL) was added and removed by evaporation. The process was repeated with a second portion of diethyl ether to yield the title compound (0.45 g) as a white solid; mp 120°–125° C.; NMR: 1.48–3.33 (m,32), 4.24 (m,1), 4.77 (d,1), 6.93–7.94 (m,9); MS (CI, $CH_4$): 600(M+1). Analysis for $C_{29}H_{34}Cl_2N_6O_2S\cdot 1.0$ $C_6H_8O_4\cdot 1.0$ $H_2O$: Calculated: C, 53.33; H, 5.59; N, 8.64; Found: C, 52.93; H, 5.36; N, 8.87.

EXAMPLE 38

5-[(1RS,2SR)-2-(3,4-Dichlorophenyl)-1-phenylcarbamoyloxy-4-(2-oxoperhydropyrimidin-1-yl)piperidino)butyl]-1-phenyl-1,2,3-(1H)-triazole Citrate Salt To a solution 5-[(1RS,2SR)-2-(3,4-dichlorophenyl)-1-phenylcarbamoyloxy-4-oxobutyl]-1-phenyl-1,2,3-(1H)-triazole (0.30 g) in methanol (10 mL) was added 4-(2-oxoperhydropyrimidin-1-yl)piperidine (0.128 g) and the pH adjusted to approximately 6.0 with a few drops of acetic acid. The solution was chilled (ice bath) and sodium cyanoborohydride (0.057 g) was added in one portion. After 10 minutes the ice bath was removed and the solution was stirred at room temperature overnight. Water was added and the reaction mixture was made basic with 1N NaOH. The mixture was extracted with ethyl acetate, the combined organics dried, filtered, and evaporated to yield a tan solid (0.40 g). To the solid dissolved in a small amount of methanol was added anhydrous citric acid (0.116 g). The methanol was evaporated and diethyl ether (10 mL) added and evaporated. The process was repeated with a second portion of diethyl ether to yield the title compound (0.31 g) as a tan solid; mp 130°–135° C.(d); NMR: 1.47–3.41 (m,27), 4.10 (m,1), 5.86 (d,1), 6.21 (s,1), 6.85–7.98 (m,14); MS (CI, $CH_4$): 662(M+1). Analysis for $C_{34}H_{36}Cl_2N_7O_3\cdot 1.0$ $C_6H_8O_4\cdot 1.0$ $H_2O$: Calculated: C, 55.11; H; 5.32; N; 11.24; Found: C, 54.88; H; 5.27; N; 10.84.

The intermediate 5-[(1RS,2SR)-2-(3,4-dichlorophenyl)-1-phenylcarbamoyloxy-4-oxobutyl]-1-phenyl-1,2,3-(1H)-triazole was prepared as follows.

a. 5-[(1RS,2SR)-2-(3,4-dichlorophenyl)-1-phenylcarbamoyloxy-4-pentenyl]-1-phenyl-1,2,3-(1H)- triazole. To stirred solution of 5-[(1RS,2SR)-2-(3,4-dichlorophenyl)-1-hydroxy-4-pentenyl]-1-phenyl-1,2,3-(1H)-triazole (1.0 g) in dichloromethane (10 mL) was added phenyl isocyanate (0.32 g) and 2 drops of triethylamine and the mixture heated at reflux overnight. Chromatography, with dichloromethane as the eluent, gave the title compound (1.0 g) as a white solid; mp 180°–183° C.; NMR (CDCl$_3$) 2.34–2.37 (m,1), 2.68 (m,1), 2.98–3.05 (m,1), 4.87–4.92 (m,2), 5.37–5.43 (m,1), 6.01 (d,1), 6.49 (dd,1), 6.78 (d,1), 7.08–7.51 (m,11), 7.79 (s,1); MS (CI, CH$_4$): 493(M+1). Analysis for C$_{26}$H$_{21}$Cl$_2$N$_4$O$_2$: Calculated: C, 63.42; H, 4.30; N, 11.38; Found: C, 63.44; H, 4.64, N, 11.40.

b. 5-[(1RS,2SR)-2-(3,4-Dichlorophenyl)-1-phenylcarbamoyloxy-4-oxobutyl]-1-phenyl-1,2,3-(1H)-triazole To a stirred solution of 5-[(1RS,2SR)-2-(3,4-dichlorophenyl)-1-phenylcarbamoyloxy-4-pentenyl]-1-phenyl-1,2,3-(1H)-triazole (1.0 g) in diethyl ether (4 mL), water (4 mL), and tetrahydrofuran (2 mL) was added a solution of 0.16M osmium tetroxide in water (0.22 mL). After 5 minutes sodium periodate (0.96 g) was added portionwise. After 2 hours at room temperature water was added to the reaction mixture until most of the solids dissolve. The mixture was extracted with ethyl acetate (2×50 mL); the combined organic layers dried, filtered, and the solvent evaporated to yield crude product as an oil. Chromatography, with dichloromethane:ethyl acetate (9:1) as the eluent gave the title compound 0.65 g (65%) as a white solid; NMR: 3.12 (d,2), 3.71–3.75 (m,1), 5.84 (d,1) 6.8 (dd,1), 7.03 (t,1), 7.17–7.57 (m,11), 8.01 (s,1), 9.54 (s,1); MS (CI, CH$_4$): 495(M+1).

EXAMPLE 39

5-[(1RS,2SR)-2-(3,4-Dichlorophenyl)-1-phenylcarbamoyloxy-4-(2-oxopiperidino)piperidino)butyl]-1-phenyl-1,2,3-(1H)-triazole Citrate Salt To a solution 5-[(1RS,2SR)-2-(3,4-dichlorophenyl)-1-phenylcarbamoyloxy-4-oxobutyl]-1-phenyl-1,2,3-(1H)-triazole (0.35 g) in methanol (10 mL) was added 4-(2-oxopiperidino)piperidine (0.148 g) and the pH adjusted to approximately 6.0 with a few drops of acetic acid. The solution was chilled (ice bath) and sodium cyanoborohydride (0.062 g) was added in one portion. After 10 minutes the ice bath was removed and the solution stirred at room temperature overnight. Water was added and the reaction mixture made basic with 1N NaOH. The mixture was extracted with ethyl acetate, the combined organics dried, filtered, and evaporated to yield a tan solid (0.47 g). To the solid dissolved in a small amount of methanol was added anhydrous citric acid (0.136 g). The methanol was evaporated and diethyl ether (10 mL) added and evaporated. The process was repeated with a second portion of diethyl ether to yield the title compound (0.30 g) as a tan solid; mp 145°–150° C. (d); NMR: 1.55–3.33 (m,32), 4.35 (m,1), 5.85 (d,1), 6.76–7.99 (m,14); MS (CI, CH$_4$): 661(M+1). Analysis for C$_{35}$H$_{38}$Cl$_2$N$_6$O$_3$·1.2 C$_6$H$_8$O$_4$·2.0 H$_2$O: Calculated: C, 54.61; H, 5.60; N, 9.05; Found: C, 54.34; H, 5.24; N, 9.07.

EXAMPLE 40

5-[(1RS,2SR)-2-(3,4-Dichlorophenyl)-1-methylcarbamoyloxy-4-(2-oxoperhydropyrimidin-1-yl)piperidino)butyl]-1-phenyl-1,2,3-(1H)-triazole Citrate Salt To a solution 5-[(1RS,2SR)-2-(3,4-dichlorophenyl)-1-methylcarbamoyloxy-4-oxobutyl]-1-phenyl-1,2,3-(1H)-triazole (0.32 g) in methanol (10 mL) was added 4-(2-oxoperhydropyrimidin-1-yl)piperidine (0.15 g) and the pH adjusted to approximately 6.0 with a few drops of acetic acid. The solution was chilled (ice bath) and sodium cyanoborohydride (0.065 g) was added in one portion. After 10 minutes the ice bath was removed and the solution was stirred at room temperature overnight. Water was added and the reaction mixture made basic with 1N NaOH. The mixture was extracted with ethyl acetate, the combined organics dried, filtered, and evaporated to yield a white solid (0.35 g). To the solid dissolved in a small amount of methanol was added anhydrous citric acid (0.138 g). The methanol was evaporated and diethyl ether (10 mL) added and evaporated. The process was repeated with a second portion of diethyl ether to yield the title compound (0.39 g) as a white solid, mp 135°–140° C. (d); NMR: 1.49–3.41 (m,30), 4.10 (m,1), 5.70 (d, 1), 6.22 (s,1), 6.78–7.87 (m,9MS (CI, CH$_4$): 600 (M+1). Analysis for C$_{29}$H$_{34}$Cl$_2$N$_7$O$_3$·1.1 C$_6$H$_8$O$_4$·1.0 H$_2$O: Calculated: C, 51.59; H, 5.45; N, 11.83; Found: C, 51.35; H, 5.31; N, 11.37.

The intermediate 5-[(1RS,2SR)-2-(3,4-dichlorophenyl)-1-methylcarbamoyloxy-4-oxobutyl]-1-phenyl-1,2,3-(1H)-triazole was prepared as follows.

a. 5-[(1RS,2SR)-2-(3,4-Dichlorophenyl)-1-methylcarbamoyloxy-4-pentenyl]-1-phenyl-1,2,3-(1H)-triazole. To a stirred solution of 5-[(1RS,2SR)-2-(3,4-dichlorophenyl)-1-hydroxy-4-pentenyl]-1-phenyl-1,2,3-(1H)-triazole (1.0 g) in dichloromethane (10 mL) was added methyl isocyanate (0.17 g) and 2 drops of triethylamine and the mixture stirred at reflux overnight. Evaporation provided the title compound 1.0 g (87%) as a yellow oil; NMR (CDCl$_3$): 2.22–2.35(m,1), 2.61–2.69(m,1), 2.85(d,3), 2.86–2.98 (m,1), 4.84–4.90 (m,2), 5.30–5.44 (m 1), 5.89 (d,1), 6.46 (dd,1), 6.74 (d,1), 7.06 (d,1), 7.22–7.26 (m,2), 7.43–7.51 (m,3), 7.73 (s,1); MS (CI, CH$_4$): 431(M+1).

b. 5-[(1RS,2SR)-2-(3,4-Dichlorophenyl)-1-methylcarbamoyloxy-4-oxobutyl]-1-phenyl-1,2,3-(1H)-triazole. To a stirred solution of (a) (1.0 g) in diethyl ether (4 mL), water (4 mL), and tetrahydrofuran (2 mL) was added a solution of 0.16M osmium tetroxide in water (0.22 mL). After 5 minutes sodium periodate (1.1 g) was added portionwise. After 2 hours at room temperature water is added to the reaction mixture until most of the solids dissolved. The mixture was extracted with ethyl acetate (2×50 mL), the combined organic layer dried, filtered, and evaporated. Chromatography, with dichloromethane:ethyl acetate (8:2) as the eluent, provided the title compound 0.65 g as a clear oil; NMR: 2.56 (d,3), 2.93–3.02 (m,2), 3.61–3.69 (m,1) 5.71 (d,1), 6.80 (d, 1), 7.15–7.56 (m,7), 7.90 (s,1), 9.51 (s,1); MS (CI, CH$_4$): 433(M+1).

EXAMPLE 41

5-[(1RS,2SR)-2-(3,4-Dichlorophenyl)-1-methylcarbamoyloxy-4-(2-oxopiperidino)piperidino)butyl]-1-phenyl-1,2,3-(1H)-triazole Citrate Salt To a stirred solution of 5-[(1RS,2SR)-2-(3,4-dichlorophenyl)-1-methylcarbamoyloxy-4-oxobutyl]-1-phenyl-1,2,3-(1H)-triazole (0.30 g) in methanol (10 mL) was added 4-(2-oxopiperidino)]piperidine (0.145 g) and the pH adjusted to approximately 6.0 with a few drops of acetic acid. The solution was chilled (ice bath) and sodium cyanoborohydride (0.061 g) was added in one portion. After 10 minutes the ice bath was removed and the solution was stirred at room temperature overnight. Water was added and the reaction mixture was made basic with 1N NaOH. The mixture was extracted with ethyl acetate, the combined organics dried, filtered, and evaporated to yield a white solid (0.42 g). To the solid dissolved in a small amount of methanol was added anhydrous citric acid (0.135 g). The methanol was evaporated and diethyl ether (10 mL) added and evaporated. The process was repeated with a second portion of diethyl ether to yield the title compound (0.40 g) as a white solid; mp >135° C. (d); NMR: 1.48–3.41 (m,32), 4.26 (m,1), 5.70 (d, 1), 6.76–7.86 (m,9); MS (CI, $CH_4$): 599 (M+1). Analysis for $C_{30}H_{35}Cl_2N_6O_3 \cdot 1.1\ C_6H_8O_4 \cdot 1.0\ H_2O$: Calculated: C, 53.03; H, 5.69; N, 10.14; Found: C, 52.86; H, 5.62; N, 10.08.

EXAMPLES 42–47

Using procedures similar to those described above, the following compounds were prepared.

EXAMPLE 42

2-[(1RS,2SR)-1-Acetoxy-2-(3,4-Dichlorophenyl)-4-(4-hydroxy-4-phenylpiperidino)butyl]-1-phenylimidazole; mp 166°–168° C.; MS: m/z=578(M+1).

EXAMPLE 43

5-[(1RS,2SR)-1-Acetoxy-2-(3,4-dichlorophenyl)-4-(4-hydroxy-4-phenylpiperidino)butyl]-1-phenylpyrazole; mp 93°–95° C.; MS: m/z=578(M+1).

EXAMPLE 44

5-[2-(3,4-Dichlorophenyl)-1-hydroxy-2-methyl-4-[4-(2-oxoperhydropyrimidin-1-yl)piperidino]butyl]-1-phenylpyrazole; mp 125°–127.5° C.; MS: m/z=556(M+1).

EXAMPLE 45

5-[2-(3,4-Dichlorophenyl)-1-hydroxy-2-methyl-4-[4-(1-ethyl-1-hydroxypropyl)piperidino]butyl]-1-phenylpyrazole; mp 109.5°–111.5° C.; MS: 544(M+1).

EXAMPLE 46

5-[(1RS,2RS)-2-(3,4-Dichlorophenyl)-1-hydroxy-2-methyl-4-(4-acetamido-4-phenylpiperidino)butyl]-1-phenylpyrazole; mp 133°–135° C.; MS: m/z=591(M+1).

EXAMPLE 47

5-[(1RS,2SR)-2-(3,4-Dichlorophenyl)-1-hydroxy-2-methyl-4-(4-acetamido-4-phenylpiperidino)butyl]-1-phenylpyrazole; mp 134.5°–136.5° C.; MS: m/z=591(M+1).

EXAMPLE 48

The following illustrates representative pharmaceutical dosages forms which may be used for the therapeutic or prophylactic administration of a compound of formula I or the N-oxide of the piperidino nitrogen indicated by Δ, or a pharmaceutically acceptable salt thereof, or a quaternary ammonium salt thereof (hereinafter referred to as 'Compound X'):

| (i) | Tablet 1 | mg/tablet |
|---|---|---|
| | 'Compound X' | 100.0 |
| | Lactose | 77.5 |
| | Povidone | 15.0 |
| | Croscarmellose sodium | 12.0 |
| | Microcrystalline cellulose | 92.5 |
| | Magnesium stearate | 3.0 |
| | | 300.0 |
| (ii) | Tablet 2 | mg/tablet |
| | 'Compound X' | 20.0 |
| | Microcrystalline cellulose | 410.0 |
| | Starch | 50.0 |
| | Sodium starch glycolate | 15.0 |
| | Magnesium stearate | 5.0 |
| | | 500.0 |
| (iii) | Capsule | mg/capsule |
| | 'Compound X' | 10.0 |
| | Colloidal silicon dioxide | 1.5 |
| | Lactose | 465.5 |
| | Pregelatinized starch | 120.0 |
| | Magnesium stearate | 3.0 |
| | | 600.0 |
| (iv) | Injection 1 (1 mg/ML) | mg/mL |
| | 'Compound X' (free acid form) | 1.0 |
| | Dibasic sodium phosphate | 12.0 |
| | Monobasic sodium phosphate | 0.7 |
| | Sodium chloride | 4.5 |
| | 1.0 N Sodium hydroxide solution (pH adjustment to 7.0–7.5) | q.s. |
| | Water for injection | q.s. ad 1 mL |
| (v) | Injection 2 (10 mg/mL) | mg/mL |
| | 'Compound X' (free acid form) | 10.0 |
| | Monobasic sodium phosphate | 0.3 |
| | Dibasic sodium phosphate | 1.1 |
| | Polyethylene glycol 400 | 200.0 |
| | 0.1 N Sodium hydroxide solution (pH adjustment to 7.0–7.5) | q.s. |
| | Water for injection | q.s. ad 1 mL |
| (vi) | Aerosol | mg/can |
| | 'Compound X' | 20.0 |
| | Oleic acid | 10.0 |
| | Trichloromonofluoromethane | 5,000.0 |
| | Dichlorodifluoromethane | 10,000.0 |
| | Dichlorotetrafluoroethane | 5,000.0 |

It will be appreciated that the above pharmaceutical compositions may be varied according to well-known pharmaceutical techniques to accomodate differing amounts and types of active ingredient 'Compound X'. The aerosol (vi) may be used in conjunction with a standard, metered dose aerosol dispenser.

FORMULAE

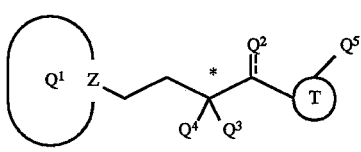

I

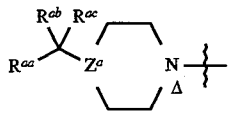

Ia

-continued
FORMULAE
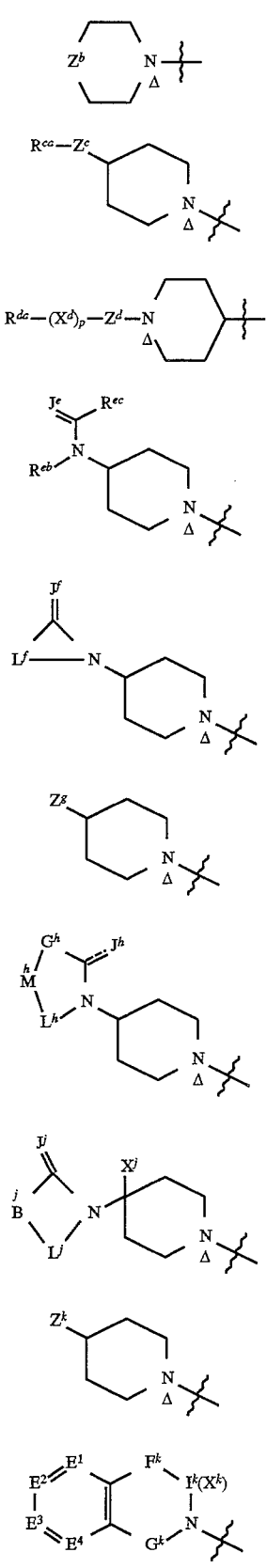
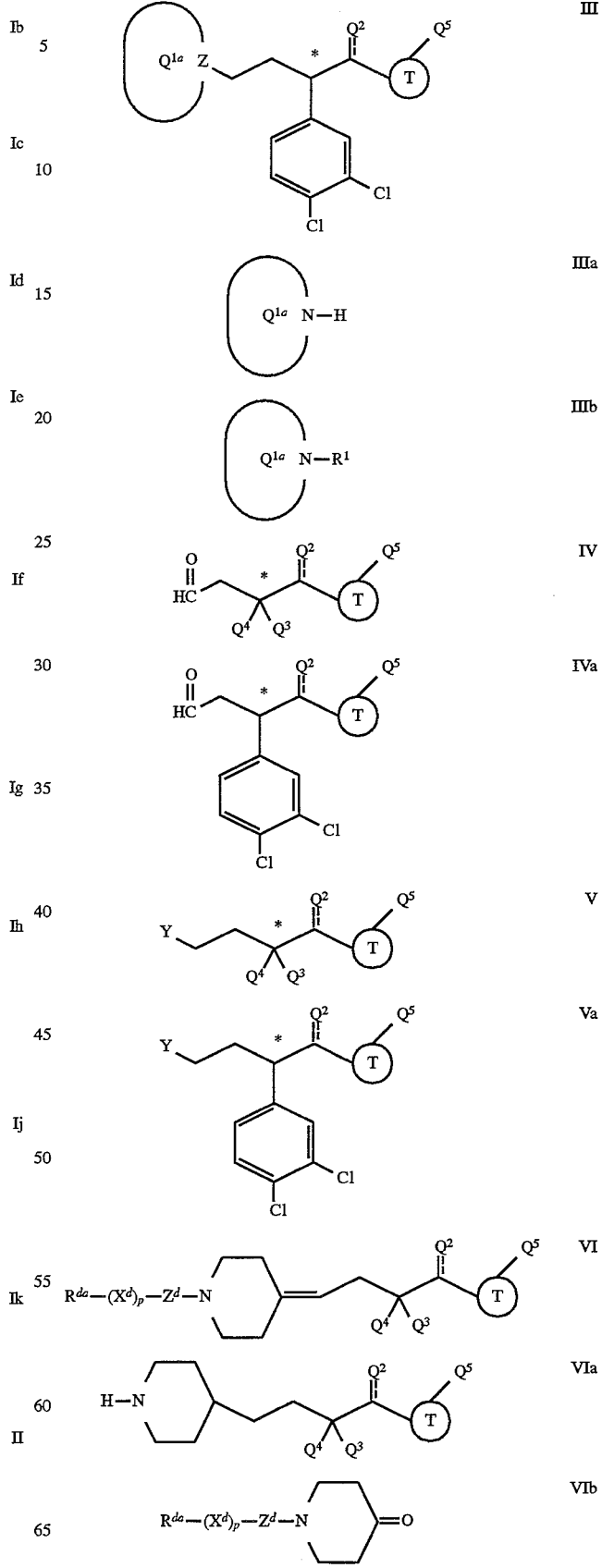

5,635,509
49
-continued
FORMULAE
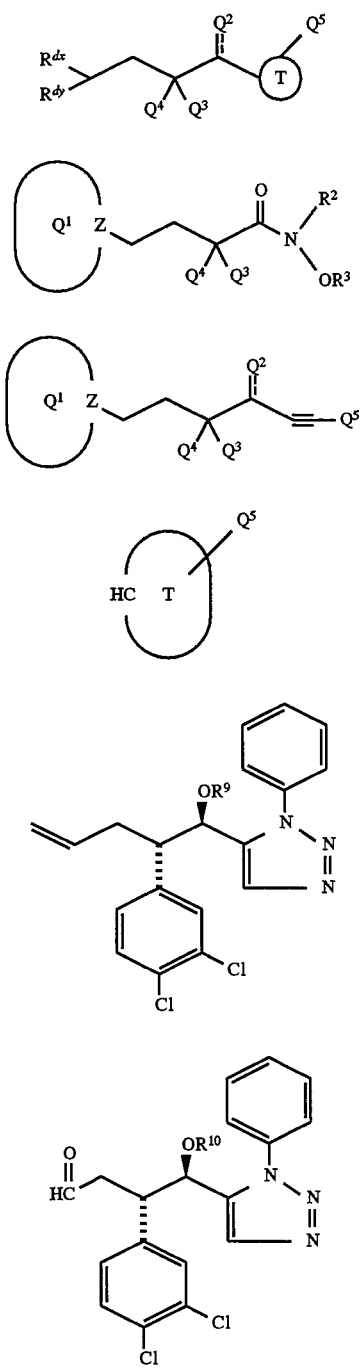
50
-continued
Scheme I
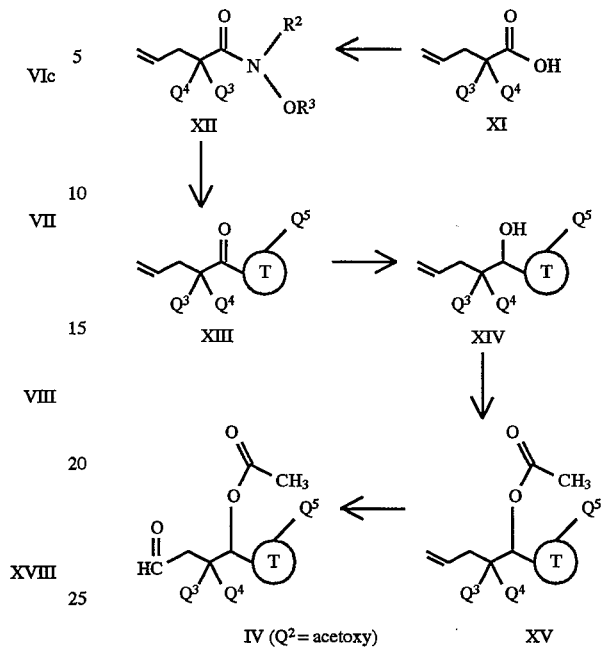
Scheme II
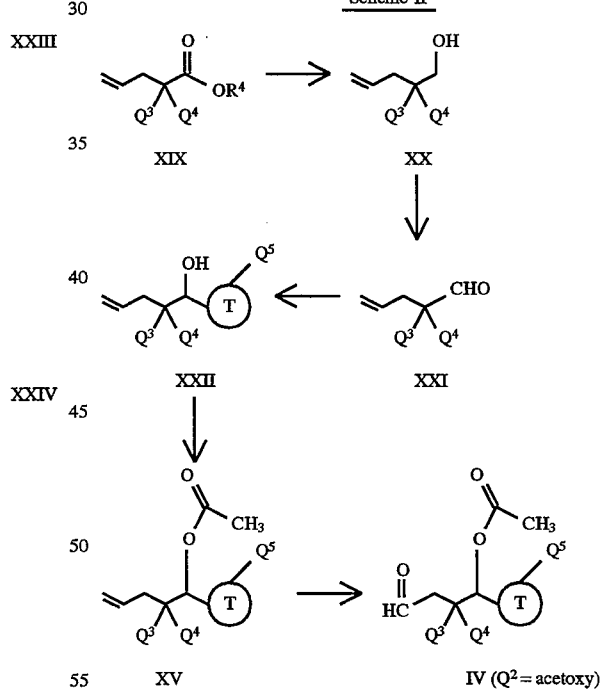
Scheme I
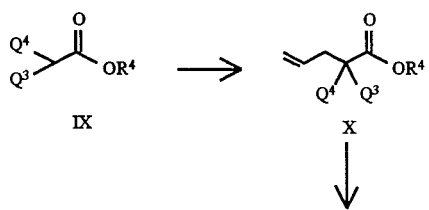
Scheme III
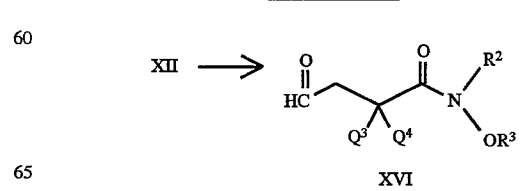

-continued

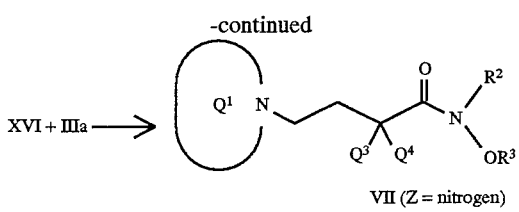

VII (Z = nitrogen)

Scheme IV

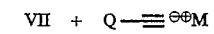

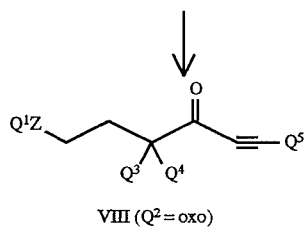

VIII (Q² = oxo)

What is claimed is:

1. A compound of formula I:

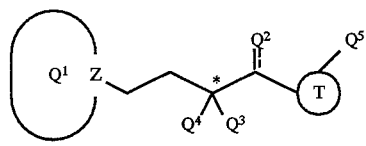

wherein

Q¹ is a radical of formula Ih:
wherein $L^h$ denotes a hydrocarbon radical in which the 1-position is attached to $M^h$ and the values of $G^h$, $J^h$, $M^h$ and $L^h$ are selected from:

(a) $G^h$ is a single bond; $J^h$ is oxo or thioxo; $M^h$ is oxy, thio or $NR^{ha}$; and $L^h$ is $L^{ha}$;

(b) $G^h$ is a single bond; $J^h$ is $NR^{hb}$; $M^h$ is $NR^{ha}$; and $L^h$ is $L^{ha}$;

(c) $G^h$ is a double bond, $J^h$ is $OR^{ha}$, $SR^{ha}$ or $NR^{hc}R^{hd}$; $M^h$ is nitrogen; and $L^h$ is $L^{ha}$;

(d) $G^h$ is methylene which may bear one or two methyl substituents; $J^h$ is oxo, thio or $NR^{he}$; $M^h$ is oxy, thio, sulfinyl, sulfonyl or $NR^{ha}$; and $L^h$ is $L^{hb}$;

(e) $G^h$ is a single bond; $J^h$ is oxo, thioxo or $NR^{he}$; $M^h$ is nitrogen; and $L^h$ is $L^{hc}$;

(f) $G^h$ is methine, which may bear a (1–3C)alkyl substituent; $J^h$ is oxo, thioxo or $NR^{he}$; $M^h$ is nitrogen; and $L^h$ is $L^{hd}$;

(g) $G^h$ is cis-vinylene, which may bear one or two methyl substituents; $J^h$ is oxo, thioxo, or $NR^{he}$; $M^h$ is nitrogen; and $L^h$ is $L^{he}$; and (h) $G^h$ is a single bond; $J^h$ is oxo or thioxo: $M^h$ is a single bond: and $L^h$ is $L^{hf}$;

wherein $R^{ha}$ is hydrogen or (1–3C)alkyl; $R^{hb}$ is hydrogen, (1–3C) alkyl, cyano, (1–3C)alkylsulfonyl or nitro; $R^{hc}$ and $R^{hd}$ are independently hydrogen or (1–3C)alkyl or the radical $NR^{hc}R^{hd}$ is pyrrolidino, piperidino, morpholino, thiomorpholino (or its S-oxide) or piperazinyl (which piperazinyl may bear a (1–3C)alkyl substituent at the 4-position); $R^{he}$ is hydrogen or (1–3C)alkyl; $L^{ha}$ is ethylene, cis-vinylene, trimethylene or tetramethylene which radical $L^{ha}$ itself may bear one or two methyl substituents; $L^{hb}$ is ethylene or trimethylene which radical $L^{hb}$ itself may bear one or two methyl substituents; $L^{hc}$ is prop-2-en-1-yliden-3-yl, which radical $L^{hc}$ itself may bear one or two methyl substituents; $L^{hd}$ is cis-vinylene, which radical $L^{hd}$ itself may bear one or two methyl substituents; $L^{he}$ is methine, which radical $L^{he}$ itself may bear a (1–3C)alkyl substituent; and $L^{hf}$ is 4-oxabutan-1,4-diyl;

$Q^2$ is a mono valent radical selected from hydroxy, (1–3C)alkoxy, —$SR^5$, —OC(=O)$R^6$, and —OC(=O)$NR^7R^8$; or divalent radical selected from thioxo and oxo;

$R^5$ is hydrogen, (1–3C)alkanoyl, (1–3C)alkyl, phenyl, or phenyl(1–3C)alkyl, wherein any phenyl may optionally be substituted by 1–3 substituents selected from halo, (1–3C)alkyl, and (1–3C)alkoxy;

$R^6$ is (1–4C)alkyl, phenyl, or phenyl(1–3C)alkyl, wherein any phenyl may optionally be substituted by 1–3 substituents selected from halo, (1–3C)alkyl, and (1–3C) alkoxy;

$R^7$ and $R^8$ are independently hydrogen, (1–4C)alkyl, phenyl, or phenyl(1–3C)alkyl, wherein any phenyl may optionally be substituted by 1–3 substituents selected from halo, (1–3C)alkyl, and (1–3C)alkoxy;

$Q^3$ is hydrogen or (1–3C)alkyl:

$Q^4$ is phenyl which may bear one or two substituents independently selected from halo, trifluoromethyl, hydroxy, (1–3C)alkoxy, (1–3C)alkyl and methylenedioxy; or $Q^4$ is thienyl, imidazolyl, benzo[b]thiophenyl or naphthyl any of which may bear a halo substituent; or $Q^4$ is biphenylyl; or $Q^4$ is carbon-linked indolyl which may bear a benzyl substituent at the 1-position;

T is a carbon-linked five-membered aromatic ring containing 2–3 nitrogens, which is substiteted at a ring position adjacent to the carbon-link by a group $Q^5$; and $Q^5$ is (1–6C)alkyl (which may contain a double or triple bond), (3–6C)cycloalkyl (which may contain a double bond), (3–6C)oxacycloalkyl (which may contain a double bond), aryl, aryl(1–3C)alkyl, or 5- or 6-membered heteroaryl (or N-oxide thereof) consisting of carbon and one to four heteroatoms selected from oxygen, sulfur and nitrogen, in which an aryl or heteroaryl radical or portion of a radical may bear one or more substituents on carbon selected from (1–3C)alkyl, (1–3C)alkoxy, methylenedioxy, halogeno, hydroxy, (1–4C)acyloxy and $NR^AR^B$ in which $R^A$ and $R^B$ are independently hydrogen or (1–3C)alkyl, or $R^A$ is hydrogen or (1–3C)alkyl and $R^B$ is (1–4C)acyl;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^1$ is (1–4C)alkyl or benzyl and the associated counterion A is a pharmaceutically acceptable anion.

2. A compound of formula I as claimed in claim 1, wherein: $Q^2$ is a mono valent or divalent radical selected from hydroxy, acetoxy, (1–3C)alkoxy and oxo;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^1$ is (1–4C)alkyl or benzyl and the associated counterion A is a pharmaceutically acceptable anion.

3. A compound of formula I as claimed in claim 1 which is a compound of formula III:

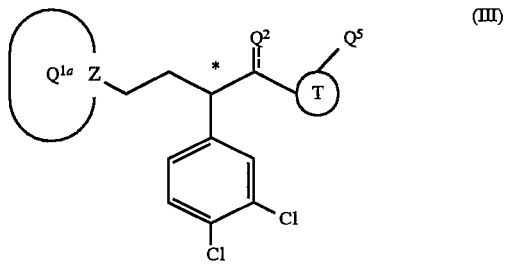

wherein $Q^{1a}$ is a radical of formula Ih; and $Q^2$, T and $Q^5$ have any of the meanings given in claim 1;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^1$ is (1–4C)alkyl or benzyl and the associated counterion A is a pharmaceutically acceptable anion.

4. A compound of formula I as claimed in claim 1, wherein aryl is phenyl; heteroaryl is furyl, pyridyl or pyrimidinyl; halo is chloro or bromo; (1–3C)alkyl is methyl, ethyl, propyl or isopropyl; (1–4C)alkyl is methyl, ethyl, propyl, isopropyl, butyl, isobutyl or t-butyl; (1–5C)alkyl is methyl, ethyl, propyl, isopropyl, butyl, isobutyl, t-butyl, pentyl or isopentyl; (1–6C)alkyl is methyl, ethyl, propyl, isopropyl, butyl, isobutyl, t-butyl, pentyl, isopentyl, hexyl or isohexyl; (1–8C)alkyl is methyl, ethyl, propyl, isopropyl, isopentyl, 1-ethylpropyl, hexyl, isohexyl, 1-propylbutyl, or octyl; (3–6C)cylcoalkyl is cyclopropyl, cyclopentyl or cyclohexyl; (3–7C)cycloalkyl is cyclopropyl, cyclopentyl, cyclohexyl or cycloheptyl; (3–8C)cycloalkyl is cyclopropyl, cyclopentyl, cyclohexyl, cycloheptyl or cyclooctyl; (3–6C) alkenyl is allyl, 2-butenyl or 3-methyl-2-butenyl; (1–4C) alkanoyl is formyl, acetyl, propionyl, butyryl or isobutyryl; and (1–5C)alkanoyl is formyl, acetyl, propionyl, butyryl, isobutyryl, valeryl, isovaleryl or pivaloyl;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^1$ is (1–4C)alkyl or benzyl and the associated counterion A is a pharmaceutically acceptable anion.

5. A compound of formula I as claimed in claim 1, wherein $Q^1$ is 4-(2-oxoperhydropyrimidin-1-yl)piperidino;

$Q^2$ is hydroxy; $Q^3$ is hydrogen; $Q^4$ is 3,4-dichlorophenyl or 3,4-methylenedioxyphenyl; T is imidazol-2-yl, pyrazol-4-yl, pyrazol-3-yl, pyrazol-5-yl, triazol-4-yl, or triazol-5-yl; and $Q^5$ is phenyl;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^1$ is methyl or benzyl; and the associated counterion A is chloride, bromide or methanesulfonate.

6. A compound of formula I as claimed in claim 1, wherein $Q^1$ is 4-(2-oxoperhydropyrimidin-1-yl)piperidino; and T is triazol-5-yl, or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^1$ is (1–4C)alkyl or benzyl and the associated counterion A is a pharmaceutically acceptable anion.

7. A compound of formula I as claimed in claim 1 wherein $J^h$ is oxo; $Q^2$ is hydroxy; $Q^3$ is hydrogen; $Q^4$ is phenyl which may bear one or two substituents selected from halo, trifluoromethyl and methylenedioxy; and $Q^5$ is phenyl;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^1$ is (1–4C)alkyl or benzyl and the associated counterion A is a pharmaceutically acceptable anion.

8. A compound as described in claim 1 which is 5-[(1RS, 2SR)-1-acetoxy-2-(3,4-dichlorophenyl)-4-(2-oxoperhydropyrimidin-1-yl)piperidino)butyl]-1-phenyl-1,2,3-(1H)-triazole; or a pharmaceutically acceptable salt thereof.

9. A pharmaceutical composition comprising a compound of formula I;

or the N-oxide of a piperidino nitrogen indicated by Δ;

or a pharmaceutically acceptable salt thereof;

or a quaternary ammonium salt thereof in which the piperidino nitrogen indicated by Δis a quadricovalent ammonium nitrogen wherein the fourth radical on the nitrogen $R^1$ is (1–4C)alkyl or benzyl and the associated counterion A is a pharmaceutically acceptable anion; as defined in claim 1; and a pharmaceutically acceptable diluent or carrier.

10. A method of treating a disease in a human or other mammal in need thereof, in which NKA is implicated and antagonism of its action is desired, comprising: administering an effective amount of a compound of formula I;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^1$ is (1–4C)alkyl or benzyl and the associated counterion A is a pharmaceutically acceptable anion; as defined in claim 1.

11. A method treating a disease as described in claim 10, wherein the disease is asthma.

* * * * *